United States Patent
Tateno et al.

(10) Patent No.: US 9,427,727 B2
(45) Date of Patent: *Aug. 30, 2016

(54) OXIDE CATALYST, PROCESS FOR PRODUCING OXIDE CATALYST, PROCESS FOR PRODUCING UNSATURATED ACID, AND PROCESS FOR PRODUCING UNSATURATED NITRILE

(75) Inventors: Eri Tateno, Tokyo (JP); Takeo Ichihara, Tokyo (JP); Takaaki Kato, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 459 days.

This patent is subject to a terminal disclaimer.

(21) Appl. No.: 13/882,918

(22) PCT Filed: Oct. 3, 2011

(86) PCT No.: PCT/JP2011/072781
§ 371 (c)(1),
(2), (4) Date: May 1, 2013

(87) PCT Pub. No.: WO2012/060175
PCT Pub. Date: May 10, 2012

(65) Prior Publication Data
US 2013/0225862 A1 Aug. 29, 2013

(30) Foreign Application Priority Data
Nov. 5, 2010 (JP) .................. 2010-248559

(51) Int. Cl.
| | |
|---|---|
| C07C 51/16 | (2006.01) |
| B01J 23/30 | (2006.01) |
| B01J 23/888 | (2006.01) |
| B01J 35/00 | (2006.01) |
| B01J 35/02 | (2006.01) |
| B01J 35/10 | (2006.01) |
| B01J 37/00 | (2006.01) |
| B01J 37/08 | (2006.01) |
| C07C 51/215 | (2006.01) |
| C07C 253/24 | (2006.01) |
| B01J 27/057 | (2006.01) |
| B01J 37/04 | (2006.01) |

(52) U.S. Cl.
CPC ............ *B01J 23/30* (2013.01); *B01J 23/8885* (2013.01); *B01J 27/0576* (2013.01); *B01J 35/002* (2013.01); *B01J 35/0073* (2013.01); *B01J 35/023* (2013.01); *B01J 35/1014* (2013.01); *B01J 37/0045* (2013.01); *B01J 37/04* (2013.01); *B01J 37/08* (2013.01); *C07C 51/215* (2013.01); *C07C 253/24* (2013.01); *B01J 35/008* (2013.01); *B01J 2523/00* (2013.01)

(58) Field of Classification Search
CPC .............. B01J 2523/00; B01J 2523/55; B01J 2523/56; B01J 2523/68; B01J 2523/69; B01J 2523/3712; B01J 2523/53; B01J 2523/305; B01J 2523/31; B01J 2523/3706; B01J 2523/47; B01J 2523/54; B01J 2523/57; B01J 2523/64; B01J 2523/72; B01J 2523/845; B01J 23/30; B01J 23/8885; B01J 27/0576; B01J 35/002; B01J 35/0073; B01J 35/008; B01J 35/023; B01J 35/1014; B01J 37/0045; B01J 37/04; B01J 37/08; C07C 253/24; C07C 51/215; C07C 255/08; C07C 57/04

See application file for complete search history.

(56) References Cited

U.S. PATENT DOCUMENTS

| | | | | |
|---|---|---|---|---|
| 7,919,430 | B2 * | 4/2011 | Tateno ................. | B01J 23/002 502/241 |
| 8,785,675 | B2 * | 7/2014 | Kato ..................... | B01J 23/002 558/303 |
| 2003/0088118 | A1 | 5/2003 | Komada et al. | |
| 2003/0236163 | A1 | 12/2003 | Chaturvedi et al. | |
| 2005/0215818 | A1 | 9/2005 | Yunoki et al. | |
| 2007/0281160 | A1 | 12/2007 | Krishna et al. | |
| 2008/0214863 | A1 | 9/2008 | Cremer et al. | |

FOREIGN PATENT DOCUMENTS

| | | | |
|---|---|---|---|
| EP | 1 908 518 A1 | | 4/2008 |
| EP | 1 997 554 A1 | | 12/2008 |
| EP | 1997554 | * | 12/2008 |

(Continued)

OTHER PUBLICATIONS 862 translated 1998.*

(Continued)

Primary Examiner — Yevegeny Valenrod
Assistant Examiner — Blaine G Doletski
(74) Attorney, Agent, or Firm — Birch, Stewart, Kolasch & Birch, LLP

(57) ABSTRACT

Disclosed is a process for producing an oxide catalyst for use in the gas-phase catalytic oxidation reaction or the like of propane or the like, the process comprising the steps of: (I) obtaining a preparation containing compounds of Mo, V, Nb, and Sb or Te at the predetermined atomic ratios; (II) drying the preparation to obtain a dry powder; and (III) calcining the dry powder, wherein the step (III) comprises the step of calcining the dry powder in the presence of a compound containing W in the form of a solid to obtain a pre-stage calcined powder or a mainly calcined powder, or the step of calcining the dry powder and calcining the obtained pre-stage calcined powder in the presence of the solid to obtain a mainly calcined powder, the solid satisfies the predetermined conditions, and the oxide catalyst comprises a catalytic component having the predetermined composition.

19 Claims, 1 Drawing Sheet

(56) References Cited

FOREIGN PATENT DOCUMENTS

| | | | |
|---|---|---|---|
| EP | 2 570 186 A1 | 3/2013 | |
| JP | 10-28862 | * | 2/1998 |
| JP | 10-28862 A | 2/1998 | |
| JP | 2004-25178 A | 1/2004 | |
| JP | 2005-305428 A | 11/2005 | |
| JP | 2007-320847 A | 12/2007 | |
| JP | 2008-221032 A | 9/2008 | |
| JP | 2009-66463 A | 4/2009 | |
| JP | 2010-520042 A | 6/2010 | |
| WO | WO 01/96016 A1 | 12/2001 | |
| WO | WO 2009/048553 A2 | 4/2009 | |
| WO | WO 2009/151254 A2 | 12/2009 | |

OTHER PUBLICATIONS

Extended European Search Report issued Feb. 24, 2015, in European Patent Application No. 11837828.0.

International Search Report, mailed Jan. 10, 2012, issued in PCT/JP2011/072781.

* cited by examiner

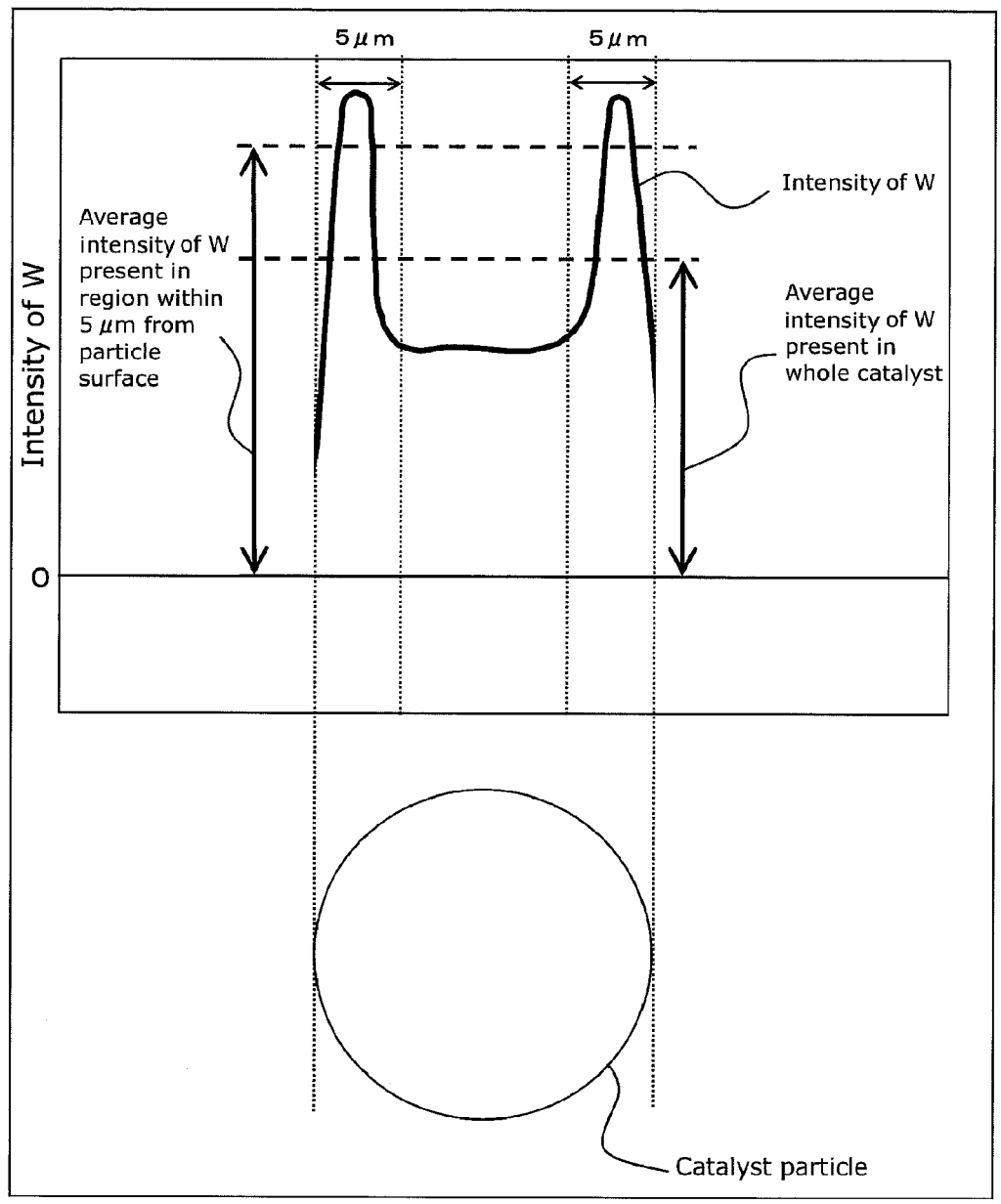

OXIDE CATALYST, PROCESS FOR PRODUCING OXIDE CATALYST, PROCESS FOR PRODUCING UNSATURATED ACID, AND PROCESS FOR PRODUCING UNSATURATED NITRILE

TECHNICAL FIELD

The present invention relates to an oxide catalyst, a process for producing the oxide catalyst, and a process for producing an unsaturated acid and a process for producing an unsaturated nitrile using this oxide catalyst.

BACKGROUND ART

A process for producing a corresponding unsaturated carboxylic acid or unsaturated nitrile from propylene or isobutylene by gas-phase catalytic oxidation or gas-phase catalytic ammoxidation has heretofore been well known. In recent years, an attention has been given to a process for producing a corresponding unsaturated carboxylic acid or unsaturated nitrile by gas-phase catalytic oxidation or gas-phase catalytic ammoxidation using propane or isobutane instead of propylene or isobutylene.

Various oxide catalysts have been proposed as catalysts for gas-phase catalytic ammoxidation. In general, an oxide obtained by mixing molybdenum, vanadium, and the like, as appropriate, and calcining the mixture is directly used as such a catalyst. Meanwhile, an approach for further post-treatment of the catalyst thus calcined has also been studied for producing the unsaturated carboxylic acid or the unsaturated nitrile.

For example, Patent Document 1 discloses an approach which involves impregnating a Mo—V—Sb/Te catalyst with a solution containing one or more element(s) selected from the group consisting of tungsten, molybdenum, chromium, zirconium, titanium, niobium, tantalum, vanadium, boron, bismuth, tellurium, palladium, cobalt, nickel, iron, phosphorus, silicon, rare earth element, an alkali metal, and alkaline earth metal. Patent Document 2 discloses an approach which involves mixing a catalyst with additives such as an antimony compound, a molybdenum compound, a tellurium compound, and a tungsten compound and subjecting the mixture to reaction, or involves mixing a catalyst or a catalyst precursor with the additives, calcining the mixture, followed by reaction.

CITED LIST

Patent Document

[Patent Document 1] Japanese Patent Laid-Open No. 10-028862
[Patent Document 2] WO2009-048553

SUMMARY OF INVENTION

Technical Problem

Patent Document 1 discloses that a catalyst is impregnated with a solution of a metal oxide or the like. However, this impregnation requires the steps of preparing a solution containing a metal oxide or the like, impregnating a catalyst with the solution, drying the catalyst thus impregnated, and re-calcining the catalyst thus dried. This complicates the production steps, compared with those free from such impregnation operation and is disadvantageous to large-scale industrial production.

Patent Document 2 discloses that additives such as metal compounds are added to a catalyst or a catalyst precursor. However, this method does not produce industrially sufficient selectivity or yields. The present inventor presumes that the addition of the additives in too small or large an amount results in the reduced selectivity or yields of the product of interest, even though this is not expressly stated in Patent Document 2. It may be required that the amount of the additives added and their shapes should be defined mutually for getting the most out of the effect of the additives.

Thus, the present invention has been achieved in consideration of these circumstances. An object of the present invention is to provide an oxide catalyst that is for use in the gas-phase catalytic oxidation or gas-phase catalytic ammoxidation reaction of propane or isobutane and can be used to obtain the product of interest at high yields. Another object of the present invention is to provide a process for producing this oxide catalyst, which is suitable for efficient, large-scale industrial production of the oxide catalyst.

Solution to Problem

The present invention is as follows:
[1] A particulate oxide catalyst for use in the gas-phase catalytic oxidation reaction or the gas-phase catalytic ammoxidation reaction of propane or isobutane,
the oxide catalyst containing a Mo compound, a V compound, a Nb compound, a compound of at least one element selected from the group consisting of Sb and Te, a W compound, and an optional compound of at least one element selected from the group consisting of Mn, B, Ti, Al, Ta, an alkali metal, an alkaline earth metal, La, Ce, Pr, Yb, Co, Y, and Sc, at atomic ratios represented by the following formula (0), wherein
W is concentrated within the surface of the particle of the oxide catalyst and in proximity thereto:

$$C_{Mo}:C_V:C_W:C_{Nb}:C_X:C_Z=1:a:w:c:x:z \qquad (0)$$

wherein $C_{Mo}$ represents the atomic ratio of Mo; $C_V$ represents the atomic ratio of V; $C_W$ represents the atomic ratio of W; $C_{Nb}$ represents the atomic ratio of Nb; $C_X$ represents the atomic ratio of at least one element selected from the group consisting of Sb and Te; $C_Z$ represents the atomic ratio of at least one element selected from the group consisting of Mn, B, Ti, Al, Ta, an alkali metal, and an alkaline earth metal; and a, w, c, x, and z fall within the ranges of $0.01 \leq a \leq 1$, $0 < w \leq 2$, $0.01 \leq c \leq 1$, $0.01 \leq x \leq 1$, and $0 \leq z \leq 1$, respectively.
[2] The oxide catalyst according to [1], wherein the average intensity of W present in a region within 5 μm from the surface toward the center of the particle of the oxide catalyst is equal to or greater than 1.08 times that of W present in the whole oxide catalyst.
[3] A process for producing an oxide catalyst for use in the gas-phase catalytic oxidation reaction or the gas-phase catalytic ammoxidation reaction of propane or isobutane, the process comprising the steps of:
(I) obtaining a raw material preparation containing a Mo compound, a V compound, a Nb compound, a compound of at least one element selected from the group consisting of Sb and Te, an optional W compound, and an optional compound of at least one element selected from the group consisting of Mn, B, Ti, Al, Ta, an alkali metal, an alkaline earth metal, La, Ce, Pr, Yb, Co, Y, and Sc, at atomic ratios represented by the following formula (1);
(II) drying the raw material preparation to obtain a dry powder; and
(III) calcining the dry powder, wherein the calcining step (III) comprises the step of calcining the dry powder in the presence of a compound containing W in the form of a solid to obtain a pre-stage calcined powder or a mainly calcined powder, or the step of calcining a pre-stage calcined powder obtained by calcining the dry powder in the presence of a compound containing W in the form of a solid to obtain a mainly calcined powder, and optionally comprises the step of further calcining the mainly calcined powder in the presence of a compound containing W in the form of a solid, the solid satisfies conditions represented by the following formula (2), and the oxide catalyst comprises a catalytic component having a composition represented by the following general formula (3):

$$A_{Mo}:A_V:A_W:A_{Nb}:A_X:A_Z=1:a:b:c:x:z \qquad (1)$$

wherein $A_{Mo}$ represents the atomic ratio of Mo; $A_V$ represents the atomic ratio of V; $A_W$ represents the atomic ratio of W; $A_{Nb}$ represents the atomic ratio of Nb; $A_X$ represents the atomic ratio of at least one element selected from the group consisting of Sb and Te; $A_Z$ represents the atomic ratio of at least one element selected from the group consisting of Mn, B, Ti, Al, Ta, an alkali metal, and an alkaline earth metal; and a, b, c, x, and z fall within the ranges of $0.01 \le a \le 1$, $0 \le b \le 1$, $0.01 \le c \le 1$, $0.01 \le x \le 1$, and $0 \le z \le 1$, respectively;

$$3\ m^{-1} < R_{W/Mo}/d < 600000\ m^{-1} \qquad (2)$$

wherein $R_{W/Mo}$ represents the atomic ratio of W contained in the solid to Mo contained in the dry powder; and d represents the average particle size of the solid; and $$Mo_1V_aW_{b+b'}Nb_cX_xZ_zO_n \qquad (3)$$

wherein a, b, c, x, and z are each as defined above in the formula (1); X represents at least one element selected from the group consisting of Sb and Te; Z represents at least one element selected from the group consisting of Mn, B, Ti, Al, Ta, an alkali metal, an alkaline earth metal, La, Ce, Pr, Yb, Co, Y, and Sc; b' falls within the range of $0.001 \le b' \le 0.3$; and n represents a value which satisfies the balance of valence.

[4] The process for producing an oxide catalyst according to [3], wherein the solid satisfies conditions represented by the following formulas (4) and (5):

$$0.001 < R_{W/Mo} < 0.6 \qquad (4)$$

$$1\ \mu m < d < 300\ \mu m \qquad (5)$$

wherein $R_{W/Mo}$ and d are each as defined above in the formula (2).

[5] The process for producing an oxide catalyst according to [3] or [4], wherein in the formula (1), $0 < b \le 1$.

[6] The process for producing an oxide catalyst according to any one of [3] to [5], wherein the Mo compound, the V compound, the W compound, the Nb compound, the compound represented by X, and the compound represented by Z in the dry powder, the pre-stage calcined powder, or the mainly calcined powder are each at least one selected from the group consisting of an inorganic acid salt, an organic acid salt, an oxide, and a complex oxide.

[7] The process for producing an oxide catalyst according to any one of [3] to [6], further comprising the step of spray-drying a solution or slurry containing W compound to obtain the solid.

[8] The process for producing an oxide catalyst according to any one of [3] to [7], wherein the oxide catalyst comprises the catalytic component supported on silica in an amount of 10 to 80% by mass in terms of $SiO_2$ based on the total amount of the catalytic component and the silica.

[9] A process for producing a corresponding unsaturated acid from propane or isobutane by gas-phase catalytic oxidation reaction, the process comprising using an oxide catalyst obtained by a process according to any one of [3] to [8].

[10] A process for producing a corresponding unsaturated nitrile from propane or isobutane by gas-phase catalytic ammoxidation reaction, the process comprising using an oxide catalyst obtained by a production process according to any one of [3] to [8].

Advantageous Effects of Invention

The present invention can provide an oxide catalyst that is for use in the gas-phase catalytic oxidation reaction or the gas-phase catalytic ammoxidation reaction of propane or isobutane and can be used to obtain the product of interest at high yields. The present invention can also provide a process for producing this oxide catalyst, which is suitable for efficient, large-scale industrial production of the oxide catalyst.

BRIEF DESCRIPTION OF DRAWINGS

FIG. 1 is a schematic diagram for illustrating the average intensity of W.

DESCRIPTION OF EMBODIMENTS

Hereinafter, an embodiment of the present invention (hereinafter, simply referred to as the "present embodiment") will be described in detail. However, the present invention is not intended to be limited to the present embodiment below, and various changes or modifications can be made without departing from the spirit or essential of the present invention.

(1) Oxide Catalyst

An oxide catalyst of the present embodiment is in a particulate form and contains a Mo compound, a V compound, a Nb compound, a compound of at least one element selected from the group consisting of Sb and Te, a W compound, and an optional compound of at least one element selected from the group consisting of Mn, B, Ti, Al, Ta, an alkali metal, an alkaline earth metal, La, Ce, Pr, Yb, Co, Y, and Sc, at atomic ratios represented by the formula (0) shown below. In this oxide catalyst, W is concentrated within the surface of the particle and in proximity thereto.

$$C_{Mo}:C_V:C_W:C_{Nb}:C_X:C_Z=1:a:w:c:x:z \qquad (0)$$

In the formula, $C_{Mo}$ represents the atomic ratio of Mo; $C_V$ represents the atomic ratio of V; $C_W$ represents the atomic ratio of W; $C_{Nb}$ represents the atomic ratio of Nb; $C_X$ represents the atomic ratio of at least one element selected from the group consisting of Sb and Te; and $C_Z$ represents the atomic ratio of at least one element selected from the group consisting of Mn, B, Ti, Al, Ta, an alkali metal, and an alkaline earth metal (hereinafter, these are also collectively referred to as an "element Z").

a, w, c, x, and z fall within the ranges of $0.01 \le a \le 1$, $0 < w \le 2$, $0.01 \le c \le 1$, $0.01 \le x \le 1$, and $0 \le z \le 1$, respectively, from the viewpoint of obtaining the product of interest at high yields. They are preferably $0.01 \le a \le 1$, $0.001 \le w \le 1$, $0.01 \le c \le 1$, $0.01 \le x \le 1$, and $0 \le z \le 1$, more preferably $0.1 \le a \le 0.5$, $0.005 \le w \le 1$, $0.1 \le c \le 0.5$, $0.01 \le x \le 0.5$, and $0.001 \le z \le 0.5$, even more preferably $0.1 \le a \le 0.45$, $0.01 \le w \le 0.5$, $0.1 \le c \le 0.4$, $0.01 \le x \le 0.4$, and $0.001 \le z \le 0.4$.

Moreover, when the oxide catalyst has a composition represented by the general formula (3) and is obtained by a production process described later, it is preferable that w should be the same as b+b' in the formula (3).

In the oxide catalyst of the present embodiment, Mo, V, Nb, and at least one element selected from the group consisting of Sb and Te form a complex oxide, and this complex oxide exhibits activity in the gas-phase catalytic oxidation reaction or the gas-phase catalytic ammoxidation reaction of propane or isobutane. This oxide is further complexed with W to thereby obtain an oxide catalyst that can be used to obtain the product of interest at higher yields. It is preferable that each element should have a composition within the range described above, from the viewpoint of facilitating the formation of active crystals in the gas-phase catalytic oxidation reaction or the gas-phase catalytic ammoxidation reaction.

When the oxide catalyst contains the element Z, this element Z is particularly preferably at least one element selected from the group consisting of Mn, B, and an alkaline earth metal from the viewpoint of, for example, suppressing the combustion of ammonia, reducing the formation of undesired crystals (crystals that inhibits the obtainment of the product of interest), and reducing the formation of a site (decomposition site) at which the product of interest, intermediates (e.g., propylene), or raw material gases (ammonia and propane) are decomposed. Ce is particularly preferable from the viewpoint of reducing the formation of the decomposition site of the product of interest.

In the oxide catalyst of the present embodiment, W is concentrated within the surface of the particle and in proximity thereto. In the present specification, the "concentration" of W means that W is more abundant in a certain region than in other regions. Moreover, the "surface of the particle" refers to the outside surface of the oxide catalyst. When the oxide catalyst has a pore on the internal side of (inside) the particle, a region that is located within the pore inside the particle and may be contacted with gases, liquids, and the like coming in from outside does not apply to the "surface of the particle." Furthermore, the "proximity" to the surface of the particle refers to a region having a depth corresponding to approximately ½ of the distance from the surface of the particle toward the center of the particle. Furthermore, the center of the particle of the oxide catalyst is defined as the midpoint of the longest particle size obtained in the section of the oxide catalyst particle cut in an arbitrary direction.

A preferable region where W is concentrated depends on the type, particle size, amount, and addition method of the tungsten compound (W compound) added in a process for producing the oxide catalyst described later. It is generally preferable that W should be concentrated on a region within 5 μm from the surface of the catalyst particle toward the center of the particle. In this context, the distribution of W in the present specification shall be measured for oxide catalyst particles having a particle size of 40 to 70 μm. Even an oxide catalyst that does not have an average particle size in this range is also regarded as satisfying the preferable concentrated state described above as long as it contains a particle having a particle size of 40 to 70 μm and as a result of measuring the distribution of W for the particle having this particle size, W is concentrated within 5 μm from the surface. The present inventors have realized that the particle of an oxide catalyst for use in fluidized-bed reaction efficiently exerts catalytic effect particularly when having a particle size of 40 to 70 μm. Thus, the oxide catalyst having at least this particle size becomes effective by imparting thereto the preferable distribution of W described above.

It is not required that the boundary should be clear between the region where W is concentrated and a region inwardly thereto (on the central side of the particle therefrom). For example, the abundance of W may be decreased gradually, as it gets close to the center, from the region where W is concentrated (e.g., the region within 5 μm from the surface of the particle toward the center of the particle; W is present at a relatively high concentration) to the region on the internal side where W is present at a relatively low concentration. Alternatively, the abundance of W may be decreased abruptly. When the oxide catalyst is produced by a production process which involves the addition of a W compound as described later, W is concentrated within the surface of the particle and in proximity thereto such that the abundance of W tends to be decreased as it gets close to the center.

The average particle size of the oxide catalyst is preferably 20 to 100 μm. For use in fluidized-bed reaction, the average particle size is more preferably 30 to 90 μm, particularly preferably 40 to 70 μm, from the viewpoint of the fluidity of the catalyst. The average particle size of the catalyst is measured by a method described later.

The components (elements) other than W contained in the oxide catalyst may be distributed, regardless of the distribution of W, in the region where W is concentrated (e.g., the region within 5 μm from the surface of the particle where W is concentrated) and the region on the internal side (on the central side of the particle). Each of these components may be distributed uniformly or may be concentrated in the proximity to the surface, as in W. It is preferable that the components other than W, particularly, at least one element selected from the group consisting of Mo, V, Nb, Sb, and Te, should be present in the region where W is concentrated, from the viewpoint of improving catalyst performance through the interaction between W and the other components and/or, for example, through the substitution of W by the other components during the calcination or reaction of the catalyst in the presence of the tungsten compound (W compound).

It is preferable that W should also be present in the central region of the particle where W is not concentrated. In the present specification, the "central region" refers to a portion inwardly to (on the central side of the particle from) the proximity to the surface of the particle. At least part of W present in the central region are presumed to be substituted on molybdenum (Mo) or vanadium (V) sites in active crystals of the complex oxide, and considered to contribute to heat resistance and redox resistance by affecting the crystal structure of the complex oxide. Therefore, the catalyst particle containing W in the central region tends to have a long catalyst life and be advantageous to long-term industrial use.

For the oxide catalyst of the present embodiment, its composition or structure in a region other than the surface of the particle or the proximity thereto is not particularly limited as long as W is concentrated within the surface of the particle and in proximity thereto and the catalyst satisfies the atomic ratios represented by the formula (0), as a whole. It is preferable that W should be present uniformly at a ratio obtained by subtracting the ratio of the concentrated W from the atomic ratio represented by the formula (0) (i.e., in the obtained ratio, the atomic ratio of W is smaller than the ratio represented by the formula (0)) in the region other than the surface of the particle or the proximity thereto, from the viewpoint of improving the yield of the product of interest.

In the present specification, the term "uniform" described for the distribution and presence of W means that as a result of linear analysis on the composition of the section of the oxide catalyst particle, the intensity of W at a certain site in the region other than the surface of the particle or the proximity thereto is within ±25% based on the average intensity in the whole region other than the surface of the particle or the proximity thereto.

A process for producing the oxide catalyst containing W concentrated within the surface of the particle and in proximity thereto will be described later.

Whether or not W is concentrated within the surface of the particle of the oxide catalyst and in proximity thereto can be determined based on the ratio (Sw0) of the average intensity of W within the surface of the particle and in proximity thereto to that in the whole particle by linear analysis on the composition of the section of the oxide catalyst particle. This ratio (Sw0) of average intensity shall be calculated according to the formula (S1) described later. Moreover, in the linear analysis described later, W can be regarded as being concentrated within the surface of the particle and in proximity thereto when the ratio (Sw) of the average intensity of W present within 5 μm in depth from the surface of the particle toward the center of the particle to that in the whole particle is greater than 1.05. The ratio (Sw) is more preferably equal to or greater than 1.08. This ratio (Sw) of average intensity shall be calculated according to the formula (S2) described later. In this case, the average intensity of W present in the region within 5 μm from the surface of the particle of the oxide catalyst toward the center of the particle can be greater than 1.05 times or equal to or greater than 1.08 times that of W present in the whole oxide catalyst. In the linear analysis, SEM-EDX is used as described later. The other general composition analysis methods, for example, EPMA (Electron Probe X-ray Microanalyzer) may be used. In such a case, a calibration curve for making conversions of numeric values between SEM-EDX and the method is prepared, and Sw may be determined based on the calibration curve.

In the present specification, Sw0 and Sw are specifically measured as follows using SEM-EDX: first, a particle to be assayed is embedded in an appropriate matrix resin (e.g., unsaturated polyester resin), which is then polished to grind the whole thereof until the section of the embedded catalyst particle is exposed. In the polishing, for example, an aqueous suspension containing an abrasive such as aluminum oxide can be used. However, the abrasive is washed off for measurement. Subsequently, the position of the sample is adjusted such that the exposed section of the catalyst particle is placed in the observation field of view in SEM-EDX measurement. Next, the section of the catalyst particle is irradiated with electron beams. The intensity of the characteristic x-ray of W (i.e., the intensity of W) emitted from the electron beam-irradiated portion is counted, while the region to be analyzed is scanned with electron beams to thereby conduct linear analysis. It is preferable that the measurement conditions should be set to an acceleration voltage of 0-15 kV, a dwell time of 1.0 msec, 5000 scans, a spot size of 50, and an operating distance of 10 mm using reflected electron images. A Si (Li) semiconductor is used as a detector. This linear analysis is conducted in a portion having the longest particle size in the section of the catalyst particle. From the obtained linear analysis data, Sw0 and Sw are calculated according to the formulas (S1) and (S2) shown below. In this case, 10 or more particles (each having a particle size of 40 to 70 μm) whose section is exposed up to the center of the particle or the neighborhood thereof are assayed by linear analysis. The Sw0 and Sw of each particle are calculated, and an average value thereof is determined.

$$Sw0 = \text{(Average intensity of W on a diameter from each end (surface) of the longest particle size to a portion corresponding to ¼ of the particle size)}/\text{(Average intensity of W on the whole of the longest particle size)} \quad (S1)$$

$$Sw = \text{(Average intensity of W on a diameter of 5 μm from each end (surface) of the longest particle size)}/\text{(Average intensity of W on the whole of the longest particle size)} \quad (S2)$$

When the Sw0 is greater than 1.00, W is regarded as being concentrated within the surface of the particle of the oxide catalyst and in proximity thereto.

In this context, the "average intensity" refers to the average value of intensity except for background. It is preferable that the data should be collected at 1 μm or less intervals. Moreover, Sw is evaluated for catalyst particles having a particle size of 40 to 70 μm and is not evaluated for catalyst particles having a particle size smaller than 40 μm or larger than 70 μm.

FIG. 1 is a schematic diagram for illustrating the average intensity of W in linear analysis on the average intensity of W in the oxide catalyst particle. This FIG. 1 shows an example of measurement/calculation of Sw. As shown in FIG. 1, the effect of the present invention can be exerted more effectively when the average intensity of W present in the region within 5 μm from the surface of the particle is higher than that of W present in the whole particle of the oxide catalyst and Sw is greater than 1.05.

The oxide catalyst containing W concentrated within the surface of the particle and in proximity thereto has high wear resistance by virtue of the presence of highly hard W within the surface and in proximity thereto and is particularly preferably applied to fluidized-bed reaction. Moreover, W has a higher melting point than that of the other components contained in the catalyst and therefore exhibits the effect of preventing an oxide containing low-melting-point Mo from being deposited within the surface. Thus, such an oxide catalyst is particularly useful when the reaction temperature is high. Furthermore, high-melting-point W concentrated within the surface of the catalyst particle and in proximity thereto is also considered to have the effect of preventing the adhesion of catalysts attributed to the elution of low-melting-point components or preventing deterioration in the fluidity of the catalyst in fluidized-bed reaction.

For the oxide catalyst particle, its surface has the highest frequency of contact between particles and the highest frequency of exposure to a reaction atmosphere (gas/temperature/pressure, etc.). Thus, W, which is concentrated in the region within 5 μm from the surface, i.e., the region relatively close to the surface, can effectively exert its effect even if W is added in a small amount to the oxide catalyst. Moreover, adverse effect on performance, such as the decomposition of ammonia by redundantly added W, can be reduced. In addition, the amount of W added thereto can be saved. Therefore, such an oxide catalyst is also preferable from the economic standpoint.

The amount of W contained on the central side of the particle where W is not concentrated is preferably $0.3 \leq lw < 1$, more preferably $0.5 \leq lw \leq 0.99$ in the linear analysis, wherein lw=(Average intensity of W on a diameter from a portion corresponding to 5 μm from each end (surface) of the longest particle size to the center)/(Average intensity of W in the whole of the longest particle size).

(2) Process for Producing Oxide Catalyst

A process for producing the oxide catalyst of the present embodiment is a process for producing an oxide catalyst for use in the gas-phase catalytic oxidation reaction or the gas-phase catalytic ammoxidation reaction of propane or isobutane, the process comprising the steps of: (I) obtaining a raw material preparation containing a Mo compound, a V compound, a Nb compound, and a compound of at least one element selected from the group consisting of Sb and Te, at particular atomic ratios (hereinafter, referred to as a "raw material preparation step"); (II) drying the raw material preparation to obtain a dry powder (hereinafter, referred to as a "drying step"); and (III) calcining the dry powder (hereinafter, referred to as a "calcination step").

(I) Raw Material Preparation Step

In the raw material preparation step, preferably, a compound containing each element constituting the oxide catalyst is dissolved or dispersed in a solvent and/or a dispersion medium to obtain a raw material preparation. Water can usually be used as the solvent and/or the dispersion medium. Hereinafter, the step using water as the solvent and/or the dispersion medium will be described. The amount of the solvent and/or the dispersion medium contained in the raw material preparation is preferably 70 to 95% by mass, more preferably 75 to 90% by mass, based on the whole amount of the final raw material preparation, from the viewpoint of, for example, fully dissolving and/or dispersing the compound containing each element constituting the oxide catalyst (hereinafter, also simply referred to as a "catalyst-constituting element"), appropriately adjusting the redox state of the catalyst-constituting element, and adjusting the viscosity of the raw material preparation immediately before spray-drying in order to allow the obtained catalyst particle to have preferable shape and/or strength.

The compound containing each element constituting the oxide catalyst (also including salts; hereinafter, also simply referred to as a "constitutive element compound") can be used as a component contained in the raw material preparation. In the raw material preparation step, dissolution procedures, mixing procedures, or dispersion procedures for the constitutive element compounds are not particularly limited. Raw materials such as the constitutive element compounds may be dissolved, mixed, or dispersed in the same aqueous medium. Alternatively, raw materials such as the constitutive element compounds are separately dissolved, mixed, or dispersed in different aqueous media, and then, these aqueous media may be mixed. Moreover, heating and/or stirring may be performed, if necessary. The mixing ratio of each constitutive element compound can be adjusted appropriately in consideration of the ratio of each constitutive element in the finally obtained oxide catalyst, and the amount of each constitutive element compound (added in the subsequent steps such as the calcination step) contained therein.

It is preferable that the raw material preparation should contain Mo, V, Nb, and Te and/or Sb. The raw material preparation may contain at least one selected from the group consisting of Mn, B, Ti, Al, Ta, an alkali metal, an alkaline earth metal, La, Ce, Pr, Yb, Co, Y, and Sc, in addition to those elements, and may also contain W. Examples of the constitutive element compounds include, but not particularly limited to, compounds shown below.

Examples of the Mo-containing compound (hereinafter, referred to as a "Mo compound"; the same holds true for the other elements) serving as a raw material for Mo include ammonium heptamolybdate [$(NH_4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentachloride [$MoCl_5$]. Among them, ammonium heptamolybdate [$(NH_4)_6Mo_7O_{24} \cdot 4H_2O$] is preferable from the viewpoint of solubility, valence of Mo, versatility, easy availability, etc.

Examples of the V compound serving as a raw material for V include ammonium metavanadate [$NH_4VO_3$], vanadium pentoxide [$V_2O_5$], and vanadium chloride [$VCl_4$ or $VCl_3$]. Among them, ammonium metavanadate [$NH_4VO_3$] is preferable from the viewpoint of solubility, valence of V, versatility, easy availability, etc.

Examples of the Nb compound serving as a raw material for Nb include niobic acid, inorganic acid salts of niobium, and organic acid salts of niobium. Among them, niobic acid is preferable from the viewpoint of solubility, valence of Nb, versatility, easy availability, etc. The niobic acid is represented by the chemical formula $Nb_2O_5 \cdot nH_2O$ and is also called niobium hydroxide or niobium oxide hydrate. Furthermore, niobium can be dissolved in an aqueous dicarboxylic acid solution and used as the Nb compound. For this Nb compound, the dicarboxylic acid/niobium molar ratio is preferably 1 to 4. Moreover, the dicarboxylic acid is preferably oxalic acid from the viewpoint of solubility and appropriate complexation with Nb.

Examples of the Sb compound serving as a raw material for Sb include antimony oxide [$Sb_2O_3$ or $Sb_2O_5$], antimonous acid [$HSbO_2$], antimonic acid [$HSbO_3$], ammonium antimonate [$(NH_4)SbO_3$], antimony chloride [$Sb_2Cl_3$], organic acid salts (e.g., tartrate) of antimony, and metal antimony. Among them, diantimony trioxide [$Sb_2O_3$] is preferable from the viewpoint of solubility, valence of Sb, versatility, easy availability, etc.

Examples of the Te compound serving as a raw material for Te include telluric acid [$H_6TeO_6$] and metal tellurium. Among them, telluric acid [$H_6TeO_6$] is preferable from the viewpoint of solubility, valence of Te, versatility, easy availability, etc.

Examples of the W compound serving as a raw material for W include ammonium paratungstate, ammonium metatungstate, tungstic acid, tungsten trioxide, tungsten dioxide, silicotungstic acid, silicotungstomolybdic acid, silicovanadotungstic acid, sodium tungstate, calcium tungstate, and cobalt tungstate. Among them, tungsten trioxide, ammonium metatungstate, and cobalt tungstate are preferable from the viewpoint of solubility, valence of W, versatility, easy availability, the influence of metal elements coexisting therewith, etc.

The compound serving as a raw material for Mn, B, Ti, Al, Ta, an alkali metal, an alkaline earth metal, La, Ce, Pr, Yb, Co, Y, or Sc (hereinafter, referred to as a "compound represented by Z") is not particularly limited as long as it is a substance containing each of these elements. Examples thereof include compounds containing each of these elements and these metal elements solubilized in appropriate reagents. Examples of the compounds containing each of these elements include ammonium salt, nitrate, carboxylate, ammonium carboxylate, peroxocarboxylate, ammonium peroxocarboxylate, ammonium halide, halide, acetyl acetonate, and alkoxide. Among them, water-soluble raw materials such as nitrate and carboxylate are preferable.

When the oxide catalyst is a silica-supported catalyst, it is preferable that the raw material preparation should contain a raw material for silica. Silica sol can be used as the raw material for silica. A silica powder can also be used in a portion or the whole amount of the raw material for silica.

It is preferable that the silica sol should contain preferably 0 to 270 mass ppm, more preferably 10 to 270 mass ppm of nitric acid ions, based on the mass of $SiO_2$ (silica) therein. In the present specification, the term "silica sol" refers to an aqueous silicic acid solution in a clear state. The product of interest is obtained at further favorable yields by adjusting, to the particular range, the nitric acid ion concentration in the silica sol serving as a raw material for the silica carrier and using such silica sol as a raw material for the carrier. In addition, a silica-supported catalyst further excellent in physical strength is obtained. This may be because the aggregated state of the silica sol can be controlled more appropriately, though the reason is uncertain.

In this context, the nitric acid ion concentration based on the mass of silica in the silica sol can be determined by ion chromatography. A measurement apparatus and measurement conditions are shown below. An ion chromatograph manufactured by TOSOH CORP. (trade name "IC-2001")

can be used as a measurement apparatus. TSKgel superIC-AZ is used as a column, and TSKguardcolumn superIC-AZ is used as a guard column. Furthermore, TSKsuppress A is used as a washing solution for suppressor valves. A 1.9 mmol/L aqueous $NaHCO_3$ solution and a 3.2 mmol/L aqueous $Na_2CO_3$ solution are mixed and used as an eluent. In this case, the flow rate is set to 0.8 mL/min.

First, a method for industrially producing the silica sol will be described in order to illustrate a method for controlling the nitric acid ion concentration in the silica sol. Examples of the method for industrially producing the silica sol includes methods such as (1) water glass neutralization followed by dialysis, (2) electrodialysis, (3) dissolution in an aqueous solution of ammonia or amine of metal silicon, (4) peptization of silica gel, (5) removal of Na from water glass using an ion-exchange resin. Among them, the most general method for producing the silica sol is the method using removal of Na from water glass using an ion-exchange resin. To the silica sol produced by this method, a stabilizer such as LiOH, NaOH, or KOH is added for enhancing the stability under high-concentration conditions. Accordingly, the stable pH region of the silica sol is generally approximately 8 to 10. For maintaining the stable dispersed state of the silica sol, it is required that the electrical charges of the silica particles in the sol should repel one another. Therefore, $OH^-$ is adsorbed onto the surface of the silica particles by the addition of the stabilizer as described above and allowed to exhibit stabilizing effect based on its negative charge, preventing gelation. However, it is known that since the addition of excessive alkali (alkali metal ions in the stabilizer) results in adsorbed alkali ions and decreased negative charges, the silica sol becomes unstable. In recent years, many silica sols that have these original properties of silica sol and can be used in various applications have become commercially available. Examples thereof include SNOWTEX series available from NISSAN CHEMICAL INDUSTRIES, LTD., including: SNOWTEX 30 having a silica sol concentration of 30%; SNOWTEX C for use in applications that might further cause gelation; SNOWTEX N intended to eliminate the risk of residual alkali, by virtue of a volatile weak base used as a stabilizer; and SNOWTEX O suitable for applications that require use under acidic conditions (all are trade names; reference: SHOKUBAI KOGAKU KOZA (Lectures on Catalyst Engineering in English) 10, GENSO-BETSU SHOKUBAI BINRAN (Element-By-Element Catalyst Handbook in English), published in Feb. 25, 1967).

The silica particles in the silica sol obtained by the production method are classified into acidic and alkali types in terms of the surface. However, few nitric acid ions are present in the silica sol of either type. For example, hydrogen ions are mainly used as a stabilizer for the acidic type, whereas sodium ions or ammonium ions are used as a stabilizer for the alkali type. $SO_4^{2-}$, $Cl^-$, or the like is used as a counter anion for the acidic type, and $OH^-$ is generally used as a counter anion for the alkali type.

For obtaining silica sol of either acidic or alkali type described above with a nitric acid ion mass fraction of 0 to 270 mass ppm based on the mass of silica, it is preferable that the amount of nitric acid ions should be adjusted to 0 to 270 mass ppm based on silica by the addition of nitric acid or nitrate (e.g., ammonium nitrate) in the neutralization of an aqueous water glass solution with sulfuric acid or hydrochloric acid, which is the general method for producing the silica sol. Moreover, after the neutralization with sulfuric acid or hydrochloric acid, the nitric acid ions may be replaced by anions in the aqueous water glass solution by ion exchange. Alternatively, the amount of nitric acid ions may be adjusted by adding nitric acid ions to the established silica sol using a pipette or the like. The source of nitric acid may be nitric acid as well as a salt such as ammonium nitrate.

The raw material for the silica carrier may be the silica sol alone. Alternatively, a silica powder can be substituted for a portion of the silica sol. Use of the silica powder as a raw material for the silica carrier can be expected to produce catalytic activity and/or effect such as improvement in the yield of the product of interest. By contrast, when the catalyst is prepared using only a silica powder without the use of silica sol, the wear resistance of the catalyst is significantly reduced. In the present specification, the term "silica powder" refers to fine particles of $SiO_2$ in the form of a solid. If the silica has too large a primary particle size, the obtained catalyst tends to be fragile. Thus, a silica powder of nanometer in size is preferable. It is preferable that the silica powder should be produced by a high-temperature method, from the viewpoint of the high purity of silica contained therein, etc. Specific examples of the preferable silica powder include Aerosil 200 (trade name) manufactured by Nippon Aerosil Co., Ltd.

It is preferable that the silica powder should be dispersed in water in advance, from the viewpoint of facilitating addition to slurry and mixing. The method for dispersing the silica powder in water is not particularly limited, and the silica powder can be dispersed by using a general homogenizer, homomixer, or ultrasonic vibrator, and the like alone or in combination.

When the silica sol and the silica powder are used in combination as raw materials for the silica carrier, it is preferable that the silica powder should account for 20 to 80% by mass of the total amount of the silica sol and the silica powder. A catalyst having sufficient wear resistance and catalytic activity can be prepared more easily by adjusting the proportion of the silica powder to this range than by adjusting it to other ranges. It is not required that the silica powder should contain a nitric acid ion. It is not required that the concentration of nitric acid ions contained in the silica powder should be controlled, even when the nitric acid ion concentration in the silica sol is adjusted to 10 to 270 mass ppm based on $SiO_2$ for the purpose of enhancing the yield and/or physical strength of the product of interest.

The raw material preparation step will be described by taking, as an example, the preparation of a raw material preparation containing a Mo compound, a V compound, a Nb compound, Te and/or Sb compound(s) (hereinafter, referred to as a "compound represented by X"), and a compound represented by Z with water as a solvent and/or a dispersion medium. First, the Mo compound, the V compound, the compound represented by X, and the compound represented by Z are added to water, and this solution is heated to prepare an aqueous mixed solution (A). It is preferable that the heating temperature and time for preparing the aqueous mixed solution (A) should be set to ranges that give a state in which each raw material can be dissolved and/or dispersed fully. From such a viewpoint, the heating temperature is preferably 70 to 100° C., and the heating time is preferably 30 minutes to 5 hours. Likewise, the number of revolutions in stirring during heating can be adjusted to the appropriate number of revolutions at which each raw material is easily dissolved and/or dispersed. When the raw materials are metal salts, it is preferable that the stirred state should be maintained during the preparation of the aqueous mixed solution (A), from the viewpoint of fully dissolving the metal salts. In this case, the atmosphere in the container may be an air atmosphere and can also be set to a nitrogen atmosphere from the viewpoint of adjusting the oxidation number of the obtained oxide catalyst. Likewise, hydrogen peroxide can be added, if necessary, in an amount suitable for the aqueous mixed solution (A), from the viewpoint of adjusting the oxidation number. For example, when antimony is used as the element X, it is preferable that hydrogen peroxide should be added to the aqueous mixed solution (A) or to a solution containing the components for the aqueous mixed solution (A) during its preparation. $H_2O_2$/Sb (molar ratio) is preferably 0.01 to 5, more preferably 0.5 to 3, even more preferably 1 to 2.5, from the viewpoint of adjusting the oxidation number of the obtained oxide catalyst to the preferable range.

It is preferable that the heating temperature and time after the addition of hydrogen peroxide to the aqueous mixed solution (A) should be set to ranges that allow liquid-phase oxidation reaction with hydrogen peroxide to sufficiently proceed. From such a viewpoint, the heating temperature is preferably 30° C. to 70° C., and the heating time is preferably 5 minutes to 4 hours. Likewise, the number of revolutions in stirring during heating can be adjusted to the appropriate number of revolutions at which liquid-phase oxidation reaction with hydrogen peroxide is facilitated. It is preferable that the stirred state should be maintained during heating, from the viewpoint of allowing liquid-phase oxidation reaction with hydrogen peroxide to sufficiently proceed.

Subsequently, the Nb compound and dicarboxylic acid are separately added into water, and these solutions are heated with stirring to prepare a mixed solution ($B_0$). Examples of the dicarboxylic acid include oxalic acid [$(COOH)_2$]. It is preferable that hydrogen peroxide should then be added to the mixed solution ($B_0$) to prepare an aqueous mixed solution (C). In this case, $H_2O_2$/Nb (molar ratio) is preferably 0.5 to 20, more preferably 1 to 10, from the viewpoint of, for example, stabilizing the dissolved state by complexation with the Nb compound, appropriately adjusting the redox state of the catalyst-constituting element, and achieving the appropriate catalyst performance of the obtained catalyst.

Next, the aqueous mixed solution (A) and the aqueous mixed solution (C) are mixed at a preferable mixing ratio according to the composition of interest to obtain an aqueous mixed solution (D). The obtained aqueous mixed solution (D) is aged, as appropriate, to obtain a raw material preparation in the form of slurry.

The aging of the aqueous mixed solution (D) means that the aqueous mixed solution (D) is left standing or stirred for the predetermined time. The industrial production of the oxide catalyst may require time until the completion of spray-drying of the whole aqueous mixed solution (D) after spray-drying of a portion of the mixed solution, because the treatment speed of a spray dryer described later is rate-limiting. During this time, the aging of the non-spray-dried portion of the mixed solution can be continued. Specifically, the aging time includes not only an aging time before spray-drying but also a time from the initiation to the completion of spray-drying.

The aging time is preferably between 90 minutes and 50 hours inclusive, more preferably between 90 minutes and 6 hours inclusive, from the viewpoint of, for example, improving the catalyst performance of the obtained complex oxide. If the aging time is shorter than 90 minutes or longer than 50 hours, an aqueous mixed solution (IV) having a preferable redox state (potential) is difficult to form. As a result, the catalyst performance of the obtained complex oxide tends to be reduced. In this context, the industrial production of the oxide catalyst usually requires time until the completion of spray-drying of the whole aqueous mixed solution (IV) after spray-drying of a portion of the mixed solution, because the treatment speed of a spray dryer is usually rate-limiting. During this time, the aging of the non-spray-dried portion of the aqueous mixed solution is continued. Thus, the aging time includes not only an aging time before drying in the step (c) described later but also a time from the initiation to the completion of drying.

The aging temperature is preferably 25° C. or higher from the viewpoint of preventing the condensation of the Mo component or the deposition of V. Moreover, the aging temperature is preferably 65° C. or lower from the viewpoint of preventing the complex containing Nb and hydrogen peroxide from being hydrolyzed too much to thereby form slurry in a preferable form. Thus, the aging temperature is preferably between 25° C. and 65° C. inclusive, more preferably between 30° C. and 60° C. inclusive.

It is preferable that the ambient atmosphere for the aqueous mixed solution (D) during aging, for example, the atmosphere in the container for aging the aqueous mixed solution (D) therein, should have a sufficient oxygen concentration. The atmosphere having a sufficient oxygen concentration facilitates substantial changes in the aqueous mixed solution (D). The oxygen concentration of the gas-phase portion in the ambient atmosphere is more preferably 1% by volume or higher. For example, it is preferable that the aqueous mixed solution (D) should be aged in an air atmosphere.

The oxygen concentration of the gas phase can be measured by a general method, for example, using a zirconia-type oxygen concentration meter. The site at which the oxygen concentration of the gas phase is measured is preferably the proximity to the interface between the aqueous mixed solution (D) and the gas phase, from the viewpoint of determining the correct oxygen concentration. For example, it is preferable that the oxygen concentration of the gas phase should be measured 3 times within 1 minute at the same point, and an arithmetic mean of the results of 3 measurements should be defined as the oxygen concentration of the gas phase.

Examples of a diluent gas for reducing the oxygen concentration of the gas phase include, but not particularly limited to, gases such as nitrogen, helium, argon, carbon dioxide, and water vapor. The nitrogen gas is industrially preferable. Moreover, a gas used for increasing the oxygen concentration of the gas phase is preferably, for example, pure oxygen or air having a high oxygen concentration.

The aging probably causes some change in the redox state of the components contained in the aqueous mixed solution (D). This occurrence of some change is also suggested from changes in the color of the aqueous mixed solution (D), changes in redox potential, etc., during aging. As a result, the performance of the obtained oxide catalyst also differs depending on the presence or absence of aging for a time between 90 minutes and 50 hours inclusive in an atmosphere having an oxygen concentration of 1 to 25% by volume. Specifically, although the morphological change of the components in the solution during aging is exceedingly difficult to accurately identify, it can be assumed, by producing oxide catalysts differing in aging time and evaluating their performance, that the aging time that has offered an oxide catalyst having favorable performance is preferable, during which slurry has been formed in some preferable form.

The potential of the aqueous mixed solution (C) (e.g., 600 mV/AgCl, when the dicarboxylic acid in the aqueous mixed solution (C) is oxalic acid) is predominant in the redox potential of the aqueous mixed solution (D). The peroxide of dicarboxylic acid and Nb contained in the aqueous mixed solution (C) probably causes some redox reaction with the other metal components, reducing the potential over time. The redox potential of the aqueous mixed solution (D) is preferably 450 to 530 mV/AgCl, more preferably 470 to 510 mV/AgCl.

The oxygen concentration in the ambient atmosphere for the aqueous mixed solution (D) during aging is preferably 1% by volume or higher from the viewpoint of preventing redox reaction (which influences changes in the redox state of the components contained in the aqueous mixed solution (D)) from proceeding too slow to thereby prevent the redox state from being an over-reduction state at the slurry stage. On the other hand, the oxygen concentration in the ambient atmosphere for the aqueous mixed solution (D) during aging is preferably 25% by volume or lower from the viewpoint of preventing the slurry from being over-oxidized due to redox reaction proceeding too much. In any case, it is required that the oxygen concentration should be maintained within the appropriate range, because oxygen in the gas phase influences the redox state of the slurry. The range is more preferably 5 to 23% by volume, even more preferably 10 to 20% by volume.

During aging, water may evaporate such that the aqueous mixed solution (D) is concentrated. However, although aging in the open system inevitably causes such water evaporation, it is preferable that the aging should be performed in an atmosphere having an oxygen concentration of 1 to 25% by volume, from the viewpoint of improving catalyst performance.

For stirring during aging, it is preferable that liquid density, the amount of the raw material preparation, the number of revolutions of a stirring blade, etc. should be controlled, from the viewpoint of preventing the gelation of the slurry and from the viewpoint of adjusting the viscosity of the obtained slurry to an appropriate state. Deformation in the obtained particle or depressions in the catalyst particle in a spray-drying step described later can be prevented by maintaining the viscosity of the slurry at a moderately high level, compared with when the slurry has too low viscosity. Alternatively, the gelation of the raw material preparation resulting in clogging in a pipe (which makes a dry powder difficult to obtain) or reduced catalyst performance can be prevented by maintaining the viscosity of the slurry at a moderately low level, compared with when the slurry has too high viscosity. The moderately viscous slurry can be obtained by controlling liquid density, the amount of the raw material preparation, the number of revolutions of a stirring blade, etc.

The stirring can be performed using, for example, a general stirring blade or impeller such as a multi-blade, an anchor blade, a helical axis impeller, a helical ribbon impeller, or a stirring blade for low viscous solutions such as a propeller, a disc turbine, a fan turbine, a fan turbine with curved blades, a turbine with herringbone gears, or a turbine with angled blades.

A power (hereinafter, referred to as "Pv") imparted by a stirring blade in a stirring apparatus to the raw material preparation per unit volume in an apparatus for obtaining the raw material preparation is calculated according to the formula shown below (formula A). Pv is preferably 0.005 to 300 kW/m$^3$, more preferably 0.01 to 280 kW/m$^3$, even more preferably 0.1 to 250 kW/m$^3$. The gelation of the raw material preparation resulting in clogging in a pipe (which makes a dry powder difficult to obtain) or reduced catalyst performance can be more prevented by stirring the raw material preparation at a stirring power Pv of 0.005 kW/m$^3$ or more. Alternatively, depressions in the catalyst particle after spray-drying can be prevented by stirring the raw material preparation at a stirring power Pv of 300 kW/m$^3$ or less. The presence of depressions adversely affects the strength of the catalyst.

This Pv value can be controlled by adjusting liquid density, the amount of the raw material preparation, the number of revolutions of a stirring blade, etc.

Pv is calculated according to the following formula (formula A):

$$Pv = Np \times \rho \times n^3 \times d^5 N \qquad \text{(formula A)}$$

wherein Np represents a power number which is a dimensionless number as to the power necessary for stirring; ρ represents liquid density (kg/m$^3$); n represents the number of revolutions (s$^{-1}$) of a stirring blade; d represents the diameter (m) of the stirring blade; and V represents the amount (m$^3$) of the raw material preparation.

Np can be calculated using the following formula (formula B1):

[Equation 1]

$$Np = \frac{A}{Re} + B\left(\frac{10^3 + 1.2Re^{0.66}}{10^3 + 3.2Re^{0.66}}\right)^p \times \left(\frac{Z}{D}\right)^{(0.35+b/D)} \times (\sin\theta)^{1.2} \qquad \text{(Formula B1)}$$

wherein $$A = 14 + (b/D)\{670(d/D-0.6)^2 + 185\} \qquad \text{(Formula B2)}$$

$$B = 10^{\{1.3-4(b/D-0.5)^2-1.14(d/D)\}} \qquad \text{(Formula B3)}$$

$$p = 1.1 + 4(b/D) - 2.5(d/D-0.5)^2 - 7(b/D)^4 \qquad \text{(Formula B4)}$$

$$Re = 10^{4(1-\sin\theta)} \times (25/(b/D) \times (d/D-0.4)^2 + [(b/D)/\{0.11(b/D)-0.0048\}]) \qquad \text{(Formula B5)}$$

In this context, the symbols in the formulas (formulas B1 to B5) are each defined as follows: b represents the width (m) of the stirring blade; d represents the diameter (m) of the stirring blade; D represents the diameter (m) of the stirring tank; Z represents the depth (m) of the liquid; and θ represents the angle (°) of inclination of the stirring blade from the horizontal. Moreover, the viscosity of the obtained raw material preparation at room temperature (25° C.) is preferably 1 to 100 cp, more preferably 2 to 90 cp, even more preferably 2.5 to 80 cp, from the viewpoint of, for example, more preventing the gelation of the raw material preparation resulting in clogging in a pipe (which makes a dry powder difficult to obtain) or reduced catalyst performance, and more preventing depressions in the catalyst particle after spray-drying or deformation in the catalyst particle.

The viscosity of the raw material preparation can be measured by, for example, a measurement method using a commercially available viscometer, or a method which involves determining a pressure drop within a pipe in which the raw material preparation is circulated. For example, when the viscosity of a solution whose gelation gradually proceeds in a stirring-free state is measured, viscosity may change gradually during measurement using the commercially available viscometer. Thus, it is preferable that the viscosity should be measured by the method which involves determining a pressure drop within a pipe in which the raw material preparation is circulated, from the viewpoint of the reproducibility of measurement values.

When the viscosity of the raw material preparation is measured by the method which involves determining a pressure drop within a pipe in which the raw material preparation is circulated, the viscosity can be calculated according to the following formula (formula C1):

[Equation 2]

$$\mu = \frac{9.8 \times \Delta P \times D^2}{32 \times 10^{-3} \times uL} \quad \text{(Formula C1)}$$

wherein ΔP represents a pressure drop (mmH$_2$O) in the pipe; μ represents liquid viscosity (cp) at measurement temperatures; u represents the average rate (m/s) of liquid circulation; L represents the length (m) of the pipe; and D represents the diameter (m) of the pipe.

When the raw material preparation is obtained by mixing a plurality of raw material solutions containing each component dissolved therein, the upper limit of each Pv for preparing each raw material solution is not particularly limited. Likewise, the lower limit of Pv is not particularly limited. However, it is preferable that Pv should be set to equal to or higher than a value that gives a state in which all or the majority of solid particles flow in the apparatus for obtaining the raw material solution, at a distance from the bottom of a tank in the apparatus. For preparing the raw material solutions, stirring may be stopped after dissolution of substantially all the solid particles in each raw material solution. Moreover, an acid and/or an alkali may be added, if necessary, for adjusting the pH of the slurry.

When the oxide catalyst is a silica-supported product, it is preferable that the raw material preparation should be prepared such that it contains silica sol, from the viewpoint of, for example, fully dissolving and/or dispersing the compound containing each catalyst-constituting element, appropriately adjusting the redox state of the catalyst-constituting element, allowing the obtained catalyst particle to have preferable shape and/or strength, and improving the catalyst performance of the obtained complex oxide. The silica sol can be added appropriately thereto. Moreover, a portion of the silica sol can also be replaced by an aqueous silica powder dispersion. The aqueous silica powder dispersion can also be added appropriately thereto.

The raw material preparation step described above can be carried out repetitively according to yields. If W is contained in the raw material preparation obtained through the raw material preparation step (I) in the process for producing the oxide catalyst and in a dry powder obtained through the drying step (II) described later, then b>0 in the formula (1). As a result, W seems to also exist in the region on the central side of the particle of the oxide catalyst, because W introduced in the raw material preparation step (I) is present since the solution state.

(II) Drying Step

The raw material preparation in the form of slurry obtained through the raw material preparation step is dried to obtain a dry powder (dry product). The drying can be performed by a method known in the art and can also be performed, for example, by spray-drying or evaporation to dryness. When a fluidized-bed reaction system is adopted in gas-phase catalytic oxidation reaction or gas-phase catalytic ammoxidation reaction, it is preferred to obtain a dry powder or a catalyst precursor in a microspheric form and therefore adopt spray-drying, from the viewpoint of, for example, obtaining preferable fluidity in a reactor. Atomization in the spray-drying method may be performed using any of a centrifugation system, a two-fluid nozzle system, and a high-pressure nozzle system. Air heated using a steam, an electrical heater, or the like can be used as a heat source for drying. The inlet temperature of a dryer in a spray-drying apparatus is preferably 150 to 300° C. from the viewpoint of, for example, allowing the obtained catalyst particle to have preferable shape and/or strength, and improving the catalyst performance of the obtained complex oxide. Moreover, the outlet temperature of the dryer is preferably 100 to 160° C.

Spray velocity, the solution sending rate of the slurry, the number of revolutions of an atomizer (in the case of the centrifugation system), etc. may be adjusted according to the size of the apparatus such that the particle size of the obtained dry powder falls within a preferable range. Specifically, the average particle size of the dry powder is preferably 5 μm to 200 μm, more preferably 10 to 150 μm.

The average particle size of the dry powder particles is determined by measuring particle size distributions according to JIS R 1629-1997 "Determination of particle size distributions for fine ceramic raw powders by laser diffraction method" and determining an average value thereof based on volume. More specifically, a portion of the dry powder is calcined at 400° C. for 1 hour in air, and the obtained particle is measured as a subject using a laser diffraction/scattering method-based particle size distribution analyzer LS230 manufactured by BECKMAN COULTER, INC.

The reason to measure the average particle size after the "calcination at 400° C. for 1 hour in air" of a portion of the dry powder is that the dry powder is prevented from being dissolved in water. This means that the "calcination at 400° C. for 1 hour in air" is performed mainly for the measurement and is not related to the calcination step described later. It is reasonable to think that the particle size hardly changes between before and after this calcination.

More specifically, the measurement of the average particle size is performed as follows according to the manual included in the laser diffraction/scattering method-based particle size distribution analyzer (trade name "LS230" manufactured by BECKMAN COULTER, INC.): first, background measurement (Run Speed: 60) is performed, and then, 0.2 g of particles is weighed into a screw tube having an appropriate size, to which 10 cc of water is then added. The screw tube is capped (tightly closed) and sufficiently shaken to disperse the particles in water. Ultrasonic waves of 300 W are applied thereto using the apparatus, and again, the screw tube is sufficiently shaken. Then, the application of ultrasonic waves is continued, while the particles dispersed in water are injected to the main body of the apparatus using a pipette such that the particles have an appropriate concentration (Concentration: 10, PIDS: 60). After confirmation that the concentration indication is stable, the application of ultrasonic waves is stopped. The screw tube is left standing for 10 seconds, and then, measurement is started (Measurement Time: 90 seconds). The value of a median diameter in the measurement results is defined as the average particle size.

It is also preferable that a portion of the dry powder obtained through the drying step should be collected, and its absorption or reflection spectra should be measured. The absorption or reflection spectra of the dry powder obtained through the drying step can be measured continuously to thereby predict the performance of the finally obtained oxide catalyst based on the absorption or reflection spectra.

The degree of redox of the oxide catalyst changes due to heating in the drying step, and the performance of the oxide catalyst is influenced by the change. In the drying step comprising spray-drying the raw material preparation to obtain a dry powder, a portion of the dry powder may adhere to and/or accumulate on the inside wall and/or bottom of the apparatus and thereby remain in the apparatus for a long time. In such a case, the degree of redox changes due to unintended heat applied to the dry powder. When calcination is performed in an air atmosphere in the calcination step described later, the degree of redox of the dry powder hardly influences the performance of the obtained catalyst on the precondition that oxidation proceeds by calcination. On the other hand, when calcination is performed in an inert gas atmosphere in the calcination step, the degree of redox of the dry powder tends to influence the performance of the oxide catalyst. Particularly, when the preparation method is optimized in consideration of the degree of redox of the oxide catalyst, catalyst performance tends to be deteriorated, as a matter of course, due to the degree of redox of the dry powder which falls outside the desired range. The color of the dry powder changes with changes in the degree of redox, though the detailed mechanism is unknown. Taking a Mo—V catalyst as an example, the performance of the oxide catalyst tends to be particularly deteriorated as the dry powder is discolored black. This may be because, for example, organic or inorganic components contained in the dry powder are thermally decomposed due to unintended heating, resulting in the reduction of their surrounding metal elements, or causing redox reaction between the metal elements. Thus, the absorption or reflection spectra of the dry powder can be measured and examined for the degree of discoloration to thereby predict the performance of the oxide catalyst.

For these reasons, it is preferable that the spray-drying apparatus should be equipped with, for example, a dry powder accumulation-preventing apparatus such as a vibrator which gives a vibration to the spray-drying apparatus or an air knocker which gives an impact thereto, for the purpose of preventing the accumulation of the dry powder therein. Moreover, it is also preferable that the inside of the apparatus should be washed with water or the like at moderate frequency while spray-drying is temporarily suspended. It is preferable that the measurement of the spectrum should be performed immediately after the drying step in which unintended heating tends to occur.

Operational conditions for the air knocker with which the drying apparatus is equipped can be adjusted arbitrarily depending on the size of the apparatus, the thickness of the wall, or the extent to which the matter adhering thereto is peeled off. Examples of the operational conditions include the impacting strength of the air knocker, impacting frequency, and increase or decrease in the number of air knockers placed therein, and the change of the site at which the air knocker is placed. It is preferable that the impacting strength of the air knocker should be large without deforming or breaking the wall and/or other sites of the drying apparatus even in long-term operation. From this viewpoint, the impacting frequency is preferably once or more in 1 minute, more preferably once or more in 10 seconds. For the number of air knockers placed therein and the site at which the air knocker is placed, it is preferable that: for example, the number of air knockers should be increased for a site at which severe adhesion is observed by interior observation after long-term operation; or a knocker placed at a site almost free from adhesion should be relocated to a site with severe adhesion.

The method for measuring the absorption or reflection spectra is not particularly limited. For example, the absorption or reflection spectra are determined based on the absorbance of the dry powder measured using a UV-visible spectrophotometer. As a result of conducting diligent studies by the present inventors, it has been demonstrated that a dry powder discolored black which gives an oxide catalyst having poor performance has larger absorbance at a wavelength equal to or higher than 500 nm, than that of a dry powder that is not discolored black. Thus, absorbance at any wavelength in a wavelength range equal to or higher than 500 nm, preferably between 500 nm and 800 nm inclusive, can be selected and used as an index in the measurement.

It is preferable that the absorption or reflection spectra of the dry powder should be measured continuously. In this context, the phrase "measured continuously" means that the measurement is performed once or more frequently in 3 months. The spectrum is measured more preferably once a month, even more preferably once a week, particularly preferably once or more frequently per day. The more frequently the measurement is performed, the more greatly the risk of forming large amounts of dry powders having the inappropriate degree of redox can be reduced. Depending on production conditions, the absorption or reflection spectra of the dry powder may hardly change. In such a case, frequent measurement is unnecessary. Thus, the frequency can be set appropriately.

The production process of the present embodiment may optionally comprise the following step (i) of determining conditions for each of the raw material preparation step (I), the drying step (II), and the calcination step (III) described later, according to the absorption or reflection spectra thus measured.

[Step (i)]

In this step, a catalyst more excellent in performance can be obtained efficiently by predicting the performance of the finally obtained oxide catalyst from the measured absorption or reflection spectra and controlling operational conditions in each step based on the predicted performance of the oxide catalyst.

A correlation diagram of the absorption or reflection spectra of dry powders obtained under different drying conditions vs. the performance of oxide catalysts obtained from the dry powders can be used for predicting the performance of the finally obtained oxide catalyst using the measured absorption or reflection spectra. It is preferable that absorbance obtained at a particular wavelength using a UV-visible spectrophotometer should be used as the absorption or reflection spectra of dry powders obtained under different drying conditions, from the viewpoint of obtaining favorable correlation.

The dry powders obtained under different drying conditions are dry powders that can be obtained by changing at least one of the amount of the raw material preparation (aqueous raw material) supplied per unit time, the amount of air supplied per unit time, and the temperature of supplied air in the drying step, or changing the operational conditions or the like of the dry powder accumulation-preventing apparatus or the like attached to the drying apparatus. When atomization is performed using a centrifugation system, these dry powders may also be obtained by changing the number of revolutions of a disc or the diameter of the disc. Moreover, the dry powders may be obtained by heating the dry powders obtained through the drying step, at intentionally varying temperatures and/or for intentionally varying times to thereby discolor the dry powders.

The absorption or reflection spectra of the dry powders obtained under different drying conditions can be measured in the same way as the method described above. Subsequently, the dry powders obtained under different drying conditions are each further calcined under the same conditions, and the obtained oxide catalysts are used to perform the gas-phase catalytic oxidation or catalytic ammoxidation reaction of propane or isobutane, during which catalyst performance is examined. Examples of the catalyst performance to be examined include yields, activity, the degree of conversion, and by-product yields. These factors may be combined.

Next, a correlation diagram is created based on the absorption or reflection spectra of the dry powders obtained under different drying conditions, and the examined catalyst performance. This correlation diagram can be used to predict the performance of the finally obtained oxide catalyst from the measured absorption or reflection spectra of the dry powder.

In the production process of the present embodiment, an oxide catalyst more excellent in performance can be obtained easily by changing operational conditions in each step according to the predicted performance values of the finally obtained oxide catalyst. Industrially, the oxide catalyst excellent in performance can be obtained efficiently by continuously measuring (monitoring) the absorption or reflection spectra of the dry powder and changing the operational conditions according to the absorption or reflection spectra.

In this step (i), operational conditions in at least one of the raw material preparation step (I), the drying step (II), and the calcination step (III) described later are determined according to the monitored absorption or reflection spectra. It is preferable that the operational conditions in the drying step (II) should be determined according to the absorption or reflection spectra, from the viewpoint of easy controllability. Hereinafter, examples of the step of determining the operational conditions (steps (i-1) and (i-2)) will be described.

[Step (i-1)]

The step (i-1) is the step of determining preparation conditions for the raw material preparation step according to the measured absorption or reflection spectra. In this step, preparation conditions that achieve the favorable performance of the finally obtained oxide catalyst are determined using the correlation diagram of the absorption or reflection spectra of dry powders obtained under different drying conditions vs. the performance of oxide catalysts obtained from the dry powders.

In this step, the means of "determining preparation conditions" is not particularly limited. Examples thereof include a method which involves controlling the degree of redox of the catalytic component according to dissolution procedures or mixing procedures for dissolving and/or dispersing the constitutive element compound in an aqueous medium, and a method which involves adding an oxidizing agent or a reducing agent.

[Step (i-2)]

The step (i-2) is the step of determining drying conditions for the drying step according to the measured absorption or reflection spectra. In this step, drying conditions that achieve the favorable performance of the finally obtained oxide catalyst are determined using the correlation diagram of the absorption or reflection spectra of dry powders obtained under different drying conditions vs. the performance of oxide catalysts obtained from the dry powders.

In this step, the means of "determining drying conditions" is not particularly limited. For example, when a spray-drying apparatus is used, examples thereof include a method which involves changing the amount of the raw material preparation supplied per unit time, the amount of air supplied, and the temperature of air per supplied unit time, or the operational conditions or the like of the dry powder accumulation-preventing apparatus or the like attached to the drying apparatus. The method which involves changing the operational conditions of the dry powder accumulation-preventing apparatus is more preferable from the viewpoint of maintaining the performance, physical shape/strength, or the like of the obtained catalyst. When atomization is performed using a centrifugation system, the number of revolutions of a disc or the diameter of the disc may be changed. Moreover, these factors may be combined.

The dry powder can be prepared such that the content of particles having a particle size of 25 μm or smaller is 20% by mass or less, preferably 15% by mass or less, more preferably 10% by mass or less, even more preferably 5% by mass or less, particularly preferably 2% by mass or less. By virtue of the 20% by mass or less content of particles having a particle size of 25 μm or smaller, there is a tendency in the resulting catalyst to achieve prevention of reduction in its performance, and prevention of reduction in the yield of the product of interest in an apparatus used for fluidized-bed reaction.

The reason why catalyst performance is deteriorated is not clear. Presumably, this may be because if the content of particles having a particle size of 25 μm or smaller exceeds 20% by mass, uneven calcination tends to occur in a calcining device (calcination tube) due to reduced fluidity. According to more detailed discussion, dry powder or catalyst precursor particles having a small particle size return into the calcining device, particularly in continuous calcination, and are thus exposed to the calcination atmosphere for a longer time than the desired one. Therefore, there might arise problems such as the inappropriate rate of reduction of catalyst precursors in pre-stage calcination described later, and the decomposition of crystals attributed to excessive calcination in main calcination. Furthermore, if the content of particles having a particle size of 25 μm or smaller exceeds 20% by mass in the dry powder, the resulting catalyst precursor particles is increasingly adhered. Therefore, the performance is deteriorated, presumably because the particles adhered to the wall of the calcining device accumulate thereon, incurring the risk of insufficient heat transfer into the inside thereof or contamination with catalysts derived from particles excessively calcined due to the long-lasting adhesion. In this context, the "catalyst precursor" refers to a compound formed in the course of the calcination step described later. For example, a compound obtained by pre-stage calcination is referred to as the catalyst precursor. For these reasons, a catalyst having performance (e.g., the yield of the product of interest) equivalent to that obtained in batch calcination can be produced stably in catalyst production by continuous calcination using a dry powder prepared to have a 20% by mass or less content of particles having a particle size of 25 μm or smaller, even when catalyst composition is the same between the methods.

Moreover, when the oxide catalyst contains Mo, Sb, and Te, and the like, a low-melting-point compound tends to be formed during calcination. Particles having a particle size of 25 μm or smaller have a larger specific surface area than that of particles having a particle size exceeding 25 μm and therefore seem to be increasingly adhered. If too many particles are adhered, there arise problems, for example, a sufficient calcination temperature cannot be obtained for the catalyst layer, and sufficient yields cannot be secured. Accordingly, it is preferred to create a state in which particles having a particle size of 25 μm or smaller are few in number, i.e., to adjust the content of such particles to 20% by mass or less, at a stage prior to calcination.

The dry powder is prepared such that its average particle size is preferably 5 to 200 μm, more preferably 10 to 150 μm, even more preferably 35 to 70 µm, further preferably 40 to 65 µm, further preferably 42 to 65 µm, particularly preferably 45 to 63 µm, exceedingly preferably 45 to 60 µm. By virtue of the average particle size of 5 µm or larger, there is a tendency in the resulting catalyst to achieve prevention of reduction in fluidity resulting in the reduced yield of the fluidized-bed reaction product of interest, or prevention of a great loss of the amount of the catalyst caused by flying out of a fluidized-bed reactor. By virtue of the average particle size of 200 µm or smaller, there is a tendency in the resulting catalyst to achieve prevention of reduction in oxide catalyst fluidity and in contact efficiency with reaction gas resulting in the reduced yield of the fluidized-bed reaction product of interest.

The rate of reduction of the catalyst precursor can be adjusted to a preferable range in the calcination step described later by adjusting the average particle size of the dry powder to preferably 35 to 70 µm and the content of particles having a particle size of 25 µm or smaller to preferably 20% by mass or less, prior to the calcination step described later. This mechanism is interpreted by the present inventor as follows, though it is not limited thereto.

The dry powder usually contains at least one of root ammonium, an organic acid, and an inorganic acid. When the dry powder is calcined with an inert gas circulated, the catalyst-constituting elements are reduced during the evaporation, decomposition, or the like of the root ammonium, the organic acid, and/or the inorganic acid. The root ammonium evaporates to form an ammonia gas, which reduce the dry powder or catalyst precursor particles from the gas phase. The rate of this reduction varies depending on the calcination time and the calcination temperature, particularly in pre-stage calcination described later. A long calcination time or a high calcination temperature facilitates reduction, leading to the high rate of reduction. If the dry powder is rich in particles having a relatively small particle size (hereinafter, also referred to as "small particles"), typically when the average particle size is smaller than 35 µm or the content of particles having a particle size of 25 µm or smaller exceeds 20% by mass, the dry powder or catalyst precursor particles are entrained in an inert gas or scattered along with the rotation of a calcination tube serving as a calcining device. As a result, many small particles return into the calcination tube and may thus reside in the calcination tube for a time longer than the desired one, making it difficult to obtain the preferable range of the rate of reduction. Moreover, the small particles also seem to be increasingly reduced, because many sites in the surface come in contact with an ammonia gas. On the contrary, if the average particle size of the dry powder exceeds 70 µm, its particles are large and thus have a few sites in the surface that come in contact with an ammonia gas. Thus, such a dry powder is hard to be reduced. As a result, the rate of reduction may become difficult to adjust to the preferable range.

In this context, the content of particles having a particle size of 25 µm or smaller is a value that is determined by calcining a portion of the dry powder at 400° C. for 1 hour in air, sieving 20 g of the obtained particles using a sieve of 25 µm in aperture and 20 cm in diameter upon exposure to a vibrator (e.g., Panabrator (trade name) manufactured by National) for 3 minutes, and measuring the mass of particles passing through the sieve and the mass of particles remaining on the sieve, followed by calculation using the following formula:

(Content (%) of 25 µm or smaller particles)=(Mass of particles passing through the sieve)÷{(Mass of particles passing through the sieve)+(Mass of particles remaining on the sieve)}×100.

The reason to measure the content of particles having a particle size of 25 µm or smaller after the "calcination at 400° C. for 1 hour in air" of a portion of the dry powder is that the dry powder is prevented from being dissolved in water. This means that the "calcination at 400° C. for 1 hour in air" is performed mainly for the measurement and is not related to the calcination step described later. It is reasonable to think that the particle size hardly changes between before and after this calcination. The rate of reduction of the sample obtained by this calcination may be different from that of the other dry powders. Usually, this sample whose amount is very small hardly influences the performance of the whole catalyst even if the sample is subjected to the calcination step described later, or not. The subject in the measurement of the average particle size may be or may not be the dry powder. If necessary, the average particle size of the calcined catalyst precursor may be measured.

Examples of the method for preparing particles having a 20% by mass or less content of particles having a particle size of 25 µm or smaller, and an average particle size of 35 to 70 µm include a method which involves adjustment of spray-drying conditions, for example, the number of revolutions of an atomizer, the spray-drying temperature, or the amount of the raw material mixed solution supplied, and a method which involves classification of the dry powder. The classification method is not particularly limited. For example, a method using a general apparatus such as a centrifugal classifier, an air classifier, a gravitational classifier, an inertial classifier, a sieve, and a cyclone can be adopted. Of dry and wet types, the dry-type classifier can be used preferably from the viewpoint of, for example, preventing the elution of the catalyst-constituting elements into a solvent, and eliminating adverse effect on catalyst performance. The classifier is adjusted to conditions such that the recovery rate of the dry powder in classification is preferably 75% by mass or more, more preferably 80% by mass or more, from the viewpoint of increasing the yield of the catalyst. Alternatively, it is preferable that an apparatus that satisfies the conditions should be selected for use.

(III) Calcination Step

The calcination step (III) may comprise the step of calcining the dry powder obtained through the drying step, in the presence of a compound containing W in the form of a solid (hereinafter, referred to as a "W-containing compound solid") to obtain a pre-stage calcined powder or a mainly calcined powder (hereinafter, also referred to as a step (b-1)). Alternatively, the calcination step (III) may comprise the step of calcining the dry powder and further calcining the obtained pre-stage calcined powder in the presence of a W-containing compound solid to obtain a mainly calcined powder (hereinafter, also referred to as a step (b-2)). Furthermore, the calcination step (III) may optionally comprise the step of further calcining the mainly calcined powder in the presence of a W-containing compound solid (hereinafter, also referred to as a step (b-3)). In this way, the oxide catalyst is obtained. Specifically, in the calcination step, the calcination may be performed at multiple stages by changing conditions (e.g., temperature) at each stage as described later. Alternatively, the calcination may be performed at a single stage under constant conditions. Moreover, the timing at which the W-containing compound solid coexists with the dry powder can be selected appropriately. The calcination conditions and the timing at which the W-containing compound solid coexists therewith may be set each independently and can be selected each independently from the viewpoint of the desired performance of the oxide catalyst, convenient production steps, etc. Hereinafter, a calcination method (a) for the dry powder will first be described without making a mention about the presence or absence of the W-containing compound solid. Subsequently, the steps (b-1), (b-2), and (b-3) will be described separately as a calcination method (b) performed in the presence of the W-containing compound solid.

((a) Calcination Method for Dry Powder)

For example, a rotary kiln can be used as a calcination apparatus. The shape of the calcining device is not particularly limited and is preferably a tubular form (calcination tube) considering that continuous calcination can be carried out. Particularly, a cylindrical form is preferable. The heating method is preferably an external heating process from the viewpoint of, for example, easily adjusting the calcination temperature to the preferable pattern of temperature rise. An electric furnace can be used preferably. The size and material, and the like of the calcination tube can be selected appropriately according to the calcination conditions or yields. The inside diameter of the calcination tube is preferably 70 to 2000 mm, more preferably 100 to 1700 mm, from the viewpoint of, for example, preventing uneven calcination temperature distribution in the catalyst layer, and adjusting the calcination time and yields to appropriate values. Moreover, the length of the calcination tube is preferably 200 to 10000 mm, more preferably 800 to 8000 mm, from the viewpoint of, for example, minimizing the residence time of the dry powder and catalyst precursor particles in the calcination tube, i.e., calcination time distribution, preventing deformation in the calcination tube, and adjusting the calcination time and yields to appropriate values. When an impact is given to the calcination tube, its wall thickness is preferably 2 mm or larger, more preferably 4 mm or larger, from the viewpoint of maintaining a thickness large enough to prevent the wall from being broken due to the impact. Moreover, the wall thickness is preferably 100 mm or smaller, more preferably 50 mm or smaller, from the viewpoint of sufficiently transferring the impact to the inside of the calcination tube. Moreover, it is preferable that the calcination tube should have an inclination toward the powder flow direction and have an outlet smaller in height than the powder inlet, from the viewpoint of, for example, preventing uneven calcination temperature distribution and calcination time distribution in the catalyst layer, and adjusting the calcination time and catalyst yields to appropriate values. Moreover, from this viewpoint, an angle θ of inclination from the horizontal is preferably 0°<θ<80°, more preferably 1°≤θ≤40°.

The material of the calcining device is not particularly limited as long as it preferably has heat resistance and is strong enough to prevent the calcining device from being broken due to the impact. For example, those made of SUS can be used preferably.

A weir plate having, in the central portion, a hole through which the powder passes may be disposed perpendicular (or almost perpendicular) to powder flow in the calcination tube such that the calcination tube is partitioned into two or more areas. The residence time of the powder in the calcination tube can be secured easily by the placement of the weir plate. The number of weir plates may be one or two or more. The material of the weir plate is preferably a metal from the viewpoint of improving durability to withstand the calcination atmosphere and heat resistance. The same material as that of the calcination tube can be used preferably. The height of the weir plate can be adjusted according to the residence time to be secured. For example, when the dry powder is supplied at a rate of 250 g/hr using a rotary kiln having a calcination tube made of SUS with an inside diameter of 150 mm and a length of 1150 mm, the height of the weir plate is preferably 5 to 50 mm, more preferably 10 to 40 mm, even more preferably 13 to 35 mm. The thickness of the weir plate is not particularly limited and is preferably adjusted according to the size of the calcination tube. For example, for a rotary kiln having a calcination tube made of SUS with an inside diameter of 150 mm and a length of 1150 mm, the thickness of the weir plate is preferably between 0.3 mm and 30 mm inclusive, more preferably 0.5 mm and 15 mm inclusive.

For preventing breaking, cracking, or the like in the dry powder and for uniform calcination, it is preferable that the calcination should be performed with the calcination tube rotating about the longitudinal axis. The rotational speed of the calcination tube is preferably 0.1 to 30 rpm, more preferably 0.5 to 20 rpm, even more preferably 1 to 10 rpm.

For the calcination of the dry powder, it is preferable that the dry powder should be heated at a temperature that starts at a temperature lower than 400° C. and is raised therefrom continuously or gradually to a temperature within the range of 550 to 800° C., from the viewpoint of, for example, achieving the preferable redox state of the obtained catalyst, and improving catalyst performance.

The calcination may be performed in an air atmosphere or under air circulation. It is preferable that at least a portion of the calcination should be carried out while an inert gas (e.g., nitrogen) substantially free from oxygen is circulated, from the viewpoint of, for example, easily adjusting the catalyst to the preferable redox state.

When batch calcination is performed, the amount of the inert gas supplied is preferably 50 N/liter/hr or more, more preferably 50 to 5000 N/liter/hr, even more preferably 50 to 3000 N/liter/hr, per kg of the dry powder, from the viewpoint of adjusting the catalyst to the preferable redox state. In this context, the unit "N/liter" means a liter measured under standard temperature and pressure conditions, i.e., at 0° C. and a pressure of 1 atmosphere.

When continuous calcination is performed, the amount of the inert gas supplied is preferably 50 N/liter/hr or more, more preferably 50 to 5000 N/liter/hr, even more preferably 50 to 3000 N/liter/hr, per kg of the dry powder, from the viewpoint of adjusting the catalyst to the preferable redox state. In this case, the form of the contact between the inert gas and the dry powder may be countercurrent contact or may be co-current contact. The countercurrent contact is preferable in consideration of gas components generated from the dry powder, and air that may be mixed in a trace amount into the dry powder. Particularly, when the method which involves adding hydrogen peroxide to the aqueous mixed solution (A) is adopted in the raw material preparation step and molybdenum and vanadium are oxidized up to almost the highest oxidation number to obtain the raw material preparation, it is preferable that the dry powder should be calcined while an inert gas (e.g., nitrogen) substantially free from oxygen is circulated.

The dry powder may usually contain root ammonium, an organic acid, an inorganic acid, and the like, in addition to water.

When the dry powder is calcined while an inert gas substantially free from oxygen is circulated, the catalyst-constituting elements contained in the dry powder and the catalyst precursor are reduced during the evaporation, decomposition, or the like thereof.

When the catalyst-constituting elements in the dry powder have almost the highest oxidation number, only reduction may be carried out in the calcination step in order to adjust the rate of reduction of the oxide catalyst to the desired range. Thus, this approach is industrially convenient.

On the other hand, an oxidizing component or a reducing component may be added, as described later, into the calcination atmosphere such that the rate of reduction is adjusted to the desired range. It is preferable that the calcination should be carried out such that the obtained oxide catalyst has a rate of reduction of 8 to 12% and a specific surface area of 5 to 30 m$^2$/g. By virtue of the catalyst specific surface area of 5 to 30 m$^2$/g, the effect of producing further sufficient activity, more preventing degradation, and also further enhancing yields is exerted. Moreover, the effect brought about by the addition of the molybdenum compound for maintaining yields during oxidation reaction or ammoxidation reaction is exhibited more sufficiently. In addition, abrupt degradation is not observed. Thus, the amount of the molybdenum compound added and the frequency of its addition can be reduced. The reason for this is not clear. Presumably, this is because if the specific surface area is smaller than 5 m$^2$/g, the effect brought about by the addition of the molybdenum compound is hardly exerted due to the small active surface of the active species responsible for the reaction. Moreover, if the specific surface area is larger than 30 m$^2$/g, the active species has a large active surface. However, in this case, molybdenum is presumed to escape rapidly from the active surface. The rate of reduction of the oxide catalyst or the catalyst precursor is calculated according to the following formula (6):

$$\text{Rate of reduction (\%)} = ((n_0 - n)/n_0) \times 100 \quad (6)$$

wherein n represents the number of oxygen atoms that satisfies the valences of constitutive elements other than oxygen in the oxide catalyst or the catalyst precursor; and $n_0$ represents the number of oxygen atoms required for the constitutive elements other than oxygen in the oxide catalyst or the catalyst precursor to have their respective highest oxidation numbers.

For determining the rate of reduction, the value of $(n_0-n)$ in the formula (6) is obtained by subjecting the sample to redox titration with $KMnO_4$. Moreover, the value of $(n_0-n)$ can be determined by redox titration both for the catalyst precursor before the completion of calcination and for the oxide catalyst after the completion of calcination. However, the measurement by redox titration differs in measurement conditions between the catalyst precursor before the completion of calcination and the catalyst after the completion of calcination. Hereinafter, one example of the measurement method will be shown for each of the catalyst precursor before the completion of calcination and the catalyst after the completion of calcination.

For the catalyst precursor before the completion of calcination, the rate of reduction is measured, for example, as follows:

First, approximately 200 mg of the sample is precisely weighed into a beaker. An aqueous solution of $KMnO_4$ having a known concentration is added thereto in an excessive amount. Subsequently, 150 mL of pure water (70° C.) and 2 mL of 1:1 sulfuric acid (i.e., an aqueous sulfuric acid solution obtained by mixing concentrated sulfuric acid and water at a volume ratio of 1/1) are added into the beaker. Then, the opening of the beaker is covered with watch glass, and the solution in the beaker is stirred for 1 hour in a hot water bath of 70° C.±2° C. to oxidize the sample. Since an excess of $KMnO_4$ is present therein, the color of the solution is confirmed to be purple due to the presence of unreacted $KMnO_4$ in the solution. Next, after the completion of oxidation, the solution is filtered through a filter paper, and the whole amount of the filtrate is collected. Subsequently, an aqueous solution of sodium oxalate ($Na_2C_2O_4$) having a known concentration is added in an excessive amount compared to the amount of $KMnO_4$ present in the filtrate. Then, the solution is heated to a temperature of 70° C. with stirring. The solution is confirmed to be colorless and clear, and 2 mL of 1:1 sulfuric acid is added thereto. Furthermore, stirring is continued with the solution temperature kept at 70° C.±2° C., followed by titration with an aqueous solution of $KMnO_4$ having a known concentration. The endpoint is defined as a point in time when the color of the solution becomes slightly pale pink due to the titration with $KMnO_4$ and this color continues for approximately 30 seconds. The amount of $KMnO_4$ consumed in the sample oxidation is determined from the whole amount of $KMnO_4$ and the whole amount of $Na_2C_2O_4$. From this amount of $KMnO_4$, the value of $(n_0-n)$ is calculated, and the rate of reduction is determined based thereon.

For the oxide catalyst after the completion of calcination, the rate of reduction is measured, for example, as follows:

First, approximately 200 mg of the catalyst ground using a mortar made of agate is precisely weighed into a beaker. 150 mL of pure water (95° C.) and 4 mL of 1:1 sulfuric acid (i.e., an aqueous sulfuric acid solution obtained by mixing concentrated sulfuric acid and water at a volume ratio of 1/1) are added thereto. Subsequently, the solution is stirred with its temperature kept at 95° C.±2° C., followed by titration with an aqueous solution of $KMnO_4$ having a known concentration. In this titration, $KMnO_4$ is gradually added dropwise in small portions such that the color of the solution temporarily becomes purple due to the dropwise addition of $KMnO_4$ and however, this purple color does not last for 30 seconds or longer. Moreover, the amount of the solution is decreased as water evaporates. Thus, pure water (95° C.) is added thereto on an as needed basis such that the amount of the solution remains constant. The endpoint is defined as a point in time when the color of the solution becomes slightly pale pink due to the titration with $KMnO_4$ and this color continues for approximately 30 seconds. Then, the amount of $KMnO_4$ consumed in the sample oxidation is determined. From this amount of $KMnO_4$, the value of $(n_0-n)$ is calculated, and the rate of reduction is determined based thereon.

Moreover, in addition to these measurement methods, the following measurement can also be performed both for the catalyst precursor before the completion of calcination and for the oxide catalyst after the completion of calcination:

Specifically, the sample is completely oxidized with oxygen by heating to a temperature higher than the calcination temperature (at which the catalyst precursor or the catalyst is calcined) in an oxygen-containing atmosphere on the condition that the sample-constituting elements do not evaporate or escape. The increased mass (the amount of oxygen bonded thereto) is determined. From this amount, the value of $(n_0-n)$ is determined, and the rate of reduction is determined based thereon.

For the calcination method for the dry powder, it is specifically preferable that: the dry powder should be calcined under calcination conditions in which the dry powder is heated at a temperature that starts at a temperature lower than 400° C. and is raised therefrom continuously or gradually to a temperature within the range of 550 to 700° C.; and the calcination conditions should be adjusted such that the rate of reduction of the catalyst precursor during calcination is 8 to 12% when the heating temperature reaches 400° C.

The rate of reduction of the oxide catalyst is generally influenced by the amount of organic matter such as oxalic acid contained in the dry powder, the amount of root ammonium derived from an ammonium salt as a raw material, the rate of temperature rise at the start of calcination, and the amount of an inert gas (in the case of calcination in an inert gas atmosphere) or the calcination temperature and time (in the case of calcination in an air atmosphere).

Examples of the method for setting the rate of reduction of the oxide catalyst to 8 to 12% include a method which involves raising a temperature starting at a temperature lower than 400° C. for calcination to decompose root oxalic acid, root ammonium, and the like, in the dry powder and thereby almost complete gas generation such that the rate of reduction of the catalyst precursor during calcination is 8 to 12% when the heating temperature reaches 400° C.

The specific surface area of the catalyst is influenced by the final calcination (heating) temperature and time, and the amount of the catalyst supported on the carrier such as silica (in the case of the carrier-supported catalyst), and particularly largely influenced by the rate of reduction when the heating temperature reaches 400° C., and the final calcination temperature. From such a viewpoint, the final calcination temperature is preferably 550° C. to 700° C. At this temperature, the calcination time is preferably 0.5 hours to 20 hours. The higher the final calcination temperature is or the longer the calcination time is, the smaller the resulting specific surface area tends to be.

Moreover, by virtue of the rate of reduction that falls within the ranges of 8 to 12% when the heating temperature reaches 400° C., there is a tendency in the resulting catalyst to achieve prevention of excessive decrease or increase in its specific surface area.

For example, for setting the specific surface area of the catalyst to 5 to 30 m$^2$/g, it is preferable that: the rate of reduction should fall within the ranges of 8 to 12% when the heating temperature reaches 400° C.; and the final calcination temperature should be set to 550° C. to 700° C.

The calcination may be carried out at a single stage under constant conditions. For efficiently obtaining the oxide catalyst having the rate of reduction of 8 to 12% and a specific surface area of 5 to 30 m$^2$/g, it is preferable that the calcination step should comprise pre-stage calcination and subsequent main calcination. In this context, the calcination temperature in pre-stage calcination is preferably a temperature lower than the calcination temperature in main calcination. More specifically, it is preferable that the pre-stage calcination should be performed in a temperature range of 250 to 400° C., and the main calcination should be performed in a temperature range of 550 to 700° C. A pre-stage calcined powder is obtained by this pre-stage calcination, while a mainly calcined powder is obtained by the main calcination.

The main calcination may be performed continuously from pre-stage calcination, i.e., by directly changing the calcination temperature in pre-stage calcination to the calcination temperature for the main calcination. Alternatively, the main calcination may be performed by restarting after the completion of pre-stage calcination, i.e., by temporarily decreasing a temperature from the calcination temperature in pre-stage calcination and then raising it to the calcination temperature for the main calcination. Moreover, the pre-stage calcination and the main calcination may each be divided into a plurality of calcination stages differing in calcination conditions.

When the rate of reduction of the catalyst precursor is measured during calcination, the sample may be taken out of the calcination apparatus with the temperature unchanged. However, a sample having a high temperature may be oxidized upon exposure to air to change the rate of reduction. Thus, such a sample is cooled to room temperature and then taken out of the calcination apparatus. The resulting sample may be used as a representative sample.

Examples of the method for controlling, to the desired range, the rate of reduction when the heating temperature reaches 400° C. specifically include a method which involves adjusting the calcination temperature in pre-stage calcination, a method which involves adding an oxidizing component such as oxygen into the atmosphere during calcination, and a method which involves adding a reducing component into the atmosphere during calcination. Moreover, two or more of these methods may be combined.

The method which involves changing the calcination temperature in pre-stage calcination (hereinafter, referred to as a "pre-stage calcination temperature") is an approach of changing the pre-stage calcination temperature to thereby adjust the rate of reduction of the catalyst precursor when the heating temperature reaches 400° C. The rate of reduction is usually decreased by decreasing the pre-stage calcination temperature, and the rate of reduction tends to be increased by raising the pre-stage calcination temperature. Thus, the rate of reduction can be controlled by changing the pre-stage calcination temperature.

The method which involves adding an oxidizing component such as oxygen into the atmosphere during calcination is a method that can be used for reducing the rate of reduction of the catalyst precursor when the heating temperature reaches 400° C. In this context, the calcination in the term "during calcination" may be pre-stage calcination or main calcination, or both.

The oxidizing component added into the atmosphere during calcination is an oxidizing component contained in an inert gas supplied to a calcination apparatus. The amount of the oxidizing component added can be controlled by concentrations in the inert gas supplied to a calcination apparatus. The rate of reduction of the catalyst precursor when the heating temperature reaches 400° C. can be controlled by the addition of this oxidizing component. When the oxidizing component is oxygen, air (or an air-containing inert gas) is supplied to a calcination apparatus in which oxygen in the air can then be used as an oxidizing component.

The method which involves adding a reducing component into the atmosphere during calcination is a method that can be used for increasing the rate of reduction of the catalyst precursor when the heating temperature reaches 400° C. In this context, the calcination in the term "during calcination" may be pre-stage calcination or main calcination, or both.

The reducing component added into the atmosphere during calcination is a reducing component contained in an inert gas supplied to a calcination apparatus. The amount of the reducing component added can be controlled by concentrations in the inert gas supplied to a calcination apparatus. The rate of reduction of the catalyst precursor when the heating temperature reaches 400° C. can be controlled by the addition of this reducing component. For example, ammonia can be used as the reducing component.

When the rate of reduction of the catalyst precursor is not the desired one when the heating temperature reaches 400° C., the total amount of necessary oxidizing or reducing components can be calculated from the difference between the actual rate of reduction and the desired one, and added into the atmosphere during calcination.

The method for performing calcination in an inert gas atmosphere or a preferable oxidative/reductive atmosphere is not particularly limited. It is preferred to use a calcination apparatus having an appropriate sealing structure with which contact with outside air can be blocked sufficiently.

The pre-stage calcination is performed in a pre-stage calcination temperature range of preferably 250° C. to 400° C., more preferably 300° C. to 400° C., preferably under inert gas circulation, from the viewpoint of, for example, easily adjusting the obtained catalyst to the preferable redox state, and achieving improved catalyst performance. It is preferable that the pre-stage calcination temperature should be maintained at a constant temperature in the temperature range of 250° C. to 400° C. However, the temperature may vary in the temperature range of 250° C. to 400° C. or may be raised or decreased moderately. The time for maintaining the heating temperature is preferably 30 minutes or longer, more preferably 3 to 12 hours, from the viewpoint of, for example, easily adjusting the obtained catalyst to the preferable redox state, and achieving improved catalyst performance. The pattern of temperature rise to reach the pre-stage calcination temperature may be a linear pattern of temperature rise or may be an upwardly or downwardly curved pattern of temperature rise. Moreover, the temperature may decreased for a certain time during temperature rise or may be increased and decreased repetitively. Furthermore, endothermic reaction may be caused by the components contained in the dry powder and/or the catalyst precursor in the course of temperature rise, temporarily decreasing the temperature.

The average rate of temperature rise during temperature rise to reach the pre-stage calcination temperature is not particularly limited. It may be, for example, approximately 0.1 to 15° C./min. and is preferably 0.5 to 5° C./min., more preferably 1 to 2° C./min., from the viewpoint of, for example, easily adjusting the obtained catalyst to the preferable redox state, and achieving improved catalyst performance.

The main calcination is performed at a calcination temperature of preferably 550 to 800° C., more preferably 580 to 750° C., even more preferably 600 to 720° C., particularly preferably 620 to 700° C., preferably under inert gas circulation, from the viewpoint of, for example, easily adjusting the obtained catalyst to the preferable specific surface area, sufficiently forming a reactive crystal structure, and achieving improved catalyst performance. It is preferable that the calcination temperature should be maintained at a constant temperature in the temperature range of 550 to 800° C. However, the temperature may vary in the temperature range of 550 to 800° C. or may be raised or decreased moderately. Moreover, the temperature may be decreased temporarily due to endothermic reaction, may be decreased for a certain time during temperature rise, or may be increased and decreased repetitively, as in pre-stage calcination. Moreover, the calcination time (time for maintaining the calcination temperature) in main calcination is preferably 0.5 to 20 hours, more preferably 1 to 15 hours, from the viewpoint of, for example, easily adjusting the obtained catalyst to the preferable specific surface area, sufficiently facilitating the formation of a reactive crystal structure, and achieving improved catalyst performance. The pattern of temperature rise to reach the calcination temperature may be a linear pattern of temperature rise or may be an upwardly or downwardly curved pattern of temperature rise. Moreover, the average rate of temperature rise during temperature rise to reach the calcination temperature is not particularly limited. It may be, for example, 0.1 to 15° C./min. and is preferably 0.3 to 10° C./min., more preferably 0.5 to 8° C./min., from the viewpoint of, for example, easily adjusting the obtained catalyst to the preferable specific surface area, sufficiently facilitating the formation of a reactive crystal structure, and achieving improved catalyst performance.

When the calcination tube is partitioned with a weir plate, the dry powder, the catalyst precursor, or the oxide catalyst (hereinafter, referred to as a "dry powder, etc.") continuously passes through at least 2 areas or areas isolated using preferably 2 to 20, even more preferably 4 to 15 weir plates from the viewpoint of, for example, securing a residence time suitable for the dry powder, etc. in the calcination tube. Temperature control can be performed using one or more controller(s). For obtaining the desired calcination pattern, it is preferable that a heater and a controller should be placed for temperature control in each of these areas isolated with weir plates. For example, 7 weir plates can be placed to longitudinally divide a portion present in a heating furnace in the calcination tube into 8 equal parts. When the calcination tube thus partitioned into 8 areas is used, it is preferable that the set temperature should be controlled using a heater and a controller that are placed in each of these 8 areas such that the temperature of the dry powder, etc. exhibits the desired calcination temperature pattern. For example, when the calcination tube thus partitioned into 8 areas is used, adjustment for obtaining the desired calcination pattern can be performed as follows: for pre-stage calcination, it is preferable that the temperature of a thermocouple inserted into the central part in each area for the dry powder, etc. residing in the calcination tube should be adjusted to area 1: 100 to 300° C., area 2: 150 to 350° C., area 3: 250 to 400° C., area 4: 250 to 400° C., area 5: 300 to 400° C., area 6: 300 to 400° C., area 7: 310 to 400° C., and area 8: 260 to 400° C., more preferably, area 1: 120 to 280° C., area 2: 180 to 330° C., area 3: 250 to 350° C., area 4: 270 to 380° C., area 5: 300 to 380° C., area 6: 300 to 390° C., area 7: 320 to 390° C., and area 8: 260 to 380° C., wherein the areas are numbered, starting at 1, in the order of supply of the dry powder, etc. Likewise, for main calcination, it is preferable that such a temperature should be adjusted to area 1: 350 to 600° C., area 2: 400 to 700° C., area 3: 550 to 700° C., area 4: 550 to 700° C., area 5: 550 to 700° C., area 6: 450 to 680° C., area 7: 450 to 650° C., and area 8: 350 to 600° C., more preferably, area 1: 360 to 560° C., area 2: 450 to 650° C., area 3: 600 to 690° C., area 4: 620 to 690° C., area 5: 580 to 690° C., area 6: 480 to 660° C., area 7: 450 to 630° C., and area 8: 370 to 580° C. wherein the areas are numbered, starting at 1, in the order of supply of the dry powder, etc.

Moreover, the average rate of temperature decrease after the completion of main calcination is preferably 0.001 to 1000° C./min., more preferably 0.005 to 100° C./min., even more preferably 0.01 to 50° C./min., particularly preferably 0.05 to 20° C./min., from the viewpoint of, for example, sufficiently facilitating the formation of a reactive crystal structure, and improving catalyst performance. Moreover, it is also preferable that the temperature should be maintained temporarily at a temperature lower than the main calcination temperature, from the viewpoint of, for example, sufficiently facilitating the formation of a reactive crystal structure, and improving catalyst performance. From this viewpoint, the temperature is maintained at a temperature preferably at least 10° C., more preferably at least 50° C., even more preferably at least 100° C. lower than the main calcination temperature. From this viewpoint, the time for maintaining the temperature is preferably 0.5 hour or longer, more preferably 1 hour or longer, even more preferably 3 hours or longer, particularly preferably 10 hours or longer.

When the main calcination is carried out by restarting after the completion of pre-stage calcination, low-temperature treatment may be performed in the main calcination. Moreover, low-temperature treatment can also be performed after the main calcination. In addition, further calcination may be performed after the low-temperature treatment following the main calcination.

The time required for the low-temperature treatment, i.e., the time required to decrease the temperature of the pre-stage calcined powder and then raise the temperature to reach the calcination temperature of main calcination, can be adjusted appropriately according to the size, wall thickness, and material of the calcining device, catalyst yields, a series of periods of time during the continuous calcination of the pre-stage calcined powder and/or the mainly calcined powder, the rate of adhesion, the amount of particles adhered, etc. For example, when a calcination tube made of SUS with an inside diameter of 500 mm, a length of 4500 mm, and a wall thickness of 20 mm is used, the time required for the low-temperature treatment is preferably within 30 days, more preferably within 15 days, even more preferably within 3 days, particularly preferably within 2 days in a series of periods of time during the continuous calcination of the pre-stage calcined powder and/or the mainly calcined powder, from the viewpoint of, for example, sufficiently peeling off the pre-stage calcined powder and/or the mainly calcined powder adhered to the wall of the calcination tube, stably maintaining the temperature of the oxide layer, and improving the performance of the obtained catalyst. In this context, the temperature of the oxide layer refers to a temperature measured using a thermocouple inserted into the pre-stage calcined powder and/or the mainly calcined powder accumulating in the calcining device. Moreover, for example, when the main calcination is performed at a calcination temperature of 645° C. by supplying the pre-stage calcined powder at a rate of 35 kg/hr with rotation at 6 rpm of a rotary kiln having a calcination tube made of SUS with an inside diameter of 500 mm, a length of 4500 mm, and a wall thickness of 20 mm, the step of decreasing the temperature to 400° C. prior to the main calcination and then raising the temperature to 645° C. can be performed for approximately 1 day. For 1-year continuous calcination, such low-temperature treatment can be carried out once a month to thereby stably perform calcination with the temperature of the oxide layer maintained.

The mainly calcined powder obtained by main calcination may be used as an oxide catalyst in itself or can further be calcined in the presence of a W-containing compound solid, as described later, to obtain an oxide catalyst that can improve the yield of the compound of interest. When the calcination step is performed at a single stage, the powder obtained by this calcination at a single stage is used as a mainly calcined powder.

Moreover, the effect of cracking masses adhered to the calcining device tends to be enhanced by applying an impact to the calcining device in the calcination step. When the low-temperature treatment is carried out, it is preferable that an impact should be applied to the calcining device during this low-temperature treatment because the cracked masses tend to easily come off the calcining device.

The strength of the impact applied to the calcining device depends on the depth of the dry powder and/or the catalyst precursor supplied in the calcining device, the diameter, length, wall thickness, and material of the calcining device, the material, type, shape, and position of an impactor, and impacting frequency, etc. Thus, it is preferable that this strength should be set appropriately according to these factors.

Vibration acceleration at the site to which the impact is applied (hereinafter, also referred to as an impact point) is preferably 0.1 m/s$^2$ or more, more preferably 1 m/s$^2$ or more, even more preferably 5 m/s$^2$ or more, particularly preferably 10 m/s$^2$ or more, from the viewpoint of sufficiently reducing adhesion to the inside wall of the calcining device. Moreover, the vibration acceleration is preferably 3000 m/s$^2$ or less, more preferably 1000 m/s$^2$ or less, even more preferably 500 m/s$^2$ or less, particularly preferably 300 m/s$^2$ or less, from the viewpoint of preventing the calcining device from being broken and from the viewpoint of preventing the flow of the powder circulated in the calcining device from being disturbed.

In the present embodiment, the "vibration acceleration" of the impact applied to the calcining device means an average of values measured at distances L/4, 3 L/8, and L/2 from the powder inlet in the calcining device in parallel with the powder flow direction with the whole length of the calcining device represented as L. The measurement positions shall be the same as the positions of the impact points in the cross-sectional direction orthogonal to the powder flow direction in the calcining device. The vibration acceleration can be measured with a vibrometer attached to the calcining device. MD220 (trade name) manufactured by ASAHI KASEI TECHNOSYSTEM CO., LTD. can be used as the vibrometer.

The method for applying the impact thereto is not particularly limited, and an air knocker, a hammer, a hammering apparatus, or the like can be used preferably. The material of a part (this part comes into direct contact with the calcining device) at the end of the impacting portion is not particularly limited as long as it is a material having sufficient heat resistance. For example, general resins and metals capable of resisting the impact can be used. Among them, the metals are preferable. It is preferable that the metals should have hardness without breaking or deforming the calcining device. Those made of copper or SUS can be used preferably. Likewise, the site to which the impact is applied is not particularly limited, and the impact can be given to an operationally advantageous site. It is preferable that the impact should be applied to a site that is not covered with a heating furnace in the calcining device, because the impact can be given directly to the calcining device without a loss.

The number of sites to which the impact is applied may be one or two or more. For efficiently transmitting a vibration thereto, it is preferable that the impact should be applied in a direction perpendicular to the axial direction of a calcination tube when the tube is used as a calcining device. Impacting frequency is not particularly limited. It is preferable that the impact should be applied steadily to the calcining device because this approach tends to more favorably reduce powders adhered in the calcining device. In this context, the phrase "impact is steadily applied" means that the impact is applied preferably once in 1 second to 1 hour inclusive, more preferably once in 1 second to 30 minutes inclusive, even more preferably once in 1 second to 5 minutes inclusive, particularly preferably once in 1 second to 1 minute inclusive. It is preferable that the impacting frequency should be adjusted appropriately according to the vibration acceleration, the depth of the dry powder and the catalyst precursor supplied in the calcining device, the diameter, length, wall thickness, and material of the calcining device, and the material, type, and shape of an impactor.

The calcination method described above can be used regardless of the presence or absence of the W-containing compound solid described later.

(b) Calcination Method Performed in Presence of W-Containing Compound Solid

The calcination in the presence of a W-containing compound solid permits solid-phase diffusion of W from the W-containing compound solid particle to the catalyst particle such that W can be concentrated within the surface of the catalyst particle and in proximity thereto.

(W-Containing Compound Solid)

For example, an ammonium salt, nitrate, carboxylate, ammonium carboxylate, peroxocarboxylate, ammonium peroxocarboxylate, ammonium halide, halide, acetyl acetonate, alkoxide, a tri phenyl compound, polyoxometalate, ammonium polyoxometalate, ditungsten trioxide, tungsten dioxide, tungstic acid, ammonium paratungstate, silicotungstic acid, silicotungstomolybdic acid, silicovanadotungstic acid, and tungstate of W in the form of a powder can be used as the W-containing compound solid to coexist therewith.

(Particle Size of W-Containing Compound Solid)

Upon contact of the W-containing compound solid with the dry powder, etc. during the calcination of the dry powder, etc., part of W is incorporated into the surface and/or inside of the dry powder, etc. As described later, this amount of W incorporated largely contributes to catalyst performance. The smaller the particle size of the W-containing compound solid is, the larger its surface area becomes. As a result, W is more easily incorporated into the dry powder, etc. An average particle size d of the W-containing compound solid is preferably d<300 µm, more preferably d<250 µm, even more preferably d<200 µm, particularly preferably d<150 µm, from the viewpoint of easy incorporation of W and miscibility.

On the other hand, too small a W-containing compound solid tends to be low miscible with the pre-stage calcined powder or the mainly calcined powder, be responsible for clogging in a pipe or the like due to adhesion, or fly out due to circulated gases. The average particle size d of the W-containing compound solid is preferably 1 µm<d, more preferably 5 µm<d, even more preferably 10 µm<d, particularly preferably 20 µm<d, from the viewpoint of operability in the calcination step.

In the present specification, the average particle size of the W-containing compound solid is determined by measuring particle size distributions according to JIS R 1629-1997 "Determination of particle size distributions for fine ceramic raw powders by laser diffraction method" and determining an average value thereof based on volume.

After calcination, the catalyst can also be separated from redundant W-containing compound solids by classification operation or the like. When this operation is performed, it is preferable that the catalyst and the W-containing compound solid should differ in average particle size, from the viewpoint of easy separation. In this case, it is preferable that the W-containing compound solid should have equal to or smaller than 0.8 times the average particle size of the catalyst or should have equal to or greater than 1.2 times the average particle size thereof. The average particle size of the catalyst is preferably 5 to 200 µm, more preferably 10 to 150 µm, from the viewpoint of, for example, obtaining the preferable state of fluidity in fluidized-bed reaction, easily achieving the appropriate rate of reduction of the catalyst, and achieving improved catalyst performance.

The average particle size of the catalyst is determined by measuring particle size distributions according to JIS R 1629-1997 "Determination of particle size distributions for fine ceramic raw powders by laser diffraction method" and determining an average value thereof based on volume, in the same way as in the average particle size of the W-containing compound solid.

The W-containing compound solid may be a commercially available powder raw material, or a commercially available product whose particle size is adjusted by mechanical operation such as grinding. Those obtained by spray-drying an aqueous ammonium metatungstate solution, followed by calcination are preferable because they have an easy-to-adjust particle size and small particle size distribution.

The W-containing compound solid may be allowed to be present in this solid state in the calcining device during calcination without, for example, impregnation with a W-containing solution and/or slurry. By this approach, the W component can be incorporated more conveniently into the catalyst than by a method that requires impregnation, drying, and re-calcination after temporal synthesis of a catalyst.

The amount of W incorporated into the catalyst varies depending on the amount of the W-containing compound solid coexisting with the dry powder, the pre-stage calcined powder, or the mainly calcined powder. The amount of W incorporated thereinto also varies depending on the type and shape (e.g., particle size) of the W-containing compound solid, and the temperature and time of calcination. Therefore, the amount of W coexisting therewith is difficult to generalize. When the atomic ratio of W contained in the W-containing compound solid to Mo contained in the dry powder is defined as $R_{W/Mo}$, the solid preferably satisfies conditions represented by the following formula (4), more preferably satisfies conditions represented by the following formula (4a), even more preferably satisfies conditions represented by the following formula (4b), and particularly preferably satisfies conditions represented by the following formula (4c), from the viewpoint of, for example, improving catalyst performance and from the empirical standpoint:

$$0.001 < R_{W/Mo} < 0.6 \tag{4}$$

$$0.005 < R_{W/Mo} < 0.4 \tag{4a}$$

$$0.01 < R_{W/Mo} < 0.3 \tag{4b}$$

$$0.015 < R_{W/Mo} < 0.2 \tag{4c}$$

((b-1) Step of Calcining Dry Powder in Presence of W-Containing Compound Solid)

In the step of calcining the dry powder in the presence of a W-containing compound solid in a calcining device, the dry powder and the W-containing compound solid are mixed in advance prior to calcination, and then this mixture is calcined. Various mixers such as a cylindrical mixer, a V-shaped mixer, a screw mixer, and a flow mixer can be used as a mixing apparatus.

Moreover, calcination using a rotary kiln, a fluidized calcining furnace, or the like does not necessarily require mixing them in advance. Each of the dry powder and the W-containing compound solid can be introduced separately into the calcining device and calcined with mixing in the calcining device. This method eliminates the need of an apparatus for mixing the dry powder and the W-containing compound solid and is thus more preferable than the method which involves mixing them in advance.

By calcination in the state of contact between the dry powder and the W-containing compound solid, the W-containing compound solid is incorporated, in a state adhering to the surface of the dry powder, into the pre-stage calcined powder and/or the mainly calcined powder, while the powder is calcined. In this step (b-1), the calcination can be performed in the same way as the calcination method (a) for the dry powder except that the mixture of the dry powder and the W-containing compound solid is added to the calcining device and the W-containing compound solid is mixed therewith. The pre-stage calcined powder may be obtained by the step (b-1) and used in the step (b-2). Alternatively, the mainly calcined powder may be obtained by the step (b-1).

((b-2) Step of Calcining Pre-Stage Calcined Powder in Presence of W-Containing Compound Solid)

In this step, the W-containing compound solid is added and mixed into the pre-stage calcined powder obtained by pre-stage calcination, and this mixture is subsequently mainly calcined.

It is preferable that the step of adding and mixing the W-containing compound solid into the pre-stage calcined powder should be performed in an inert gas atmosphere, from the viewpoint of, for example, easily adjusting the redox state of the catalyst to an appropriate one, and achieving improved catalyst performance. Various mixers such as a cylindrical mixer, a V-shaped mixer, a screw mixer, and a flow mixer can be used as a mixing apparatus. Moreover, for calcination using a rotary kiln, a fluidized calcining furnace, or the like, the pre-stage calcined powder and the W-containing compound solid can also be introduced separately to the calcining device for main calcination and calcined with mixing in the calcining device. This method eliminates the need of an apparatus for mixing the dry powder and the W-containing compound solid and is thus more preferable than the method which involves mixing them in advance.

The main calcination can be performed in the same way as the calcination method (a) for the dry powder except that the W-containing compound solid is mixed therewith. The mainly calcined powder may be obtained by the step (b-2) and used as an oxide catalyst. Alternatively, the mainly calcined powder may further be used in the step (b-3).

((b-3) Method of Calcining Mainly Calcined Powder in Presence of W-Containing Compound Solid)

In this method, the W-containing compound solid is added and mixed into the mainly calcined powder obtained by main calcination, and then, this mixture is calcined again. The mainly calcined powder can be produced in the same way as the calcination method (a) for the dry powder.

Various mixers such as a cylindrical mixer, a V-shaped mixer, a screw mixer, and a flow mixer can be used as a mixing apparatus. For calcination using a rotary kiln, a fluidized calcining furnace, or the like, the mainly calcined powder and the W-containing compound solid can also be introduced separately to the calcining device and calcined with mixing in the calcining device. This method eliminates the need of an apparatus for mixing the dry powder and the W-containing compound solid and is thus more preferable than the method which involves mixing them in advance.

The mixture of the mainly calcined powder and the W-containing compound solid can also be calcined in the presence of oxygen. However it is preferable that the mixture should be calcined in the absence of oxygen, from the viewpoint of, for example, easily adjusting the redox state of the catalyst to an appropriate one, and achieving improved catalyst performance. The calcination temperature is preferably 300 to 700° C., more preferably 400 to 600° C., and the calcination time is preferably 0.5 to 100 hours, more preferably 1 to 50 hours, from the viewpoint of, for example, easily and appropriately adjusting the specific surface area of the catalyst, and achieving improved catalyst performance. The calcination may be calcination using a rotary kiln or the like. Alternatively, the mainly calcined powder and the W-containing compound solid may be mixed and heated in a reactor. This approach is also included in the scope of calcination in this step.

Likewise, a W-containing compound solid is added and mixed into a catalyst powder obtained through the step of removing a flow inhibitor described later, and then, this mixture can also be calcined again. Furthermore, the powder obtained through the step (b-3) may be used as an oxide catalyst. A W-containing compound solid is further added and mixed thereinto in the same way as in the step (b-3) after the step of removing a flow inhibitor described later, and then, this mixture can also be calcined again.

Of the steps (b-1), (b-2), and (b-3), the step (b-1) having a fewer number of processes is preferable from the viewpoint of convenient catalyst production. Moreover, the step (b-2) is preferable from the viewpoint of improving catalyst performance. However, the process for producing the oxide catalyst of the present embodiment may comprise two or more of these steps.

W is introduced into the catalyst particle by solid-phase diffusion from the W-containing compound solid coexisting therewith in the calcination step (III). As a result, W is concentrated within the surface of the catalyst particle and in proximity thereto, while the abundance of W is likely to decrease as it gets close to the center of the particle. Accordingly, the gradient in which the concentration of W decreases as it gets close to the center from the surface of the oxide catalyst particle is larger when the calcination step is performed in the presence of the W-containing compound solid than when the catalyst particle contains W contained only in the dry powder. Thus, whether or not the W-containing compound solid has coexisted therewith in the calcination step can be determined briefly based on this gradient.

(Separation Between Catalyst and W-Containing Compound Solid)

As a result of calcining the dry powder, the pre-stage calcined powder, or the mainly calcined powder together with the W-containing compound solid, a portion of the W-containing compound solid is incorporated into the pre-stage calcined powder, the mainly calcined powder, or the oxide catalyst. However, the W-containing compound solid is not wholly incorporated into the pre-stage calcined powder, the mainly calcined powder, or the catalyst. Thus, the finally obtained catalyst is in a state mixed with redundant W-containing compound solids. The redundant W-containing compound solids can be separated from the catalyst using a classification apparatus. Various classification apparatuses such as a vibration sifter, an air classifier, and an apparatus using air classification and separation through a filter in combination can be used as the classification apparatus.

When the oxide catalyst is used in fluidized-bed reaction, air classification can be promoted by the flow of the oxide catalyst in a fluidized-bed reactor to remove the W-containing compound solid. This method eliminates the need of a classification apparatus and is thus more preferable than the separation method using the classification apparatus. The smaller amount of redundant W-containing compound solids is more preferable from the viewpoint of the fluidity of the catalyst, catalyst loads, and dirt in a pipe or an apparatus. The mass of redundant W-containing compound solids is preferably 20% by mass or less, more preferably 10% by mass or less, based on the mass of the catalyst. In this case, a W-containing compound solid having a particle size smaller than that of the oxide catalyst is easily separated by air classification and is thus more preferable.

(Step of Removing Flow Inhibitor)

The oxide catalyst thus produced may contain a flow inhibitor protruding from the surface of the particle. The flow inhibitor is formed in a shape rising and/or protruding from the surface of the oxide catalyst. An oxide catalyst having such a flow inhibitor, when used in fluidized-bed reaction, hardly exhibits sufficient fluidity and, additionally, may result in the lower yield of the product of interest than that brought about by an oxide catalyst free from the flow inhibitor. Thus, it is preferable that the flow inhibitor should be reduced to 2% by mass or less based on the mass of the oxide catalyst by removal from the catalyst.

The method for removing the flow inhibitor is a preferably a method which involves removal by the contact between catalyst particles, etc., under gas circulation. More specific examples thereof include a method which involves circulating a gas, for example, in a hopper in which the catalyst is stored, and a method which involves circulating a gas in a fluidized-bed reactor containing the oxide catalyst. Use of the fluidized-bed reactor eliminates the need of a special apparatus for removing the flow inhibitor. Once a gas is circulated in an apparatus such as a fluidized-bed reactor charged with the oxide catalyst, oxide catalyst particles are brought into contact with each other to remove the flow inhibitor protruding therefrom. The flow inhibitor dissociated from the oxide catalyst is much smaller than the spherical oxide catalyst and is thus discharged, together with the circulated gas, from the system.

It is preferable that the flow inhibitor should be removed such that the density of the oxide catalyst is 300 to 1300 kg/m$^3$ in a container such as a hopper or a fluidized-bed reactor containing the oxide catalyst during flow inhibitor removal, from the viewpoint of, for example, efficiently removing the flow inhibitor, and obtaining the preferable state of contact between catalyst particles. Moreover, the cross-sectional area orthogonal to the gas-phase flow direction of the container is preferably 0.1 to 100 m$^2$, more preferably 0.2 to 85 m$^2$, from the viewpoint of, for example, obtaining the preferable state of contact between catalyst particles, and adjusting the amount of the flow inhibitor removed to the preferable value. The gas circulated for allowing the catalyst to flow in the container is preferably an inert gas (e.g., nitrogen) or air from the viewpoint of, for example, eliminating adverse effect on the catalyst. The linear velocity of the gas in the container is preferably 0.03 m/sec to 5 m/sec, more preferably 0.05 to 1 m/sec, from the viewpoint of, for example, efficiently removing the flow inhibitor, and obtaining the preferable state of contact between catalyst particles. Moreover, the circulation time of the gas is preferably 1 to 50 hours.

(Composition of Constituents Added in Raw Material Preparation Step and Composition of Dry Powder)

For the composition of each constitutive element compound added in the raw material preparation step used in the present embodiment, it is preferable that the composition in the raw material preparation should satisfy conditions represented by the formula (1) shown below, from the viewpoint of preparing a catalyst having favorable catalyst performance and catalyst life. From this viewpoint, it is preferable that the composition in the dry powder should also satisfy the conditions represented by the following formula (1):

$$A_{Mo}:A_V:A_W:A_{Nb}:A_X:A_Z=1:a:b:c:x:z \quad (1)$$

wherein $A_{Mo}$ represents the atomic ratio of Mo; $A_V$ represents the atomic ratio of V; $A_W$ represents the atomic ratio of W; $A_{Nb}$ represents the atomic ratio of Nb; $A_X$ represents the atomic ratio of at least one element selected from the group consisting of Sb and Te; $A_Z$ represents the atomic ratio of at least one element selected from the group consisting of Mn, B, Ti, Al, Ta, an alkali metal and an alkaline earth metal; and a, b, c, x, and z fall within the ranges of 0.01≤a≤1, 0≤b≤1, 0.01≤c≤1, 0.01≤x≤1, and 0≤z≤1, respectively.

The ranges of a, b, c, x, and z are preferably 0.01≤a≤1, 0≤b≤1, 0.01≤c≤1, 0.01≤x≤1, and 0≤z≤1, respectively, more preferably 0.1≤a≤0.5, 0.005≤b≤0.5, 0.1≤c≤0.5, 0.01≤x≤0.5, and 0.001≤z≤0.5, respectively, even more preferably 0.1≤a≤0.45, 0.01≤b≤0.4, 0.1≤c≤0.4, 0.01≤x≤0.4, and 0.001≤z≤0.4, respectively.

(Composition of Catalyst)

The amount of W incorporated into the dry powder, the pre-stage calcined powder, or the mainly calcined powder varies according to the type and shape (e.g., particle size) of the W-containing compound solid, the temperature and time of calcination, etc. For controlling the amount of W incorporated into the dry powder, the pre-stage calcined powder, or the mainly calcined powder, it is preferable that the amount of the W-containing compound solid added should be adjusted such that the composition of W has a particular amount in the oxide catalyst, from the viewpoint of highly selectively obtaining the compound of interest through catalytic reaction. Specifically, it is preferable that the oxide catalyst from which redundant W-containing compound solids have been removed should comprise a catalytic component having a composition represented by the following general formula (3):

$$Mo_1V_aW_{b+b'}Nb_cX_xZ_zO_n \quad (3)$$

wherein a, b, c, x, and z are each as defined above in the formula (1); X represents at least one element selected from the group consisting of Sb and Te; Z represents at least one element selected from the group consisting of Mn, B, Ti, Al, Ta, an alkali metal and an alkaline earth metal; b' represents a changed portion in the composition of W after calcination in the presence of the W-containing compound solid in the calcination step, compared with the composition of W in the raw material preparation; and n represents a value which satisfies the balance of valence and depends on the valences of the constituent metal elements.

The range of b' is preferably 0.001≤b'≤0.3, more preferably 0.005≤b'≤0.2, even more preferably 0.01≤b'≤0.15, particularly preferably 0.015≤b'≤0.1.

An oxide catalyst that exhibits the higher selectivity of the compound of interest is obtained by calcination in the presence of the W-containing compound solid than by calcination without the addition of the W-containing compound solid. On the other hand, this effect is not exerted even if the composition of W is increased in the raw material preparation step. The detailed reason for this is not clear. However, this is presumably because the placement of W at a particular site in proximity to the surface of oxide crystals inhibits the sequential degradation of the product of interest or intermediates in catalytic reaction. Under circumstances where complex oxide crystals that contribute to catalytic reaction are being formed or have been formed in the calcination step, W is presumed to compensate for lattice defect on the crystal surface through gradual solid-phase diffusion. Therefore, the solid-phase diffusion of W seems to be important.

Moreover, an oxide catalyst that exhibits the high selectivity (yield) of the compound of interest can be obtained easily with high degrees of efficiency by the calcination step in the presence of the W-containing compound solid. Specifically, the addition of the W-containing compound to the already-prepared dry powder and/or catalyst precursor can improve the performance of the obtained catalyst without repeating the process from the raw material preparation step.

The amount of W diffused through solid-phase diffusion depends on a plurality of factors such as: the calcination temperature; the calcination time; the particle sizes of the dry powder, the pre-stage calcined powder, the mainly calcined powder, and the W-containing compound solid; and the amount of the W-containing compound solid added. If the calcination temperature, the calcination time, or the particle sizes of the dry powder, the pre-stage calcined powder, and the mainly calcined powder are changed, the growth state of complex oxide crystals or the specific surface area of the catalyst is influenced thereby. As a result, the effect brought about by the addition of the W-containing compound solid is reduced. Therefore, for obtaining more favorable catalyst performance, it is preferred to control the particle size of the W-containing compound solid and the amount of the W-containing compound solid added.

Under the same calcination conditions, the larger the amount of the W-containing compound solid added is, the larger the amount of W diffused through solid-phase diffusion to the catalyst becomes. Moreover, the smaller the average particle size of the W-containing compound solid is, the larger the amount of W diffused through solid-phase diffusion to the catalyst becomes. Therefore, if the atomic ratio of W contained in the W-containing compound solid to Mo contained in the dry powder is represented by $R_{W/Mo}$ and the average particle size of the W-containing compound solid is represented by d as indexes for the amount of the W-containing compound solid added to the catalyst, then the amount of W diffused through solid-phase diffusion has a positive correlation with $R_{W/Mo}/d$. When the dry powder containing each metal element at the atomic ratio represented by the formula (1) is calcined, the solid preferably satisfies conditions represented by the following formula (2), more preferably satisfies conditions represented by the following formula (2a), even more preferably satisfies conditions represented by the following formula (2b), and particularly preferably satisfies conditions represented by the following formula (2c), from the empirical standpoint:

$$3 \text{ m}^{-1} < R_{W/Mo}/d < 600000 \text{ m}^{-1} \quad (2)$$

$$20 \text{ m}^{-1} < R_{W/Mo}/d < 80000 \text{ m}^{-1} \quad (2a)$$

$$50 \text{ m}^{-1} < R_{W/Mo}/d < 30000 \text{ m}^{-1} \quad (2b)$$

$$100 \text{ m}^{-1} < R_{W/Mo}/d < 10000 \text{ m}^{-1} \quad (2c)$$

The oxide catalyst is preferably a silica-supported catalyst. When the oxide catalyst according to the present embodiment is a silica-supported catalyst, it has high mechanical strength and is thus suitable for oxidation reaction and ammoxidation reaction using a fluidized-bed reactor. The content of silica as a carrier is preferably 10 to 80% by mass, more preferably 20 to 70% by mass, even more preferably 30 to 60% by mass, in terms of $SiO_2$ based on the total mass of the silica-supported oxide catalyst comprising the catalytic component and the silica as a carrier, from the viewpoint of obtaining a catalyst having high strength and imparting sufficient activity to the catalyst.

Next, the gas-phase catalytic oxidation reaction or the gas-phase catalytic ammoxidation reaction of propane or isobutane using the oxide catalyst of the present embodiment will be described.

Propane, isobutane, and a raw material for ammonia supplied in the case of ammoxidation reaction are not necessarily required to be highly pure, and gases of industrial grade can be used. For example, air, pure oxygen, or air enriched with pure oxygen can be used as a source of oxygen supply. Furthermore, helium, neon, argon, $CO_2$, water vapor, nitrogen, or the like can also be used as a diluent gas.

The gas-phase catalytic oxidation reaction of propane or isobutane can be performed, for example, under conditions shown below.

The molar ratio of oxygen supplied to the reaction to propane or isobutane is preferably 0.1 to 6, more preferably 0.5 to 4. The reaction temperature is preferably 300 to 500° C., more preferably 350 to ° C. The reaction pressure is preferably $5 \times 10^4$ to $5 \times 10^5$ Pa, more preferably $1 \times 10^5$ to $3 \times 10^5$ Pa. The contacting time is preferably 0.1 to 10 (sec·g/cc), more preferably 0.5 to 5 (sec·g/cc).

In this context, the contacting time in the present embodiment is defined by the following formula (8):

$$\text{Contacting time (sec·g/cc)} = (W/F) \times 273/(273+T) \quad (8)$$

wherein W represents the amount (g) of the catalyst charged; F represents the flow rate (Ncc/sec) of the raw material mixed gas in the normal state (0° C., $1.013 \times 10^5$ Pa); and T represents a reaction temperature (° C.).

The gas-phase catalytic ammoxidation reaction of propane or isobutane can be performed, for example, under conditions shown below.

The molar ratio of oxygen supplied to the reaction to propane or isobutane is preferably 0.1 to 6, more preferably 0.5 to 4. The molar ratio of ammonia supplied to the reaction to propane or isobutane is preferably 0.3 to 1.5, more preferably 0.7 to 1.2. The reaction temperature is preferably 350 to 500° C., more preferably 380 to 470° C. The reaction pressure is preferably $5 \times 10^4$ to $5 \times 10^5$ Pa, more preferably $1 \times 10^5$ to $3 \times 10^5$ Pa. The contacting time is preferably 0.1 to 10 (sec·g/cc), more preferably 0.5 to 5 (sec·g/cc).

A conventional reactor such as a fixed-bed reactor, a fluidized-bed reactor, or a moving-bed reactor can be adopted as the reactor for use in the gas-phase catalytic oxidation reaction and the gas-phase catalytic ammoxidation reaction. The fluidized-bed reactor is preferable because the heat of reaction is easily removed. Moreover, the gas-phase catalytic ammoxidation reaction may be performed in a single-flow manner or in a recycling manner.

The present embodiment can provide an oxide catalyst that can be used in the gas-phase catalytic oxidation reaction or gas-phase catalytic ammoxidation reaction of propane or isobutane, and a production process suitable for large-scale industrial production of the oxide catalyst. According to this production process, an oxide catalyst that can be used to form the compound of interest at high yields can be produced easily.

EXAMPLES

This embodiment will be described in more detail below by Examples and Comparative Examples, but this embodiment is not limited to these Examples.

In the Examples and the Comparative Examples, the conversion of propane or isobutane, and the yield of acrylonitrile or methacrylonitrile follow definitions represented by the following formulas, respectively.

propane or isobutane conversion (%)=(the number of moles of reacted propane or isobutane)/(the number of moles of supplied propane or isobutane)×100 the yield of acrylonitrile or methacrylonitrile (%)= (the number of moles of produced acrylonitrile or methacrylonitrile)/(the number of moles of supplied propane or isobutane)×100

(Preparation of Niobium Mixed Liquid)

A niobium mixed liquid was prepared by the following process. First, 10 kg of water was mixed with 1.530 kg of niobium acid containing 79.8% by mass of $Nb_2O_5$ and 5.266 kg of oxalic acid dihydrate [$H_2C_2O_4 \cdot 2H_2O$]. The feed oxalic acid/niobium molar ratio was 5.0, and the feed niobium concentration was 0.50 (mol-Nb/kg-liquid). This liquid was heated and stirred at 95° C. for 2 hours to obtain a mixed liquid in which niobium was dissolved. This mixed liquid was allowed to stand and ice-cooled, and then, the solid was filtered off by suction filtration to obtain a uniform niobium mixed liquid. The oxalic acid/niobium molar ratio of this niobium mixed liquid was 2.68 by the following analysis.

10 g of this niobium mixed liquid was precisely weighed into a crucible, dried overnight at 95° C., and then heat-treated at 600° C. for 1 hour to obtain 0.7895 g of $Nb_2O_5$. From this result, the niobium concentration was 0.594 (mol-Nb/kg-liquid). 3 g of this niobium mixed liquid was precisely weighed into a 300 mL glass beaker. 200 mL of hot water at about 80° C. was added, and then, 10 mL of 1:1 sulfuric acid was added. While the obtained mixed liquid was maintained at a liquid temperature of 70° C. on a hot stirrer, the mixed liquid was titrated with stirring, using ¼ normal $KMnO_4$. A point at which a light pale pink color due to $KMnO_4$ lasted for about 30 seconds or more was taken as the end point. The concentration of oxalic acid was calculated from the titer of $KMnO_4$ with reference to the following reaction formula, and was 1.592 (mol-oxalic acid/kg).

$$2KMnO_4 + 3H_2SO_4 + 5H_2C_2O_4 \rightarrow K_2SO_4 + 2MnSO_4 + 10CO_2 + 8H_2O$$

The obtained niobium mixed liquid was used as a niobium mixed liquid ($B_0$) in the production of the following complex oxide.

(Preparation of Tungsten Oxide Having Average Particle Size of 40 μm)

A 50% by mass aqueous solution of ammonium metatungstate was prepared from commercial (the trade name "MW-2," manufactured by NIPPON INORGANIC COLOUR & CHEMICAL CO., LTD.) ammonium metatungstate [$(NH_4)_6H_2W_{12}O_{40}$], supplied to a centrifugal spray dryer, dried, and formed into a microspherical shape. The inlet temperature of the dryer was 210° C., and the outlet temperature was 120° C.

100 g of this microspherical ammonium metatungstate was placed in an evaporating dish, and calcined in air at 500° C. for 2 hours, using a fixed calcination furnace, to obtain tungsten oxide [$WO_3$] having an average particle size of 40 μm that was a W-containing compound solid.

The particle size distribution was measured by a laser diffraction scattering particle size distribution measuring apparatus (the trade name "LS230," manufactured by Beckman Coulter), and its volume average was taken as the average particle size. Distilled water was used as the dispersion medium, and calculation was performed with the refractive index of the distilled water being 1.33 and the refractive index of the sample being 1.6.

Example 1

An oxide catalyst whose composition formula was represented by $Mo_1V_{0.22}W_{0.04}Nb_{0.10}Sb_{0.25}O_n/46.7\%$ by mass-$SiO_2$ was prepared as described below.

(Preparation of Raw Material Preparation)

442.7 g of ammonium heptamolybdate [$(NH_4)_6Mo_7O_{24} \cdot 4H_2O$], 64.1 g of ammonium metavanadate [$NH_4VO_3$], and 91.2 g of diantimony trioxide [$Sb_2O_3$] were added to 1.809 kg of water, and the mixture was heated at 95° C. for 1 hour with stirring to prepare an aqueous mixed liquid ($A_1$).

On the other hand, 56.5 g of hydrogen peroxide water containing 30% by mass of $H_2O_2$ was added to 420.6 g of a niobium mixed liquid ($B_0$), and the mixture was stirred and mixed at room temperature for 10 minutes to prepare an aqueous mixed liquid ($C_1$).

The obtained aqueous mixed liquid ($A_1$) was cooled to 70° C. Then, 762.5 g of silica sol containing 34.0% by mass of $SiO_2$ was added to the aqueous mixed liquid ($A_1$), and further, 105.9 g of hydrogen peroxide water containing 30% by mass of $H_2O_2$ was added. Stirring was continued at 55° C. for 30 minutes. Further, to the liquid, the aqueous mixed liquid ($C_1$) and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours with a stirring power Pv=1.2 kW/m³ to obtain a slurry aqueous mixed liquid ($D_1$) that was a raw material preparation.

(Preparation of Dry Powder ($E_1$))

Next, the aqueous mixed liquid ($D_1$) obtained as described above was supplied to a centrifugal spray dryer and dried to obtain a microspherical dry powder ($E_1$) having an average particle size of 51 μm. The inlet temperature of the dryer was 210° C., and the outlet temperature was 120° C.

(Calcination of Dry Powder ($E_1$))

500 g of the dry powder ($E_1$) obtained as described above and 13.8 g of tungsten oxide [$WO_3$] having an average particle size of 40 μm were mixed. A SUS calcination tube having an inner diameter of 3 inches (76 mm), a length of 300 mm, and a wall thickness of 3 mm was filled with the mixture. Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. After cooling, tungsten oxide having a small particle size was separated from the obtained mainly calcined powder by a 42 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane: ammonia:oxygen:helium=1:1:3:18 was supplied with a contact time of 2.8 (sec·g/cc). The propane conversion and the acrylonitrile yield after the reaction are shown in Table 1.

Example 2

An oxide catalyst whose composition formula was represented by $Mo_1V_{0.22}W_{0.04}Nb_{0.10}Sb_{0.25}O_n$/46.7% by mass-$SiO_2$ was prepared as described below.

A dry powder ($E_1$) was obtained as in Example 1. The same SUS calcination tube as used in Example 1 was filled with 500 g of the dry powder ($E_1$). Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 16.5 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 3

An oxide catalyst whose composition formula was represented by $Mo_1V_{0.22}W_{0.04}Nb_{0.10}Sb_{0.25}O_n$/46.7% by mass-$SiO_2$ was prepared as described below.

A dry powder ($E_1$) was obtained as in Example 1. The same SUS calcination tube as used in Example 1 was filled with 588 g of the dry powder ($E_1$). Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. The calcination tube was cooled, and then, 35.3 g of tungsten oxide [$WO_3$] having an average particle size of 40 μm was added into the calcination tube. Under nitrogen gas flow at 5.0 NL/min, the temperature was increased from room temperature to 500° C. at a temperature increase rate of 4° C./min, and calcination was further performed at 500° C. for 2 hours. After cooling, tungsten oxide having a small particle size was separated from the obtained powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The conversion of propane and the acrylonitrile yield after the reaction are shown in Table 1.

Example 4

An oxide catalyst whose composition formula was represented by $Mo_1V_{0.22}W_{0.04}Nb_{0.10}Sb_{0.25}O_n$/46.7% by mass-$SiO_2$ was prepared as described below.

A dry powder ($E_1$) was obtained as in Example 1. The same SUS calcination tube as used in Example 1 was filled with 588 g of the dry powder ($E_1$). Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. 50 g of a catalyst obtained after the calcination tube was cooled was precisely weighed and filled into a vertical tube (inner diameter: 41.6 mm, length: 70 cm) in which a perforated disk having three holes having a diameter of ¼64 inches was provided in the bottom portion, and a paper filter was provided in the upper portion, and air was allowed to flow from the lower side at 380 L/hr for 12 hours. This operation was repeated three times, and the catalyst recovered from the tube was collected. The linear velocity in the body portion at this time was 0.05 m/s. In addition, the catalyst density was 1000 kg/m³. This catalyst and 35.3 g of tungsten oxide [$WO_3$] having an average particle size of 40 μm were contained in the calcination tube. Under nitrogen gas flow at 5.0 NL/min, the temperature was increased from room temperature to 500° C. at a temperature increase rate of 4° C./min, and calcination was further performed at 500° C. for 2 hours. After cooling, tungsten oxide having a small particle size was separated from the obtained powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The conversion of propane and the acrylonitrile yield after the reaction are shown in Table 1.

Comparative Example 1

An oxide catalyst whose composition formula was represented by $Mo_1V_{0.22}W_{0.04}Nb_{0.10}Sb_{0.25}O_n$/46.8% by mass-$SiO_2$ was prepared as described below.

(Preparation of Raw Material Preparation)

424.3 g of ammonium heptamolybdate $[(NH_4)_6Mo_7O_{24}\cdot 4H_2O]$, 61.4 g of ammonium metavanadate $[NH_4VO_3]$, and 87.4 g of diantimony trioxide $[Sb_2O_3]$ were added to 1.732 kg of water, and the mixture was heated at 95° C. for 1 hour with stirring to prepare an aqueous mixed liquid $(A_2)$.

On the other hand, 54.1 g of hydrogen peroxide water containing 30% by mass of $H_2O_2$ was added to 403.1 g of a niobium mixed liquid $(B_0)$, and the mixture was stirred and mixed at room temperature for 10 minutes to prepare an aqueous mixed liquid $(C_2)$.

The obtained aqueous mixed liquid $(A_2)$ was cooled to 70° C. Then, 762.5 g of silica sol containing 34.0% by mass of $SiO_2$ was added to the aqueous mixed liquid $(A_2)$, and further, 101.5 g of hydrogen peroxide water containing 30% by mass of $H_2O_2$ was added. Stirring was continued at 55° C. for 30 minutes. Further, to the liquid, the aqueous mixed liquid $(C_2)$, 44.1 g of ammonium metatungstate containing 50% by mass of $WO_3$, and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid $(D_2)$ that was a raw material preparation.

(Preparation of Dry Powder (E2))

Next, the aqueous mixed liquid $(D_2)$ obtained as described above was supplied to a centrifugal spray dryer and dried to obtain a microspherical dry powder $(E_2)$ having an average particle size of 51 μm. The inlet temperature of the dryer was 210° C., and the outlet temperature was 120° C.

(Calcination of Dry Powder $(E_2)$)

The same SUS calcination tube as used in Example 1 was filled with 500 g of the dry powder $(E_2)$ obtained as described above. Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, the temperature was increased from 340° C. to 670° C. at a temperature increase rate of 3° C./min, the dry powder $(E_2)$ was calcined and maintained at 670° C. for 2 hours, then the temperature was decreased to 350° C. at a temperature decrease rate of 1° C./min, and then the calcined powder was cooled to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

(Preparation of Tungsten Oxide Having Average Particle Size of 500 μm)

Commercial (the trade name "MW-2," manufactured by NIPPON INORGANIC COLOUR & CHEMICAL CO., LTD.) particulate tungsten oxide was sieved to obtain cobalt tungstate having an average particle size of 500 μm.

The particle size distribution was measured by a laser diffraction scattering particle size distribution measuring apparatus (the trade name "LS230," manufactured by Beckman Coulter), and its volume average was taken as the average particle size. Distilled water was used as the dispersion medium, and calculation was performed with the refractive index of the distilled water being 1.33 and the refractive index of the sample being 1.6.

Comparative Example 2

An oxide catalyst whose composition formula was represented by $Mo_1V_{0.22}W_{0.002}Nb_{0.10}Sb_{0.25}O_n$/47.8% by mass-$SiO_2$ was prepared as described below.

A dry powder $(E_1)$ was obtained as in Example 1. The same SUS calcination tube as used in Example 1 was filled with 500 g of the dry powder $(E_1)$. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 0.13 g of tungsten oxide $[WO_3]$ having an average particle size of 500 μm was added into this calcination tube. Under nitrogen flow at 5.0 NL/min, while the calcination tube was rotated around the axis in its length direction, the temperature was increased from room temperature to 670° C. at a temperature increase rate of 3° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 250 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

(Tungsten Oxide Having Average Particle Size of 0.5 μm)

Commercial (the trade name "MW-2," manufactured by NIPPON INORGANIC COLOUR & CHEMICAL CO., LTD.) tungsten oxide having an average particle size of 0.5 μm was used.

The particle size distribution was measured by a laser diffraction scattering particle size distribution measuring apparatus (the trade name "Coulter LS230," manufactured by Beckman), and its volume average was taken as the average particle size. Distilled water was used as the dispersion medium, and calculation was performed with the refractive index of the distilled water being 1.33 and the refractive index of the sample being 1.6.

Comparative Example 3

An oxide catalyst whose composition formula was represented by $Mo_1V_{0.22}W_{0.35}Nb_{0.10}Sb_{0.25}O_n$/39.6% by mass-$SiO_2$ was prepared as described below.

A dry powder ($E_1$) was obtained as in Example 1. The same SUS calcination tube as used in Example 1 was filled with 400 g of the dry powder ($E_1$). Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 150.4 g of tungsten oxide [$WO_3$] having an average particle size of 0.5 μm was added into this calcination tube. Under nitrogen flow at 5.0 NL/min, while the calcination tube was rotated around the axis in its length direction, the temperature was increased from room temperature to 670° C. at a temperature increase rate of 3° C./min, and main calcination was performed under the condition of maintaining the temperature at 670° C. for 2 hours and then decreasing the temperature to 350° C. at a temperature decrease rate of 1° C./min to obtain an oxide catalyst.

The composition of the catalyst was measured by X-ray fluorescence analysis (the trade name "RI NT1000," manufactured by Rigaku, Cr tube, tube voltage: 50 kV, tube current: 50 mA).

$R_{W/Mo}$/d is shown in Table 1.
(Ammoxidation Reaction of Propane)

Propane was subjected to gas-phase ammoxidation reaction as in Example 1, using the oxide obtained as described above. The propane conversion and the acrylonitrile yield after the reaction are shown in Table 1.
(Preparation of Cobalt Tungstate Having Average Particle Size of 15 μm)

Commercial (manufactured by Mitsuwa Chemicals Co., Ltd.) cobalt(II) tungstate (dihydrate) was ground in an agate mortar to obtain cobalt tungstate having an average particle size of 15 μm.

The particle size distribution was measured by a laser diffraction scattering particle size distribution measuring apparatus (the trade name "Coulter LS230," manufactured by Beckman), and its volume average was taken as the average particle size. Distilled water was used as the dispersion medium, and calculation was performed with the refractive index of the distilled water being 1.33 and the refractive index of the sample being 1.6.

Example 5

An oxide catalyst whose composition formula was represented by $Mo_1V_{0.22}W_{0.03}Nb_{0.10}Sb0.25Co_{0.03}O_n$/46.7% by mass-$SiO_2$ was prepared as described below.

A dry powder ($E_1$) was obtained as in Example 1. The same SUS calcination tube as used in Example 1 was filled with 500 g of the dry powder ($E_1$). Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 21.6 g of cobalt tungstate [$CoWO_4$] having an average particle size of 15 μm was added into this calcination tube. Under nitrogen flow at 5.0 NL/min, while the calcination tube was rotated around the axis in its length direction, the temperature was increased from room temperature to 670° C. at a temperature increase rate of 3° C./min, and main calcination was performed under the condition of maintaining the temperature at 670° C. for 2 hours and then decreasing the temperature to 350° C. at a temperature decrease rate of 1° C./min. Tungsten oxide having a small particle size was separated from the obtained mainly calcined powder by a 32 μm sieve to obtain an oxide catalyst.

The composition of the catalyst was measured by X-ray fluorescence analysis (the trade name "RI NT1000," manufactured by Rigaku, Cr tube, tube voltage: 50 kV, tube current: 50 mA).

$R_{W/Mo}$/d is shown in Table 1.
(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 6

An oxide catalyst whose composition formula was represented by $Mo_1V_{0.22}W_{0.07}Nb_{0.10}Sb_{0.25}Ce_{0.005}O_n$/47.1% by mass-$SiO_2$ was prepared as described below.
(Preparation of Raw Material Preparation)

419.5 g of ammonium heptamolybdate [$(NH_4)_6Mo_7O_{24}\cdot 4H_2O$], 60.8 g of ammonium metavanadate [$NH_4VO_3$], 5.23 g of cerium nitrate hexahydrate [$CeNO_3\cdot 6H_2O$], and 86.4 g of diantimony trioxide [$Sb_2O_3$] were added to 1.712 kg of water, and the mixture was heated at 95° C. for 1 hour with stirring to prepare an aqueous mixed liquid ($A_3$).

On the other hand, 53.5 g of hydrogen peroxide water containing 30% by mass of $H_2O_2$ was added to 398.6 g of a niobium mixed liquid ($B_0$), and the mixture was stirred and mixed at room temperature for 10 minutes to prepare an aqueous mixed liquid ($C_3$).

The obtained aqueous mixed liquid ($A_3$) was cooled to 70° C. Then, 769.0 g of silica sol containing 34.0% by mass of $SiO_2$ was added to the aqueous mixed liquid ($A_3$), and further, 100.3 g of hydrogen peroxide water containing 30% by mass of $H_2O_2$ was added. Stirring was continued at 55° C. for 30 minutes. Further, to the liquid, the aqueous mixed liquid ($C_3$), 43.6 g of ammonium metatungstate containing 50% by mass of $WO_3$, and a dispersion in which 210.7 g of powder silica (the trade name "AEROSIL 200," manufactured by Nippon Aerosil Co., Ltd.) was dispersed in 2.844 kg of water were sequentially added, and then, the mixture was stirred at 50° C. for 2.5 hours to obtain a slurry aqueous mixed liquid ($D_3$) that was a raw material preparation.
(Preparation of Dry Powder ($E_3$))

Next, the aqueous mixed liquid ($D_3$) obtained as described above was supplied to a centrifugal spray dryer and dried to obtain a microspherical dry powder ($E_3$) having an average particle size of 50 μm. The inlet temperature of the dryer was 210° C., and the outlet temperature was 120° C.
(Calcination of Dry Powder ($E_3$))

The same SUS calcination tube as used in Example 1 was filled with 500 g of the dry powder ($E_3$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 11.2 g of tungsten oxide [WO$_3$] having an average particle size of 40 µm was added into this calcination tube. Under nitrogen gas flow at 5.0 NL/min, while the calcination tube was rotated around the axis in its length direction, the temperature was increased from room temperature to 670° C. at a temperature increase rate of 5° C./min, and main calcination was performed by maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 µm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Comparative Example 4

An oxide catalyst whose composition formula was represented by Mo$_1$V$_{0.22}$W$_{0.04}$Nb$_{0.10}$Sb$_{0.25}$Ce$_{0.005}$O$_n$/47.2% by mass-SiO$_2$ was prepared as described below.

A dry powder (E$_3$) was obtained as in Example 6. The same SUS calcination tube as used in Example 1 was filled with 500 g of the dry powder (E$_3$). Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min, to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 7

An oxide catalyst whose composition formula was represented by Mo$_1$V$_{0.33}$W$_{0.05}$Nb$_{0.11}$Te$_{0.22}$O$_n$ was prepared as described below.

(Preparation of Raw Material Preparation)

39.0 g of ammonium heptamolybdate [(NH$_4$)$_6$Mo$_7$O$_{24}$·4H$_2$O], 8.47 g of ammonium metavanadate [NH$_4$VO$_3$], and 11.08 g of tellurium acid [H$_6$TeO$_6$] were added to 196 g of water, and the mixture was heated to 60° C. with stirring for dissolution, and then cooled to 30° C. to prepare an aqueous mixed liquid (A$_4$).

On the other hand, 41.3 g of hydrogen peroxide water containing 5% by mass of H$_2$O$_2$ was added to 40.76 g of a niobium mixed liquid (B$_0$), and the mixture was stirred and mixed at room temperature for 10 minutes to prepare an aqueous mixed liquid (C$_4$).

The aqueous mixed liquid (C$_4$) was added to the obtained aqueous mixed liquid (A$_4$), and the mixture was stirred for 30 minutes to obtain an aqueous mixed liquid (D$_4$).

(Preparation of Dry Powder (E$_4$))

The obtained aqueous mixed liquid (D$_4$) was sprayed onto a Teflon (registered trademark) coated iron plate heated to 140° C., to obtain a dry powder (E$_4$) having an average particle size of 49 µm.

(Calcination of Dry Powder (E$_4$))

A quartz calcination tube having an inner diameter of 20 mm, a length of 300 mm, and a wall thickness of 1 mm was filled with 5 g of the dry powder (E$_4$) obtained as described above and 0.15 g of WO$_3$ adjusted to 15 µm. Under nitrogen gas flow at 1.0 NL/min, main calcination was performed under the conditions of 600° C. and 2 hours to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A SUS fixed bed reaction tube having an inner diameter of 4 mm was filled with 0.30 g of the oxide catalyst. The reaction temperature was set to 420° C., and the reaction pressure was set to ordinary pressure. A mixed gas having a molar ratio of propane:ammonia:oxygen:helium=1:1.2:3:14.8 was supplied with a contact time of 0.79 (sec·g/cc). The propane conversion and the acrylonitrile yield after the reaction are shown in Table 1.

Comparative Example 5

An oxide catalyst whose composition formula was represented by Mo$_1$V$_{0.33}$Nb$_{0.11}$Te$_{0.22}$O$_n$ was prepared as described below.

A dry powder (E$_4$) was obtained as in Example 7. The same quartz calcination tube as used in Example 7 was filled with 5 g of the dry powder (E$_4$). Under nitrogen gas flow at 1.0 NL/min, main calcination was performed under the conditions of 600° C. and 2 hours to obtain an oxide catalyst.

The composition of the catalyst was measured by X-ray fluorescence analysis (the trade name "RI NT1000," manufactured by Rigaku, Cr tube, tube voltage: 50 kV, tube current: 50 mA).

(Ammoxidation Reaction of Propane)

Propane was subjected to gas-phase ammoxidation reaction as in Example 7, using the oxide catalyst obtained as described above. The propane conversion and the acrylonitrile yield after the reaction are shown in Table 1.

Example 8

Oxidation Reaction of Propane

Propane was subjected to gas-phase oxidation reaction by the following process, using the oxide catalyst obtained in Example 7. A SUS fixed bed reaction tube having an inner diameter of 4 mm was filled with 0.35 g of the oxide catalyst. The reaction temperature was set to 380° C., and the reaction pressure was set to ordinary pressure. A mixed gas having a molar ratio of propane:oxygen:water vapor:helium=1:3.1:14.0:10.0 was supplied with a contact time of 1.2 (sec·g/cc). The propane conversion and the acrylic acid yield after the reaction are shown in Table 2.

Comparative Example 6

Oxidation Reaction of Propane

Propane was subjected to gas-phase oxidation reaction as in Example 8, using the oxide catalyst obtained in Comparative Example 5. The propane conversion and the acrylic acid yield after the reaction are shown in Table 2.

Example 9

An oxide catalyst whose composition formula was represented by $Mo_1V_{0.22}W_{0.07}Nb_{0.10}Sb_{0.25}O_n$/47.1% by mass-$SiO_2$ was prepared as described below.

A dry powder ($E_2$) was obtained as in Comparative Example 1. 500 g of the dry powder ($E_2$) and 13.8 g of tungsten oxide [$WO_3$] having an average particle size of 40 μm were mixed. The same SUS calcination tube as used in Example 1 was filled with the mixture. Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min, to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 10

An oxide catalyst whose composition formula was represented by $Mo_1V_{0.22}W_{0.07}Nb_{0.10}Sb_{0.25}Ce_{0.005}O_n$/47.1% by mass-$SiO_2$ was prepared as described below.

A dry powder ($E_3$) was obtained as in Example 6. 500 g of the dry powder (E3) and 13.8 g of tungsten oxide [$WO_3$] having an average particle size of 40 μm were mixed. The same SUS calcination tube as used in Example 1 was filled with the mixture. Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min, to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 11

An oxide catalyst whose composition formula was represented by $Mo_1V_{0.22}W_{0.09}Nb_{0.10}Sb_{0.25}Ce_{0.005}O_n$/46.9% by mass-$SiO_2$ was prepared as described below.

A dry powder ($E_3$) was obtained as in Example 6. The same SUS calcination tube as used in Example 1 was filled with 588 g of the dry powder ($E_3$). Under nitrogen gas flow at 5.0 NL/min, while the calcination tube was rotated around the axis in its length direction, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. The calcination tube was cooled, and then, 15.0 g of tungsten oxide [$WO_3$] having an average particle size of 40 μm was added into the calcination tube. Under nitrogen gas flow at 5.0 NL/min, the temperature was increased from room temperature to 500° C. at a temperature increase rate of 4° C./min, and calcination was further performed at 500° C. for 2 hours. After cooling, tungsten oxide having a small particle size was separated from the obtained powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 12

An oxide catalyst whose composition formula was represented by $Mo_1V_{0.22}W_{0.12}Nb_{0.10}Sb_{0.25}Ce_{0.005}O_n$/46.7% by mass-$SiO_2$ was prepared as described below.

A dry powder ($E_3$) was obtained as in Example 6. The same SUS calcination tube as used in Example 1 was filled with 500 g of the dry powder ($E_3$). Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 20.0 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Comparative Example 7

An oxide catalyst whose composition formula was represented by $Mo_1V_{0.22}W_{0.042}Nb_{0.10}Sb_{0.25}O_n$/47.8% by mass-$SiO_2$ was prepared as described below.

An oxide catalyst was obtained as in Comparative Example 2, except that a dry powder ($E_3$) was used instead of the dry powder ($E_1$).

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Comparative Example 8

An oxide catalyst whose composition formula was represented by $Mo_1V_{0.22}W_{0.39}Nb_{0.10}Sb_{0.25}O_n$/39.6% by mass-$SiO_2$ was prepared as described below.

An oxide catalyst was obtained as in Comparative Example 3, except that a dry powder ($E_3$) was used instead of the dry powder ($E_1$).

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction as in Example 1, using the oxide catalyst obtained as described above. The propane conversion and the acrylonitrile yield after the reaction are shown in Table 1.

Example 13

An oxide catalyst whose composition formula was represented by $Mo_1V_{0.30}W_{0.04}Nb_{0.10}Sb_{0.22}O_n$/46.8% by mass-$SiO_2$ was prepared as described below.

(Preparation of Raw Material Preparation)

436.8 g of ammonium heptamolybdate [$(NH_4)_6Mo_7O_{24} \cdot 4H_2O$], 86.2 g of ammonium metavanadate [$NH_4VO_3$], and 79.2 g of diantimony trioxide [$Sb_2O_3$] were added to 2.451 kg of water, and the mixture was heated at 95° C. for 1 hour with stirring to prepare an aqueous mixed liquid ($A_5$).

On the other hand, 55.7 g of hydrogen peroxide water containing 30% by mass of $H_2O_2$ was added to 414.9 g of a niobium mixed liquid ($B_0$), and the mixture was stirred and mixed at room temperature for 10 minutes to prepare an aqueous mixed liquid ($C_5$).

The obtained aqueous mixed liquid ($A_5$) was cooled to 70° C. Then, 762.5 g of silica sol containing 34.0% by mass of $SiO_2$ was added to the aqueous mixed liquid (A5), and further, 91.9 g of hydrogen peroxide water containing 30% by mass of $H_2O_2$ was added. Stirring was continued at 55° C. for 30 minutes. Further, to the liquid, the aqueous mixed liquid ($C_5$) and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid ($D_5$) that was a raw material preparation.

(Preparation of Dry Powder ($E_5$))

Next, the aqueous mixed liquid ($D_5$) obtained as described above was supplied to a centrifugal spray dryer and dried to obtain a microspherical dry powder ($E_5$) having an average particle size of 51 μm. The inlet temperature of the dryer was 210° C., and the outlet temperature was 120° C.

(Calcination of Dry Powder ($E_5$))

The same SUS calcination tube as used in Example 1 was filled with 500 g of the dry powder ($E_5$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour to obtain a pre-stage calcined powder. The pre-stage calcined powder was cooled to room temperature. 4.4 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:

ammonia:oxygen:helium=1:1:3:18 was supplied with a contact time of 2.8 (sec·g/cc). The propane conversion and the acrylonitrile yield after the reaction are shown in Table 1.

Example 14

An oxide catalyst whose composition formula was represented by $Mo_1V_{0.15}W_{0.04}Nb_{0.10}Sb_{0.30}O_n$/46.6% by mass-$SiO_2$ was prepared as described below.
(Preparation of Raw Material Preparation)
440.8 g of ammonium heptamolybdate [$(NH_4)_6Mo_7O_{24}\cdot 4H_2O$], 43.5 g of ammonium metavanadate [$NH_4VO_3$], and 108.9 g of diantimony trioxide [$Sb_2O_3$] were added to 1.212 kg of water, and the mixture was heated at 95° C. for 1 hour with stirring to prepare an aqueous mixed liquid ($A_6$).
On the other hand, 56.2 g of hydrogen peroxide water containing 30% by mass of $H_2O_2$ was added to 418.8 g of a niobium mixed liquid ($B_0$), and the mixture was stirred and mixed at room temperature for 10 minutes to prepare an aqueous mixed liquid ($C_6$).
The obtained aqueous mixed liquid ($A_6$) was cooled to 70° C. Then, 762.5 g of silica sol containing 34.0% by mass of $SiO_2$ was added to the aqueous mixed liquid ($A_6$), and further, 126.5 g of hydrogen peroxide water containing 30% by mass of $H_2O_2$ was added. Stirring was continued at 55° C. for 30 minutes. Further, to the liquid, the aqueous mixed liquid ($C_6$) and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid ($D_6$) that was a raw material preparation.
(Preparation of Dry Powder ($E_6$))
Next, the aqueous mixed liquid ($D_6$) obtained as described above was supplied to a centrifugal spray dryer and dried to obtain a microspherical dry powder ($E_6$) having an average particle size of 52 µm. The inlet temperature of the dryer was 210° C., and the outlet temperature was 120° C.
(Calcination of Dry Powder ($E_6$))
The same SUS calcination tube as used in Example 1 was filled with 500 g of the dry powder ($E_6$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 13.4 g of tungsten oxide [$WO_3$] having an average particle size of 40 µm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 µm sieve to obtain an oxide catalyst.
The composition of the catalyst was measured by X-ray fluorescence analysis (the trade name "RINT1000," manufactured by Rigaku, Cr tube, tube voltage: 50 kV, tube current: 50 mA).
$R_{W/Mo}$/d is shown in Table 1.
(Ammoxidation Reaction of Propane)
Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane: ammonia:oxygen:helium=1:1:3:18 was supplied with a contact time of 2.8 (sec·g/cc). The propane conversion and the acrylonitrile yield after the reaction are shown in Table 1.

Example 15

An oxide catalyst whose composition formula was represented by $Mo_1V_{0.24}W_{0.04}Nb_{0.20}Sb_{0.25}O_n$/46.8% by mass-$SiO_2$ was prepared as described below.
(Preparation of Raw Material Preparation)
413.4 g of ammonium heptamolybdate [$(NH_4)_6Mo_7O_{24}\cdot 4H_2O$], 65.3 g of ammonium metavanadate [$NH_4VO_3$], and 85.1 g of diantimony trioxide [$Sb_2O_3$] were added to 1.84 kg of water, and the mixture was heated at 95° C. for 1 hour with stirring to prepare an aqueous mixed liquid ($A_7$).
On the other hand, 105.5 g of hydrogen peroxide water containing 30% by mass of $H_2O_2$ was added to 785.6 g of a niobium mixed liquid ($B_0$), and the mixture was stirred and mixed at room temperature for 10 minutes to prepare an aqueous mixed liquid ($C_7$).
The obtained aqueous mixed liquid ($A_7$) was cooled to 70° C. Then, 762.5 g of silica sol containing 34.0% by mass of $SiO_2$ was added to the aqueous mixed liquid (A7), and further, 98.9 g of hydrogen peroxide water containing 30% by mass of $H_2O_2$ was added. Stirring was continued at 55° C. for 30 minutes. Further, to the liquid, the aqueous mixed liquid ($C_7$) and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid ($D_7$) that was a raw material preparation.
(Preparation of Dry Powder ($E_7$))
Next, the aqueous mixed liquid ($D_7$) obtained as described above was supplied to a centrifugal spray dryer and dried to obtain a microspherical dry powder ($E_7$) having an average particle size of 50 µm. The inlet temperature of the dryer was 210° C., and the outlet temperature was 120° C.
(Calcination of Dry Powder (E7))
The same SUS calcination tube as used in Example 1 was filled with 500 g of the dry powder ($E_7$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 12.9 g of tungsten oxide [$WO_3$] having an average particle size of 40 µm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 µm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 16

An oxide catalyst whose composition formula was represented by $Mo_1V_{0.22}W_{0.04}Nb_{0.10}Sb_{0.25}O_n/54.9\%$ by mass-$SiO_2$ was prepared as described below.

(Preparation of Raw Material Preparation)

374.5 g of ammonium heptamolybdate $[(NH_4)_6Mo_7O_{24}\cdot 4H_2O]$, 54.2 g of ammonium metavanadate $[NH_4VO_3]$, and 77.1 g of diantimony trioxide $[Sb_2O_3]$ were added to 1.523 kg of water, and the mixture was heated at 95° C. for 1 hour with stirring to prepare an aqueous mixed liquid ($A_8$).

On the other hand, 47.8 g of hydrogen peroxide water containing 30% by mass of $H_2O_2$ was added to 355.7 g of a niobium mixed liquid ($B_0$), and the mixture was stirred and mixed at room temperature for 10 minutes to prepare an aqueous mixed liquid ($C_8$).

The obtained aqueous mixed liquid ($A_8$) was cooled to 70° C. Then, 762.5 g of silica sol containing 34.0% by mass of $SiO_2$ was added to the aqueous mixed liquid ($A_8$), and further, 89.5 g of hydrogen peroxide water containing 30% by mass of $H_2O_2$ was added. Stirring was continued at 55° C. for 30 minutes. Further, to the liquid, the aqueous mixed liquid ($C_8$) and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid ($D_8$) that was a raw material preparation.

(Preparation of Dry Powder ($E_8$))

Next, the aqueous mixed liquid ($D_8$) obtained as described above was supplied to a centrifugal spray dryer and dried to obtain a microspherical dry powder ($E_8$) having an average particle size of 49 μm. The inlet temperature of the dryer was 210° C., and the outlet temperature was 120° C.

(Calcination of Dry Powder ($E_8$))

The same SUS calcination tube as used in Example 1 was filled with 500 g of the dry powder ($E_8$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 10.4 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 17

An oxide catalyst whose composition formula was represented by $Mo_1V_{0.22}W_{0.04}Nb_{0.10}Sb0.25B_{0.15}O_n/46.9\%$ by mass-$SiO_2$ was prepared as described below.

(Preparation of Raw Material Preparation)

432.1 g of ammonium heptamolybdate $[(NH_4)_6Mo_7O_{24}\cdot 4H_2O]$, 62.6 g of ammonium metavanadate $[NH_4VO_3]$, and 89.0 g of diantimony trioxide $[Sb_2O_3]$ were added to 1.890 kg of water, and the mixture was heated at 95° C. for 1 hour with stirring to prepare an aqueous mixed liquid ($A_9$).

On the other hand, 55.1 g of hydrogen peroxide water containing 30% by mass of $H_2O_2$ was added to 410.5 g of a niobium mixed liquid ($B_0$), and the mixture was stirred and mixed at room temperature for 10 minutes to prepare an aqueous mixed liquid ($C_9$).

The obtained aqueous mixed liquid ($A_9$) was cooled to 70° C. Then, 762.5 g of silica sol containing 34.0% by mass of $SiO_2$ was added to the aqueous mixed liquid ($A_9$), and further, 89.5 g of hydrogen peroxide water containing 30% by mass of $H_2O_2$ was added. Stirring was continued at 55° C. for 30 minutes. Further, to the liquid, the aqueous mixed liquid ($C_9$), a dispersion in which 208.9 g of powder silica (the trade name "AEROSIL 200," manufactured by Nippon Aerosil Co., Ltd.) was dispersed in 2.820 kg of water, and 22.8 g of boric acid [$H_3BO_3$] were sequentially added, and then, the mixture was stirred at 50° C. for 2.5 hours to obtain a slurry aqueous mixed liquid ($D_9$) that was a raw material preparation.

(Preparation of Dry Powder ($E_9$))

Next, the aqueous mixed liquid ($D_9$) obtained as described above was supplied to a centrifugal spray dryer and dried to obtain a microspherical dry powder ($E_9$) having an average particle size of 51 μm. The inlet temperature of the dryer was 210° C., and the outlet temperature was 120° C.

(Calcination of Dry Powder ($E_9$))

The same SUS calcination tube as used in Example 1 was filled with 500 g of the dry powder ($E_9$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 15.2 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.
(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 18

An oxide catalyst whose composition formula was represented by $Mo_1V_{0.22}W_{0.04}Nb_{0.10}Sb_{0.25}Mn_{0.003}Ce_{0.006}O_n$/46.8% by mass-$SiO_2$ was prepared as described below.
(Preparation of Raw Material Preparation)

440.2 g of ammonium heptamolybdate [$(NH_4)_6Mo_7O_{24}·4H_2O$], 63.7 g of ammonium metavanadate [$NH_4VO_3$], 90.7 g of diantimony trioxide [$Sb_2O_3$], and 6.58 g of cerium nitrate [$Ce(NO_3)_3·6H_2O$] were added to 1.913 kg of water, and the mixture was heated at 95° C. for 1 hour with stirring to prepare an aqueous mixed liquid ($A_{10}$).

On the other hand, 56.1 g of hydrogen peroxide water containing 30% by mass of $H_2O_2$ was added to 418.2 g of a niobium mixed liquid ($B_0$), and the mixture was stirred and mixed at room temperature for 10 minutes to prepare an aqueous mixed liquid ($C_{10}$).

The obtained aqueous mixed liquid ($A_{10}$) was cooled to 70° C. Then, 762.5 g of silica sol containing 34.0% by mass of $SiO_2$ was added to the aqueous mixed liquid ($A_{10}$), and further, 89.5 g of hydrogen peroxide water containing 30% by mass of $H_2O_2$ was added. Stirring was continued at 55° C. for 30 minutes. Further, to the liquid, the aqueous mixed liquid ($C_{10}$), a dispersion in which 208.9 g of powder silica (the trade name "AEROSIL 200," manufactured by Nippon Aerosil Co., Ltd.) was dispersed in 2.820 kg of water, and 2.13 g of manganese nitrate [$Mn(NO_3)_2·6H_2O$] were sequentially added, and then, the mixture was stirred at 50° C. for 2.5 hours to obtain a slurry aqueous mixed liquid ($D_{10}$) that was a raw material preparation.
(Preparation of Dry Powder ($E_{10}$))

Next, the aqueous mixed liquid ($D_{10}$) obtained as described above was supplied to a centrifugal spray dryer and dried to obtain a microspherical dry powder ($E_{10}$) having an average particle size of 53 μm. The inlet temperature of the dryer was 210° C., and the outlet temperature was 120° C.
(Calcination of Dry Powder ($E_{10}$))

The same SUS calcination tube as used in Example 1 was filled with 500 g of the dry powder ($E_{10}$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 13.2 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.
(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 19

An oxide catalyst whose composition formula was represented by $Mo_1V_{0.22}W_{0.04}Nb_{0.10}Sb_{0.25}Ta_{0.001}Ce_{0.005}O_n$/46.9% by mass-$SiO_2$ was prepared as described below.
(Preparation of Raw Material Preparation)

436.5 g of ammonium heptamolybdate [$(NH_4)_6Mo_7O_{24}·4H_2O$], 63.2 g of ammonium metavanadate [$NH_4VO_3$], 89.8 g of diantimony trioxide [$Sb_2O_3$], and 5.44 g of cerium nitrate [$Ce(NO_3)_3·6H_2O$] were added to 1.896 kg of water, and the mixture was heated at 95° C. for 1 hour with stirring to prepare an aqueous mixed liquid ($A_{11}$).

On the other hand, 55.7 g of hydrogen peroxide water containing 30% by mass of $H_2O_2$ was added to 414.7 g of a niobium mixed liquid ($B_0$), and the mixture was stirred and mixed at room temperature for 10 minutes to prepare an aqueous mixed liquid ($C_{11}$).

The obtained aqueous mixed liquid ($A_{11}$) was cooled to 70° C. Then, 762.5 g of silica sol containing 34.0% by mass of $SiO_2$ was added to the aqueous mixed liquid ($A_{11}$), and further, 89.5 g of hydrogen peroxide water containing 30% by mass of $H_2O_2$ was added. Stirring was continued at 55° C. for 30 minutes. Further, to the liquid, the aqueous mixed liquid ($C_{11}$), a dispersion in which 208.9 g of powder silica (the trade name "AEROSIL 200," manufactured by Nippon Aerosil Co., Ltd.) was dispersed in 2.820 kg of water, and 6.20 g of tantalum acid were sequentially added, and then, the mixture was stirred at 50° C. for 2.5 hours to obtain a slurry aqueous mixed liquid ($D_{11}$) that was a raw material preparation.

(Preparation of Dry Powder ($E_{11}$))

Next, the aqueous mixed liquid ($D_{11}$) obtained as described above was supplied to a centrifugal spray dryer and dried to obtain a microspherical dry powder ($E_{11}$) having an average particle size of 48 μm. The inlet temperature of the dryer was 210° C., and the outlet temperature was 120° C.

(Calcination of Dry Powder ($E_{11}$))

The same SUS calcination tube as used in Example 1 was filled with 500 g of the dry powder ($E_{11}$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 14.9 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 20

An oxide catalyst whose composition formula was represented by $Mo_1V_{0.22}W_{0.04}Nb_{0.10}Sb_{0.25}Al_{0.005}Ti_{0.009}O_n$/46.8% by mass-$SiO_2$ was prepared as described below.

(Preparation of Raw Material Preparation)

440.7 g of ammonium heptamolybdate [$(NH_4)_6Mo_7O_{24}\cdot 4H_2O$], 63.8 g of ammonium metavanadate [$NH_4VO_3$], and 90.8 g of diantimony trioxide [$Sb_2O_3$] were added to 1.978 kg of water, and the mixture was heated at 95° C. for 1 hour with stirring to prepare an aqueous mixed liquid ($A_{12}$).

On the other hand, 56.2 g of hydrogen peroxide water containing 30% by mass of $H_2O_2$ was added to 418.7 g of a niobium mixed liquid ($B_0$), and the mixture was stirred and mixed at room temperature for 10 minutes to prepare an aqueous mixed liquid ($C_{12}$).

The obtained aqueous mixed liquid ($A_{12}$) was cooled to 70° C. Then, 762.5 g of silica sol containing 34.0% by mass of $SiO_2$ was added to the aqueous mixed liquid ($A_{12}$), and further, 89.5 g of hydrogen peroxide water containing 30% by mass of $H_2O_2$ was added. Stirring was continued at 55° C. for 30 minutes. Further, to the liquid, the aqueous mixed liquid ($C_{12}$), a dispersion in which 208.9 g of powder silica (the trade name "AEROSIL 200," manufactured by Nippon Aerosil Co., Ltd.) was dispersed in 2.820 kg of water, 0.632 g of aluminum oxide [$Al_2O_3$], and 1.78 g of titanium oxide [$TiO_2$] were sequentially added, and then, the mixture was stirred at 50° C. for 2.5 hours to obtain a slurry aqueous mixed liquid ($D_{12}$) that was a raw material preparation.

(Preparation of Dry Powder ($E_{12}$))

Next, the aqueous mixed liquid ($D_{12}$) obtained as described above was supplied to a centrifugal spray dryer and dried to obtain a microspherical dry powder ($E_{12}$) having an average particle size of 52 μm. The inlet temperature of the dryer was 210° C., and the outlet temperature was 120° C.

(Calcination of Dry Powder ($E_{12}$))

The same SUS calcination tube as used in Example 1 was filled with 500 g of the dry powder ($E_{12}$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 14.7 g of tungsten oxide [$WO_3$] having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 21

An oxide catalyst whose composition formula was represented by $Mo_1V_{0.22}W_{0.04}Nb_{0.10}Sb_{0.25}La_{0.003}O_n/46.7\%$ by mass-$SiO_2$ was prepared as described below.

(Preparation of Raw Material Preparation)

441.7 g of ammonium heptamolybdate $[(NH_4)_6Mo_7O_{24}\cdot 4H_2O]$, 64.0 g of ammonium metavanadate $[NH_4VO_3]$, 91.0 g of diantimony trioxide $[Sb_2O_3]$, and 1.86 g of lanthanum nitrate $[La(NO_3)_3\cdot 6H_2O]$ were added to 1.933 kg of water, and the mixture was heated at 95° C. for 1 hour with stirring to prepare an aqueous mixed liquid $(A_{13})$.

56.3 g of hydrogen peroxide water containing 30% by mass of $H_2O_2$ was added to 419.6 g of a niobium mixed liquid $(B_0)$, and the mixture was stirred and mixed at room temperature for 10 minutes to prepare an aqueous mixed liquid $(C_{13})$.

The obtained aqueous mixed liquid $(A_{13})$ was cooled to 70° C. Then, 762.5 g of silica sol containing 34.0% by mass of $SiO_2$ was added to the aqueous mixed liquid $(A_{13})$, and further, 89.5 g of hydrogen peroxide water containing 30% by mass of $H_2O_2$ was added. Stirring was continued at 55° C. for 30 minutes. Further, to the liquid, the aqueous mixed liquid $(C_{13})$ and a dispersion in which 208.9 g of powder silica (the trade name "AEROSIL 200," manufactured by Nippon Aerosil Co., Ltd.) was dispersed in 2.820 kg of water were sequentially added, and then, the mixture was stirred at 50° C. for 2.5 hours to obtain a slurry aqueous mixed liquid $(D_{13})$ that was a raw material preparation.

(Preparation of Dry Powder $(E_{13})$)

Next, the aqueous mixed liquid $(D_{13})$ obtained as described above was supplied to a centrifugal spray dryer and dried to obtain a microspherical dry powder $(E_{13})$ having an average particle size of 50 μm. The inlet temperature of the dryer was 210° C., and the outlet temperature was 120° C.

(Calcination of Dry Powder $(E_{13})$)

The same SUS calcination tube as used in Example 1 was filled with 500 g of the dry powder $(E_{13})$ obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 14.0 g of tungsten oxide $[WO_3]$ having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RI NT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Example 22

An oxide catalyst whose composition formula was represented by $Mo_1V_{0.22}W_{0.06}Nb_{0.10}Sb_{0.25}Bi_{0.015}O_n/47.1\%$ by mass-$SiO_2$ was prepared as described below.

(Preparation of Raw Material Preparation)

426.5 g of ammonium heptamolybdate $[(NH_4)_6Mo_7O_{24}\cdot 4H_2O]$, 61.8 g of ammonium metavanadate $[NH_4VO_3]$, 87.8 g of diantimony trioxide $[Sb_2O_3]$, and 17.6 g of bismuth nitrate $[Bi(NO_3)_3\cdot 5H_2O]$ were added to 1.914 kg of water, and the mixture was heated at 95° C. for 1 hour with stirring to prepare an aqueous mixed liquid $(A_{14})$.

54.4 g of hydrogen peroxide water containing 30% by mass of $H_2O_2$ was added to 405.1 g of a niobium mixed liquid $(B_0)$, and the mixture was stirred and mixed at room temperature for 10 minutes to prepare an aqueous mixed liquid $(C_{14})$.

The obtained aqueous mixed liquid $(A_{14})$ was cooled to 70° C. Then, 826.4 g of silica sol containing 34.0% by mass of $SiO_2$ was added to the aqueous mixed liquid $(A_{14})$, and further, 102.0 g of hydrogen peroxide water containing 30% by mass of $H_2O_2$ was added. Stirring was continued at 55° C. for 30 minutes. Further, to the liquid, the aqueous mixed liquid $(C_{14})$ and a dispersion in which 187.2 g of powder silica (the trade name "AEROSIL 200," manufactured by Nippon Aerosil Co., Ltd.) was dispersed in 2.62 kg of water were sequentially added, and then, the mixture was stirred at 50° C. for 2.5 hours to obtain a slurry aqueous mixed liquid $(D_{14})$ that was a raw material preparation.

(Preparation of Dry Powder $(E_{14})$)

Next, the aqueous mixed liquid $(D_{14})$ obtained as described above was supplied to a centrifugal spray dryer and dried to obtain a microspherical dry powder (E14) having an average particle size of 52 μm. The inlet temperature of the dryer was 210° C., and the outlet temperature was 120° C.

(Calcination of Dry Powder $(E_{14})$)

The same SUS calcination tube as used in Example 1 was filled with 500 g of the dry powder $(E_{14})$ obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour. The calcination tube was cooled to room temperature. 13.6 g of tungsten oxide $[WO_3]$ having an average particle size of 40 μm was added into this calcination tube. Under nitrogen flow at 5.0 NL/min, while the calcination tube was rotated around the axis in its length direction, the temperature was increased from room temperature to 670° C. at a temperature increase rate of 5° C./min, and main calcination was performed under the condition of maintaining the temperature at 670° C. for 2 hours and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

(Tungsten Oxide Having Average Particle Size of 0.2 μm)

Tungsten oxide obtained by a process similar to that by which tungsten oxide having an average particle size of 40 μm was obtained was ground in an agate mortar to obtain tungsten oxide having an average particle size of 0.2 μm.

The particle size distribution was measured by a laser diffraction scattering particle size distribution measuring apparatus (the trade name "Coulter LS230," manufactured by Beckman), and its volume average was taken as the average particle size. Distilled water was used as the dispersion medium, and calculation was performed with the refractive index of the distilled water being 1.33 and the refractive index of the sample being 1.6.

Comparative Example 9

An oxide catalyst whose composition formula was represented by $Mo_1V_{0.22}W_{0.04}Nb_{0.10}Sb_{0.25}O_n$/46.7% by mass-$SiO_2$ was prepared as described below.

(Calcination of Dry Powder ($E_1$))

A dry powder ($E_1$) was obtained as in Example 1. An oxide catalyst was obtained by a procedure similar to that of Example 3, except that tungsten oxide [$WO_3$] having an average particle size of 0.2 μm was used.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Comparative Example 10

An oxide catalyst whose composition formula was represented by $Mo_1V_{0.22}W_{0.0002}Nb_{0.10}Sb_{0.25}O_n$/47.8% by mass-$SiO_2$ was prepared as described below.

(Calcination of Dry Powder ($E_1$))

A dry powder ($E_1$) was obtained as in Example 1. 500 g of the dry powder ($E_1$) and 0.03 g of tungsten oxide [$WO_3$] prepared to 50 μm were mixed. A SUS calcination tube having a diameter of 3 inches was filled with the mixture. Under nitrogen gas flow at 5.0 NL/min, while the tube was rotated, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

Comparative Example 11

An oxide catalyst whose composition formula was represented by $Mo_1V_{0.22}W_{4.0}Nb_{0.10}Sb_{0.25}O_n$/14.2% by mass-$SiO_2$ was prepared as described below.

(Calcination of Dry Powder ($E_1$))

A dry powder ($E_1$) was obtained as in Example 1. 500 g of the dry powder ($E_1$) and 2309 g of tungsten oxide [$WO_3$] prepared to 15 μm were mixed. A SUS calcination tube having a diameter of 3 inches was filled with the mixture. Under nitrogen gas flow at 5.0 NL/min, while the tube was rotated, pre-stage calcination and main calcination were performed. In the pre-stage calcination, the temperature was increased from room temperature to 340° C. at a temperature increase rate of 0.75° C./min, and calcination was performed at 340° C. for 1 hour. Then, in the main calcination, calcination was performed by increasing the temperature from 340° C. to 670° C. at a temperature increase rate of 3° C./min, maintaining the temperature at 670° C. for 2 hours, and then decreasing the temperature to 350° C. at a temperature decrease rate of 1° C./min. After cooling, tungsten oxide having a small particle size was separated from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}$/d is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane: ammonia:oxygen:helium=1:1:3:18 was supplied with a contact time of 2.8 (sec·g/cc). The propane conversion and the acrylonitrile yield after the reaction are shown in Table 1.

Example 23

An oxide catalyst whose composition formula was represented by $Mo_1V_{0.22}W_{0.04}Nb_{0.10}Sb_{0.25}O_n/46.7\%$ by mass-$SiO_2$ was prepared as described below.
(Calcination of Dry Powder ($E_1$))
An operation similar to that of Example 1 was repeated to obtain 80 kg of a dry powder ($E_1$). Using a SUS cylindrical calcination tube having an inner diameter of 150 mm, a length of 1150 mm, and a wall thickness of 7 mm in which six weir plates having a height of 30 mm were mounted so as to divide the length of the heating furnace portion into seven equal parts, and while the calcination tube was rotated around the axis in its length direction, pre-stage calcination was performed. In the pre-stage calcination, the dry powder was allowed to flow through the calcination tube at a rate of 340 g/hr, nitrogen gas at 10 N liters/min was allowed to flow through the calcination tube, the temperature was increased from room temperature to 340° C. at a temperature increase rate of 0.75° C./min, and calcination was performed at 340° C. for 1 hour. The obtained pre-stage calcined powder was cooled to room temperature. Next, while 6.6 g/hr of tungsten oxide [$WO_3$] having an average particle size of 40 μm and 200 g/hr of the pre-stage calcined powder were allowed to flow through another SUS cylindrical calcination tube having an inner diameter of 150 mm, a length of 1150 mm, and a wall thickness of 7 mm, and under nitrogen flow at 6 N liters/min, while the calcination tube was rotated around the axis in its length direction, main calcination was performed. In the main calcination, calcination was performed by increasing the temperature from room temperature to 670° C. at a temperature increase rate of 5° C./min, maintaining the temperature at 670° C. for 2 hours, and then decreasing the temperature to 350° C. at a temperature decrease rate of 1° C./min. After cooling, tungsten oxide having a small particle size was separated and removed from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.
(Ammoxidation Reaction of Propane)
Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane: ammonia:oxygen:helium=1:1:3:18 was supplied with a contact time of 2.8 (sec·g/cc). The propane conversion and the acrylonitrile yield after the reaction are shown in Table 1.

Example 24

An oxide catalyst whose composition formula was represented by $Mo_1V_{0.22}W_{0.04}Nb_{0.10}Sb_{0.25}O_n/46.7\%$ by mass-$SiO_2$ was prepared as described below.
(Calcination of Dry Powder ($E_1$))
An operation similar to that of Example 1 was repeated to obtain 80 kg of a dry powder ($E_1$). Pre-stage calcination was performed by a process similar to that of Example 22, except that using a SUS cylindrical calcination tube having an inner diameter of 80 mm, a length of 1300 mm, and a wall thickness of 2 mm in which seven weir plates having a height of 15 mm were mounted so as to divide the length of the heating furnace portion into eight equal parts, the dry powder and nitrogen gas were allowed to flow through the calcination tube at a rate of 86 g/hr and at 2.2 N liters/min, respectively. A pre-stage calcined powder was obtained. Next, main calcination was performed as in Example 22, except that using another SUS calcination tube having an inner diameter of 80 mm, a length of 1300 mm, and a wall thickness of 2 mm in which seven weir plates having a height of 30 mm were mounted so as to divide the length of the heating furnace portion into eight equal parts, and while 1.65 g/hr of tungsten oxide [$WO_3$] having an average particle size of 40 μm and 50 g/hr of the pre-stage calcined powder were allowed to flow through the calcination tube, nitrogen gas at 1.7 N liters/min was allowed to flow. After cooling, tungsten oxide having a small particle size was separated and removed from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.
(Ammoxidation Reaction of Propane)
Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane: ammonia:oxygen:helium=1:1:3:18 was supplied with a contact time of 2.8 (sec·g/cc). The propane conversion and the acrylonitrile yield after the reaction are shown in Table 1.

Example 25

An oxide catalyst whose composition formula was represented by $Mo_1V_{0.22}W_{0.04}Nb_{0.10}Sb_{0.25}O_n/46.7\%$ by mass-$SiO_2$ was prepared as described below.
(Calcination of Dry Powder ($E_1$))
An operation similar to that of Example 1 was repeated to obtain 1000 kg of a dry powder ($E_1$). Pre-stage calcination was performed by a process similar to that of Example 22, except that using a SUS cylindrical calcination tube having an inner diameter of 300 mm, a length of 800 mm, and a wall thickness of 7 mm in which four weir plates having a height of 70 mm were mounted so as to divide the length of the heating furnace portion into five equal parts, the dry powder and nitrogen gas were allowed to flow through the calcination tube at a rate of 1.2 kg/hr and at 35 N liters/min, respectively. A pre-stage calcined powder was obtained. Next, main calcination was performed as in Example 22, except that using another SUS calcination tube having an inner diameter of 300 mm, a length of 800 mm, and a wall thickness of 7 mm in which seven weir plates having a height of 70 mm were mounted so as to divide the length of the heating furnace portion into eight equal parts, and while 23.1 g/hr of tungsten oxide [$WO_3$] having an average particle size of 40 μm and 0.7 kg/hr of the pre-stage calcined powder were allowed to flow through the calcination tube, nitrogen gas at 23 N liters/min was allowed to flow. After cooling, tungsten oxide having a small particle size was separated and removed from the obtained mainly calcined powder by a 32 μm sieve to obtain an oxide catalyst.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 1.

(Ammoxidation Reaction of Propane)

Propane was subjected to gas-phase ammoxidation reaction by the following process, using the oxide catalyst obtained as described above. A Vycor glass fluidized bed reaction tube having an inner diameter of 25 mm was filled with 35 g of the oxide catalyst. The reaction temperature was set to 440° C., and the reaction pressure was set to ordinary pressure. A mixed gas having a molar ratio of propane:ammonia:oxygen:helium=1:1:3:18 was supplied with a contact time of 2.8 (sec·g/cc). The propane conversion and the acrylonitrile yield after the reaction are shown in Table 1.

(Line Analysis of Catalyst Particle Cross Sections)

Line analysis by SEM-EDX measurement was performed on the obtained oxide catalyst, using SEM-6060A manufactured by JEOL Ltd. The oxide catalyst was embedded in an unsaturated polyester resin (cold embedding resin No. 105 manufactured by Marumoto Struers K.K.) to which a curing agent (M agent manufactured by the same company) was added, and the whole thereof was polished until cross sections of the embedded catalyst particles were exposed. The polishing was performed by a polishing machine (Musashino Denshi MA-150), using sandpaper No. 400, sandpaper No. 2000, and a wrapping sheet in turn, and finally, it was polished with an appropriate amount of a polishing agent (AP-A polishing alumina suspension manufactured by the same company) and water put in the polishing machine. Then, the position of the sample was adjusted so that the cross sections of the exposed catalyst particles were within the observation field of view in SEM-EDX measurement. For measurement conditions, a backscattered electron image was used, and acceleration voltage: 0-15 kV, dwell time: 1.0 msec, the number of scans: 5000, spot size: 50, and operating distance: 10 mm were set. A Si (Li) semiconductor was used for the detector.

For the calculation of Sw, 10 or more particles that were exposed to the center or its vicinity of the particles and had a particle size of 40 to 70 μm were subjected to line analysis measurement, and the average value of the Sw of the particles was taken for calculation.

Example 26

For the catalyst obtained in Example 10, line analysis was performed, and Sw was calculated, as described above. The result is shown in Table 3.

Example 27

For the catalyst obtained in Example 11, line analysis was performed, and Sw was calculated, as described above. The result is shown in Table 3.

Example 28

For the catalyst obtained in Example 12, line analysis was performed, and Sw was calculated, as described above. The result is shown in Table 3.

Example 29

For the catalyst obtained in Example 1, line analysis was performed, and Sw was calculated, as described above. The result is shown in Table 3.

Example 30

For the catalyst obtained in Example 3, line analysis was performed, and Sw was calculated, as described above. The result is shown in Table 3.

Example 31

For the catalyst obtained in Example 4, line analysis was performed, and Sw was calculated, as described above. The result is shown in Table 3.

Reference Example 1

Process for Producing Oxide Catalyst

A dry powder ($E_3$) was obtained as in Example 6.
(Calcination of Dry Powder ($E_3$))

The same SUS calcination tube as used in Example 1 was filled with 500 g of the dry powder ($E_3$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour, and then, main calcination was performed by increasing the temperature from room temperature to 670° C. at a temperature increase rate of 5° C./min, maintaining the temperature at 670° C. for 2 hours, and then decreasing the temperature to 350° C. at a temperature decrease rate of 1° C./min. After cooling, 100 g of the obtained oxide catalyst was impregnated with a liquid in which 3.4 g of an aqueous solution of ammonium metatungstate (containing tungsten (W) corresponding to 50% by mass in terms of $WO_3$) was diluted with water to 20 mL, dried in air at room temperature for about 1 day, and then dried in a hot air dryer at 150° C. for 1 hour. For the obtained catalyst, line analysis was performed, and Sw was calculated, as described above. The result is shown in Table 3.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 3.

Reference Example 2

Process for Producing Oxide Catalyst

A dry powder ($E_1$) was obtained as in Example 1.
(Calcination of Dry Powder ($E_1$))

The same SUS calcination tube as used in Example 1 was filled with 500 g of the dry powder ($E_1$) obtained as described above. Under nitrogen gas flow at 5.0 NL/min, while the calcination tube was rotated around the axis in its length direction, the temperature was increased from room temperature to 340° C. at a temperature increase rate of 0.75° C./min, and pre-stage calcination was performed under the conditions of 340° C. and 1 hour, and then, main calcination was performed by increasing the temperature from room temperature to 670° C. at a temperature increase rate of 5° C./min, maintaining the temperature at 670° C. for 2 hours, and then decreasing the temperature to 350° C. at a temperature decrease rate of 1° C./min. After cooling, 100 g of the obtained oxide catalyst was impregnated with a liquid in which 4.5 g of an aqueous solution of ammonium metatungstate (containing tungsten (W) corresponding to 50% by mass in terms of $WO_3$) was diluted with water to 20 mL, dried in air at room temperature for about 1 day, and then dried in a hot air dryer at 150° C. for 1 hour. For the obtained catalyst, line analysis was performed, and Sw was calculated, as described above. The result is shown in Table 3.

The composition of the catalyst was measured by X-ray fluorescence analysis (the trade name "RINT1000," manufactured by Rigaku, Cr tube, tube voltage: 50 kV, tube current: 50 mA).

$R_{W/Mo}/d$ is shown in Table 3.

TABLE 1

|  | Dry powder (*1) | Catalyst composition |
|---|---|---|
| Ex. 1 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Ex. 2 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Ex. 3 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Ex. 4 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Com. Ex. 1 | $E_2(Mo_1V_{0.22}W_{0.04}Nb_{0.10}Sb_{0.25})$ | $Mo_1V_{0.22}W_{0.04}Nb_{0.10}Sb_{0.25}O_n$/46.8 wt %-$SiO_2$ |
| Com. Ex. 2 | $E_1(Mo_1V_{0.22}Nb_{0.10}Sb_{0.25})$ | $Mo_1V_{0.22}W_{0.002}Nb_{0.10}Sb_{0.25}O_n$/47.8 wt %-$SiO_2$ |
| Com. Ex. 3 | $E_1(Mo_1V_{0.22}Nb_{0.10}Sb_{0.25})$ | $Mo_1V_{0.22}W_{0.35}Nb_{0.10}Sb_{0.25}O_n$/39.6 wt %-$SiO_2$ |
| Ex. 5 | $E_1(Mo_1V_{0.22}Nb_{0.10}Sb_{0.25})$ | $Mo_1V_{0.22}W_{0.03}Nb_{0.10}Sb_{0.25}Co_{0.03}O_n$/46.7 wt %-$SiO_2$ |
| Ex. 6 | $E_3(Mo_1V_{0.22}W_{0.04}Nb_{0.10}Sb_{0.25}Ce_{0.005})$ | $Mo_1V_{0.07}W_{0.07}Nb_{0.10}Sb_{0.25}Ce_{0.005}O_n$/47.1 wt %-$SiO_2$ |
| Com. Ex. 4 | $E_3(Mo_1V_{0.22}W_{0.04}Nb_{0.10}Sb_{0.25}Ce_{0.005})$ | $Mo_1V_{0.22}W_{0.04}Nb_{0.10}Sb_{0.25}Ce_{0.005}O_n$/47.2 wt %-$SiO_2$ |
| Ex. 7 | $E_4(Mo_1V_{0.33}Nb_{0.11}Te_{0.22})$ | $Mo_1V_{0.33}W_{0.05}Nb_{0.11}Te_{0.22}O_n$ |
| Com. Ex. 5 | $E_4(Mo_1V_{0.33}Nb_{0.11}Te_{0.22})$ | $Mo_1V_{0.33}Nb_{0.11}Te_{0.22}O_n$ |
| Ex. 9 | $E_2(Mo_1V_{0.22}W_{0.04}Nb_{0.10}Sb_{0.25})$ | $Mo_1V_{0.22}W_{0.07}Nb_{0.10}Sb_{0.25}O_n$/47.1 wt %-$SiO_2$ |
| Ex. 10 | $E_3(Mo_1V_{0.22}W_{0.04}Nb_{0.10}Sb_{0.25}Ce_{0.005})$ | $Mo_1V_{0.22}W_{0.07}Nb_{0.10}Sb_{0.25}Ce_{0.005}O_n$/47.1 wt %-$SiO_2$ |
| Ex. 11 | $E_3(Mo_1V_{0.22}W_{0.04}Nb_{0.10}Sb_{0.25}Ce_{0.005})$ | $Mo_1V_{0.22}W_{0.09}Nb_{0.10}Sb_{0.25}Ce_{0.005}O_n$/46.9 wt %-$SiO_2$ |
| Ex. 12 | $E_3(Mo_1V_{0.22}W_{0.04}Nb_{0.10}Sb_{0.25}Ce_{0.005})$ | $Mo_1V_{0.22}W_{0.12}Nb_{0.10}Sb_{0.25}Ce_{0.005}O_n$/46.7 wt %-$SiO_2$ |
| Com. Ex. 7 | $E_3(Mo_1V_{0.22}W_{0.04}Nb_{0.10}Sb_{0.25}Ce_{0.005})$ | $Mo_1V_{0.22}W_{0.042}Nb_{0.10}Sb_{0.25}O_n$/47.8 wt %-$SiO_2$ |
| Com. Ex. 8 | $E_3(Mo_1V_{0.22}W_{0.04}Nb_{0.10}Sb_{0.25}Ce_{0.005})$ | $Mo_1V_{0.22}W_{0.39}Nb_{0.10}Sb_{0.25}O_n$/39.6 wt %-$SiO_2$ |
| Ex. 13 | $E_5(Mo_1V_{0.30}Nb_{0.10}Sb_{0.22})$ | $Mo_1V_{0.30}W_{0.04}Nb_{0.10}Sb_{0.22}O_n$/46.8 wt %-$SiO_2$ |
| Ex. 14 | $E_6(Mo_1V_{0.15}Nb_{0.10}Sb_{0.30})$ | $Mo_1V_{0.15}W_{0.04}Nb_{0.10}Sb_{0.30}O_n$/46.6 wt %-$SiO_2$ |
| Ex. 15 | $E_7(Mo_1V_{0.24}Nb_{0.20}Sb_{0.25})$ | $Mo_1V_{0.24}W_{0.04}Nb_{0.20}Sb_{0.25}O_n$/46.8 wt %-$SiO_2$ |
| Ex. 16 | $E_8(Mo_1V_{0.22}Nb_{0.10}Sb_{0.25})$ | $Mo_1V_{0.22}W_{0.04}Nb_{0.10}Sb_{0.25}O_n$/54.9 wt %-$SiO_2$ |
| Ex. 17 | $E_9(Mo_1V_{0.22}Nb_{0.10}Sb_{0.25}B_{0.15})$ | $Mo_1V_{0.22}W_{0.04}Nb_{0.10}Sb_{0.25}B_{0.15}O_n$/46.9 wt %-$SiO_2$ |
| Ex. 18 | $E_{10}(Mo_1V_{0.22}Nb_{0.10}Sb_{0.25}Mn_{0.003}Ce_{0.006})$ | $Mo_1V_{0.22}W_{0.04}Nb_{0.10}Sb_{0.25}Mn_{0.003}Ce_{0.006}O_n$/46.8 wt %-$SiO_2$ |
| Ex. 19 | $E_{11}(Mo_1V_{0.22}Nb_{0.10}Sb_{0.25}Ta_{0.001}Ce_{0.005})$ | $Mo_1V_{0.22}W_{0.04}Nb_{0.10}Sb_{0.25}Ta_{0.001}Ce_{0.005}O_n$/46.9 wt %-$SiO_2$ |
| Ex. 20 | $E_{12}(Mo_1V_{0.22}Nb_{0.10}Sb_{0.25}Al_{0.005}Ti_{0.009})$ | $Mo_1V_{0.22}W_{0.04}Nb_{0.10}Sb_{0.25}Al_{0.005}Ti_{0.009}O_n$/46.8 wt %-$SiO_2$ |
| Ex. 21 | $E_{13}(Mo_1V_{0.22}Nb_{0.10}Sb_{0.25}La_{0.003})$ | $Mo_1V_{0.22}W_{0.04}Nb_{0.10}Sb_{0.25}La_{0.003}O_n$/46.7 wt %-$SiO_2$ |
| Ex. 22 | $E_{14}(Mo_1V_{0.22}W_{0.02}Nb_{0.10}Sb_{0.25}Bi_{0.015})$ | $Mo_1V_{0.22}W_{0.06}Nb_{0.10}Sb_{0.25}Bi_{0.015}O_n$/47.1 wt %-$SiO_2$ |
| Com. Ex. 9 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Com. Ex. 10 | $E_1(Mo_1V_{0.22}Nb_{0.10}Sb_{0.25})$ | $Mo_1V_{0.22}W_{0.0002}Nb_{0.10}Sb_{0.25}O_n$/47.8 wt %-$SiO_2$ |
| Com. Ex. 11 | $E_1(Mo_1V_{0.22}Nb_{0.10}Sb_{0.25})$ | $Mo_1V_{0.22}W_{4.0}Nb_{0.10}Sb_{0.25}O_n$/14.2 wt %-$SiO_2$ |
| Ex. 23 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Ex. 24 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |
| Ex. 25 | $E_1(Mo_1V_{0.22}Nb_{0.10}Sb_{0.25})$ | $Mo_1V_{0.22}W_{0.04}Nb_{0.10}Sb_{0.25}O_n$/46.7 wt %-$SiO_2$ |

|  | Added W | Calcination process | $R_{W/Mo}$ | d [μm] | $R_{W/Mo}/d$ [$m^{-1}$] | Conversion | Yield |
|---|---|---|---|---|---|---|---|
| Ex. 1 | $WO_3$ | (b-1) | 0.055 | 40 | 1376 | 89.2% | 52.9% |
| Ex. 2 | $WO_3$ | (b-2) | 0.066 | 40 | 1650 | 88.9% | 53.3% |
| Ex. 3 | $WO_3$ | (b-3) | 0.141 | 40 | 3530 | 89.5% | 53.1% |
| Ex. 4 | $WO_3$ | (b-2) | 0.065 | 40 | 1630 | 88.9% | 53.5% |
| Com. Ex. 1 | None | (a) | — | — | — | 89.0% | 52.3% |
| Com. Ex. 2 | $WO_3$ | (b-2) | 0.0005 | 500 | 1 | 88.8% | 52.2% |
| Com. Ex. 3 | $WO_3$ | (b-2) | 0.6 | 0.5 | 1200000 | 85.0% | 47.7% |
| Ex. 5 | $CoWO_4$ | (b-2) | 0.047 | 100 | 660 | 89.3% | 52.7% |
| Ex. 6 | $WO_3$ | (b-2) | 0.047 | 40 | 1170 | 88.9% | 53.5% |
| Com. Ex. 4 | None | (a) | — | — | — | 89.2% | 52.8% |
| Ex. 7 | $WO_3$ | (b-1) | 0.050 | 15 | 3350 | 89.5% | 58.2% |
| Com. Ex. 5 | None | (a) | — | — | — | 90.0% | 57.1% |
| Ex. 9 | $WO_3$ | (b-1) | 0.055 | 40 | 1454 | 88.8% | 52.8% |
| Ex. 10 | $WO_3$ | (b-1) | 0.058 | 40 | 1454 | 89.2% | 53.5% |
| Ex. 11 | $WO_3$ | (b-3) | 0.063 | 40 | 1580 | 88.7% | 53.5% |
| Ex. 12 | $WO_3$ | (b-2) | 0.084 | 40 | 2107 | 89.2% | 53.7% |
| Com. Ex. 7 | $WO_3$ | (b-2) | 0.0005 | 500 | 1 | 88.9% | 52.3% |
| Com. Ex. 8 | $WO_3$ | (b-2) | 0.6 | 0.5 | 1200000 | 83.8% | 46.5% |
| Ex. 13 | $WO_3$ | (b-2) | 0.058 | 40 | 1453 | 86.0% | 49.0% |
| Ex. 14 | $WO_3$ | (b-2) | 0.054 | 40 | 1346 | 85.0% | 50.2% |
| Ex. 15 | $WO_3$ | (b-2) | 0.055 | 40 | 1376 | 84.8% | 51.2% |
| Ex. 16 | $WO_3$ | (b-2) | 0.049 | 40 | 1230 | 87.0% | 51.9% |
| Ex. 17 | $WO_3$ | (b-2) | 0.062 | 40 | 1551 | 88.5% | 52.9% |
| Ex. 18 | $WO_3$ | (b-2) | 0.053 | 40 | 1328 | 88.7% | 52.7% |
| Ex. 19 | $WO_3$ | (b-2) | 0.060 | 40 | 1499 | 87.8% | 51.5% |

TABLE 1-continued

| | | | | | | | |
|---|---|---|---|---|---|---|---|
| Ex. 20 | WO$_3$ | (b-2) | 0.059 | 40 | 1476 | 87.5% | 51.4% |
| Ex. 21 | WO$_3$ | (b-2) | 0.056 | 40 | 1399 | 88.9% | 52.8% |
| Ex. 22 | WO$_3$ | (b-2) | 0.056 | 40 | 1400 | 89.1% | 52.9% |
| Com. Ex. 9 | WO$_3$ | (b-2) | 0.141 | 0.2 | 705000 | 88.7% | 52.4% |
| Com. Ex. 10 | WO$_3$ | (b-2) | 0.0001 | 50 | 2 | 88.8% | 52.3% |
| Com. Ex. 11 | WO$_3$ | (b-2) | 9.0 | 15 | 600000 | 70.5% | 43.2% |
| Ex. 23 | WO$_3$ | (b-2) | 0.066 | 40 | 1650 | 88.8% | 53.2% |
| Ex. 24 | WO$_3$ | (b-2) | 0.066 | 40 | 1650 | 88.6% | 52.9% |
| Ex. 25 | WO$_3$ | (b-2) | 0.066 | 40 | 1650 | 88.4% | 53.2% |

(*1) Letters and numbers in parentheses represent the feed atomic ratios of elements.

TABLE 2

| | Dry powder (*1) | Catalyst composition |
|---|---|---|
| Ex. 8 | E$_4$(Mo$_1$V$_{0.33}$Nb$_{0.11}$Te$_{0.22}$) | Mo$_1$V$_{0.33}$W$_{0.05}$Nb$_{0.11}$Te$_{0.22}$O$_n$ |
| Com. Ex. 6 | E$_4$(Mo$_1$V$_{0.33}$Nb$_{0.11}$Te$_{0.22}$) | Mo$_1$V$_{0.33}$Nb$_{0.11}$Te$_{0.22}$O$_n$ |

| | Added W | Calcination process | $R_{W/Mo}$ | d [μm] | $R_{W/Mo}$/d | Conversion | Yield |
|---|---|---|---|---|---|---|---|
| Ex. 8 | WO$_3$ | (b-1) | 0.050 | 15 | 3350 | 64.5% | 36.3% |
| Com. Ex. 6 | None | (a) | — | — | — | 64.0% | 34.7% |

(*1) Letters and numbers in parentheses represent the feed atomic ratios of elements.

TABLE 3

| | Dry powder (*1) | Catalyst composition |
|---|---|---|
| Ex. 26 | E$_3$(Mo$_1$V$_{0.22}$W$_{0.04}$Nb$_{0.10}$Sb$_{0.25}$Ce$_{0.005}$) | Mo$_1$V$_{0.22}$W$_{0.07}$Nb$_{0.10}$Sb$_{0.25}$Ce$_{0.005}$O$_n$/47.1 wt %-SiO$_2$ |
| Ex. 27 | E$_3$(Mo$_1$V$_{0.22}$W$_{0.04}$Nb$_{0.10}$Sb$_{0.25}$Ce$_{0.005}$) | Mo$_1$V$_{0.22}$W$_{0.09}$Nb$_{0.10}$Sb$_{0.25}$Ce$_{0.005}$O$_n$/46.9 wt %-SiO$_2$ |
| Ex. 28 | E$_3$(Mo$_1$V$_{0.22}$W$_{0.04}$Nb$_{0.10}$Sb$_{0.25}$Ce$_{0.005}$) | Mo$_1$V$_{0.22}$W$_{0.12}$Nb$_{0.10}$Sb$_{0.25}$Ce$_{0.005}$O$_n$/46.7 wt %-SiO$_2$ |
| Ex. 29 | E$_1$(Mo$_1$V$_{0.22}$Nb$_{0.10}$Sb$_{0.25}$) | Mo$_1$V$_{0.22}$W$_{0.04}$Nb$_{0.10}$Sb$_{0.25}$O$_n$/46.7 wt %-SiO$_2$ |
| Ex. 30 | E$_1$(Mo$_1$V$_{0.22}$Nb$_{0.10}$Sb$_{0.25}$) | Mo$_1$V$_{0.22}$W$_{0.04}$Nb$_{0.10}$Sb$_{0.25}$O$_n$/46.7 wt %-SiO$_2$ |
| Ex. 31 | E$_1$(Mo$_1$V$_{0.22}$Nb$_{0.10}$Sb$_{0.25}$) | Mo$_1$V$_{0.22}$W$_{0.04}$Nb$_{0.10}$Sb$_{0.25}$O$_n$/46.7 wt %-SiO$_2$ |
| Ref. Ex. 1 | E$_3$(Mo$_1$V$_{0.22}$W$_{0.04}$Nb$_{0.10}$Sb$_{0.25}$Ce$_{0.005}$) | Mo$_1$V$_{0.22}$W$_{0.07}$Nb$_{0.10}$Sb$_{0.25}$Ce$_{0.005}$O$_n$/47.1 wt %-SiO$_2$ |
| Ref. Ex. 2 | E$_1$(Mo$_1$V$_{0.22}$Nb$_{0.10}$Sb$_{0.25}$) | Mo$_1$V$_{0.22}$W$_{0.04}$Nb$_{0.10}$Sb$_{0.25}$O$_n$/46.7 wt %-SiO$_2$ |

| | Added W | Calcination process | $R_{W/Mo}$ | d [μm] | $R_{W/Mo}$/d | Sw |
|---|---|---|---|---|---|---|
| Ex. 26 | WO$_3$ | (b-1) | 0.058 | 40 | 1454 | 1.38 |
| Ex. 27 | WO$_3$ | (b-3) | 0.063 | 40 | 1580 | 1.29 |
| Ex. 28 | WO$_3$ | (b-2) | 0.084 | 40 | 2107 | 1.22 |
| Ex. 29 | WO$_3$ | (b-1) | 0.055 | 40 | 1376 | 1.36 |
| Ex. 30 | WO$_3$ | (b-3) | 0.141 | 40 | 3530 | 1.34 |
| Ex. 31 | WO$_3$ | (b-2) | 0.065 | 40 | 1630 | 1.2 |
| Ref. Ex. 1 | Impregnation | None | 0.058 | — | — | 1.02 |
| Ref. Ex. 2 | Impregnation | None | 0.055 | — | — | 1.01 |

(*1) Letters and numbers in parentheses represent the feed atomic ratios of elements.

This application is based on Japanese Patent Application No. 2010-248669 filed on Nov. 5, 2010, the content of which is incorporated herein by reference.

INDUSTRIAL APPLICABILITY

The present invention can provide an oxide catalyst that can be used for the gas phase catalytic oxidation reaction or gas phase catalytic ammoxidation reaction of propane or isobutane, and a production process suitable for industrially producing the oxide catalyst in a large amount. Therefore, the present invention has industrial applicability in their fields.

The invention claimed is:

1. A particulate oxide catalyst for use in the gas-phase catalytic oxidation reaction or the gas-phase catalytic ammoxidation reaction of propane or isobutane, the oxide catalyst containing a Mo compound, a V compound, a Nb compound, a compound of at least one element selected from the group consisting of Sb and Te, a W compound, and an optional compound of at least one element selected from the group consisting of Mn, B, Ti, Al, Ta, an alkali metal, an alkaline earth metal, La, Ce, Pr, Yb, Co, Y, and Sc, at atomic ratios represented by the following formula (0), wherein an average intensity of W present in a region within 5 μm from a surface toward a center of the particle of the oxide catalyst is equal to or greater than 1.08 times that of W present in the whole oxide catalyst:

$$C_{Mo}:C_V:C_W:C_{Nb}:C_X:C_Z = 1:a:w:c:x:z \qquad (0)$$

wherein $C_{Mo}$ represents the atomic ratio of Mo; $C_V$ represents the atomic ratio of V; $C_W$ represents the atomic ratio of W; $C_{Nb}$ represents the atomic ratio of Nb; $C_X$ represents the atomic ratio of at least one element selected from the group consisting of Sb and Te; $C_Z$ represents the atomic ratio of at least one element selected from the group consisting of Mn, B, Ti, Al, Ta, an alkali metal, an alkaline earth metal, La, Ce, Pr, Yb, Co, Y, and Sc; and a, w, c, x, and z fall within the ranges of $0.01 \leq a \leq 1$, $0 < w \leq 2$, $0.01 \leq c \leq 1$, $0.01 \leq x \leq 1$, and $0 \leq z \leq 1$, respectively, and wherein the particulate oxide catalyst has the ability to catalyze the gas-phase catalytic oxidation reaction or the gas-phase catalytic ammoxidation reaction of propane or isobutane.

2. A process for producing an oxide catalyst of claim 1 for use in the gas-phase catalytic oxidation reaction or the gas-phase ammoxidation reaction of propane or isobutane, the process comprising the steps of:

(I) obtaining a raw material preparation containing a Mo compound, a V compound, a Nb compound, a compound of at least one element selected from the group consisting of Sb and Te, an optional W compound, and an optional compound of at least one element selected from the group consisting of Mn, B, Ti, Al, Ta, an alkali metal, an alkaline earth metal, La, Ce, Pr, Yb, Co, Y, and Sc, at atomic ratios represented by the following formula (1);

(II) drying the raw material preparation to obtain a dry powder; and (III) calcining the dry powder, wherein the calcining step (III) comprises the step of calcining the dry powder in the presence of a compound containing W in the form of a solid to obtain a pre-stage calcined powder or a mainly calcined powder, or the step of calcining a pre-stage calcined powder obtained by calcining the dry powder in the presence of a compound containing W in the form of a solid to obtain a mainly calcined powder, and optionally comprises the step of further calcining the mainly calcined powder in the presence of a compound containing W in the form of a solid, the solid satisfies conditions represented by the following formula (2), and the oxide catalyst comprises a catalytic component having a composition represented by the following general formula (3):

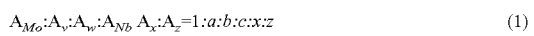

wherein $A_{Mo}$ represents the atomic ratio of Mo; $A_v$ represents the atomic ratio of V; $A_w$ represents the atomic ratio of W; $A_{Nb}$ represents the atomic ratio of Nb; Ax represents the atomic ratio of at least one element selected from the group consisting of Sb and Te; Az represents the atomic ratio of at least one element selected from the group consisting of Mn, B, Tl Al, Ta, an alkali metal, and an alkaline earth metal, La Ce, Pr, Yb, Co, Y, and Sc; and a, b, c, x, and z fall within the ranges of $0.01 \leq a \leq 1$, $0 \leq b \leq 1$, $0.01 \leq c \leq 1$, $0.01 \leq x \leq 1$, and $0 \leq z \leq 1$, respectively;

wherein $R_{W/Mo}$ represents the atomic ratio of W contained in the solid to Mo contained in the dry powder; and d represents the average particle size of the solid; and

wherein a, b, c, x, and z are each as defined above in the formula (1); X represents at least one element selected from the group consisting of Sb and Te; Z represents at least one element selected from the group consisting of Mn, B, Ti, Al, Ta, an alkali metal, an alkaline earth metal, La, Ce, Pr, Yb, Co, Y, and Sc; b' falls within the range of $0.001 \leq b' \leq 0.3$; and n represents a value which satisfies the balance of valence.

3. The process for producing an oxide catalyst according to claim 2, wherein the solid satisfies conditions represented by the following formulas (4) and (5):

wherein $R_{W/Mo}$ and d are each as defined above in the formula (2).

4. The process for producing an oxide catalyst according to claim 2, wherein in the formula (1), $0 < b \leq 1$.

5. The process for producing an oxide catalyst according to claim 2, wherein the Mo compound, the V compound, the W compound, the Nb compound, the compound represented by X, and the compound represented by Z in the dry powder, the pre-stage calcined powder, or the mainly calcined powder are each at least one selected from the group consisting of an inorganic acid salt, an organic acid salt, an oxide, and a complex oxide.

6. The process for producing an oxide catalyst according to claim 2, further comprising the step of spray-drying a solution or slurry containing W compound to obtain the solid.

7. The process for producing an oxide catalyst according to claim 2, wherein the oxide catalyst comprises the catalytic component supported on silica in an amount of 10 to 80% by mass in terms of $SiO_2$ based on the total amount of the catalytic component and the silica.

8. A process for producing a corresponding unsaturated acid from propane or isobutane by gas-phase catalytic oxidation reaction, the process comprising using an oxide catalyst obtained by a process according to claim 2.

9. A process for producing a corresponding unsaturated nitrile from propane or isobutane by gas-phase catalytic ammoxidation reaction, the process comprising using an oxide catalyst obtained by a production process according to claim 2.

10. The process for producing an oxide catalyst according to claim 3, wherein in the formula (1), $0 < b \; 1$.

11. The process for producing an oxide catalyst according to claim 3, wherein the Mo compound, the V compound, the W compound, the Nb compound, the compound represented by X, and the compound represented by Z in the dry powder, the pre-stage calcined powder, or the mainly calcined powder are each at least one selected from the group consisting of an inorganic acid salt, an organic acid salt, an oxide, and a complex oxide.

12. The process for producing an oxide catalyst according to claim 4, wherein the Mo compound, the V compound, the W compound, the Nb compound, the compound represented by X, and the compound represented by Z in the dry powder, the pre-stage calcined powder, or the mainly calcined powder are each at least one selected from the group consisting of an inorganic acid salt, an organic acid salt, an oxide, and a complex oxide.

13. The process for producing an oxide catalyst according to claim 3, further comprising the step of spray-drying a solution or slurry containing W compound to obtain the solid.

14. The process for producing an oxide catalyst according to claim 4, further comprising the step of spray-drying a solution or slurry containing W compound to obtain the solid.

15. The process for producing an oxide catalyst according to claim 5, further comprising the step of spray-drying a solution or slurry containing W compound to obtain the solid.

16. The process for producing an oxide catalyst according to claim 3, wherein the oxide catalyst comprises the catalytic component supported on silica in an amount of 10 to 80% by mass in terms of $SiO_2$ based on the total amount of the catalytic component and the silica.

17. The process for producing an oxide catalyst according to claim 4, wherein the oxide catalyst comprises the catalytic component supported on silica in an amount of 10 to 80% by mass in terms of $SiO_2$ based on the total amount of the catalytic component and the silica.

18. The process for producing an oxide catalyst according to claim 5, wherein the oxide catalyst comprises the catalytic component supported on silica in an amount of 10 to 80% by mass in terms of $SiO_2$ based on the total amount of the catalytic component and the silica.

19. The process for producing an oxide catalyst according to claim 6, wherein the oxide catalyst comprises the catalytic component supported on silica in an amount of 10 to 80% by mass in terms of $SiO_2$ based on the total amount of the catalytic component and the silica.

\* \* \* \* \*